United States Patent
Maples et al.

(10) Patent No.: US 9,617,586 B2
(45) Date of Patent: *Apr. 11, 2017

(54) NICKING AND EXTENSION AMPLIFICATION REACTION FOR THE EXPONENTIAL AMPLIFICATION OF NUCLEIC ACIDS

(75) Inventors: Brian K. Maples, San Diego, CA (US); Rebecca C. Holmberg, Rockville, MD (US); Andrew P. Miller, San Diego, CA (US); Jarrod Provins, Dana Point, CA (US); Richard B. Roth, San Diego, CA (US); Jeffrey Mandell, La Jolla, CA (US)

(73) Assignee: Ionian Technologies, Inc., San Diego, CA (US)

(*) Notice: Subject to any disclaimer, the term of this patent is extended or adjusted under 35 U.S.C. 154(b) by 194 days.

This patent is subject to a terminal disclaimer.

(21) Appl. No.: 12/173,020

(22) Filed: Jul. 14, 2008

(65) Prior Publication Data

US 2009/0081670 A1    Mar. 26, 2009

Related U.S. Application Data

(63) Continuation-in-part of application No. 11/778,018, filed on Jul. 14, 2007.

(51) Int. Cl.
    *C12Q 1/68*    (2006.01)
(52) U.S. Cl.
    CPC .................. *C12Q 1/6844* (2013.01)
(58) Field of Classification Search
    None
    See application file for complete search history.

(56) References Cited

U.S. PATENT DOCUMENTS

| | | |
|---|---|---|
| 5,210,015 A | 5/1993 | Gelfand et al. |
| 5,270,184 A | 12/1993 | Walker et al. |
| 5,354,668 A | 10/1994 | Auerbach |
| 5,397,698 A | 3/1995 | Goodman et al. |
| 5,422,252 A | 6/1995 | Walker et al. |
| 5,455,166 A | 10/1995 | Walker |
| 5,470,723 A | 11/1995 | Walker et al. |
| 5,487,972 A | 1/1996 | Gelfand et al. |
| 5,556,751 A | 9/1996 | Stefano |
| 5,591,609 A | 1/1997 | Auerbach |
| 5,614,387 A | 3/1997 | Shen et al. |
| 5,614,389 A | 3/1997 | Auerbach |
| 5,648,211 A | 7/1997 | Fraiser et al. |
| 5,681,705 A | 10/1997 | Schram et al. |
| 5,712,124 A | 1/1998 | Walker |
| 5,733,733 A | 3/1998 | Auerbach |
| 5,736,365 A | 4/1998 | Walker et al. |
| 5,744,311 A | 4/1998 | Fraiser et al. |
| 5,747,246 A | 5/1998 | Pannetier et al. |
| 5,747,255 A | 5/1998 | Brenner |
| 5,804,375 A | 9/1998 | Gelfand et al. |
| 5,834,202 A | 11/1998 | Auerbach |
| 5,834,254 A | 11/1998 | Shen et al. |
| 5,840,487 A | 11/1998 | Nadeau et al. |
| 5,846,717 A | 12/1998 | Brow et al. |
| 5,916,779 A | 6/1999 | Pearson et al. |
| 5,928,869 A | 7/1999 | Nadeau et al. |
| 5,942,391 A | 8/1999 | Zhang et al. |
| 5,985,557 A | 11/1999 | Prudent et al. |
| 6,033,881 A * | 3/2000 | Himmler et al. ............ 435/91.2 |
| 6,040,166 A | 3/2000 | Erlich et al. |
| 6,063,604 A | 5/2000 | Wick et al. |
| 6,077,669 A | 6/2000 | Little et al. |
| 6,087,133 A | 7/2000 | Dattagupta et al. |
| 6,090,552 A | 7/2000 | Nazarenko et al. |
| 6,110,677 A | 8/2000 | Western et al. |
| 6,130,038 A | 10/2000 | Becker et al. |
| 6,191,267 B1 * | 2/2001 | Kong et al. ............ 536/23.4 |
| 6,214,587 B1 | 4/2001 | Dattagupta et al. |
| 6,251,600 B1 | 6/2001 | Winger et al. |
| 6,261,768 B1 | 7/2001 | Todd et al. |
| 6,294,337 B1 | 9/2001 | Hayashizaki |
| 6,316,200 B1 | 11/2001 | Nadeau et al. |
| 6,335,164 B1 | 1/2002 | Kigawa et al. |
| 6,348,314 B1 | 2/2002 | Prudent et al. |
| 6,350,580 B1 | 2/2002 | Sorge |
| 6,372,434 B1 | 4/2002 | Weissman et al. |
| 6,403,341 B1 | 6/2002 | Barnes et al. |
| 6,423,495 B1 | 7/2002 | Oultram et al. |
| 6,482,590 B1 | 11/2002 | Ullman et al. |
| 6,566,103 B2 | 5/2003 | Wijnhoven et al. |
| 6,632,611 B2 | 10/2003 | Su et al. |
| 6,656,680 B2 | 12/2003 | Nadeau et al. |
| 6,660,475 B2 | 12/2003 | Jack et al. |

(Continued)

FOREIGN PATENT DOCUMENTS

| | | |
|---|---|---|
| CN | 1850981 | 10/2006 |
| EP | 2657350 | 10/2013 |

(Continued)

OTHER PUBLICATIONS

Van Ness et al. (2003) Proc. Nat. Acad. Sci. USA vol. 100 No. 8 pp. 4504-4509.*
Saiki et al. Science (1988) vol. 239 pp. 487-491.*
Demidov (2002) Expert Rev. Mol. Diagn. vol. 2 (6) pp. 89-95.*
Cai, H Publication LAUR#05-9067 of Los Alamos National Laboratory dated Aug. 22, 2006.*
Tan et al. (2005) Anal. Chem vol. 77; pp. 7984-7992.*
Nuovo (2000) Diagnostic Molecular pathology 9(4):195-202.*
Allshire, Science, 297:1818-19 (2002).
Bass, Nature, 411:428-429 (2001).
Baulcombe et al., Science, 297:2002-03 (2002).
Buck et al., BioTechniques, 27:528-536 (1999).
Church et al., Science, 240:185-188 (1988).
Corstjens et al., Clin. Chem., 47:1885-93 (2001).
Crain et al., Curr. Opin. Biotechnol., 9:25-34 (1998).
Dean et al., Proc. Natl. Acad. Sci. USA, 8:5261-66 (2002).

(Continued)

*Primary Examiner* — Angela M Bertagna
(74) *Attorney, Agent, or Firm* — Fish & Richardson P.C.

(57) ABSTRACT

The invention is in general directed to the rapid exponential amplification of short DNA or RNA sequences at a constant temperature.

38 Claims, 34 Drawing Sheets

(56) References Cited

U.S. PATENT DOCUMENTS

| | | |
|---|---|---|
| 6,686,150 B1 | 2/2004 | Blackburn et al. |
| 6,692,917 B2 | 2/2004 | Neri et al. |
| 6,713,297 B2 | 3/2004 | McMillan et al. |
| 6,743,582 B2 | 6/2004 | Nadea et al. |
| 6,767,724 B2 | 7/2004 | Lee et al. |
| 6,811,971 B2 | 11/2004 | Klepp et al. |
| 6,861,222 B2 | 3/2005 | Ward et al. |
| 6,884,586 B2 | 4/2005 | Van Ness et al. |
| 6,893,819 B1 | 5/2005 | Sorge |
| 6,929,915 B2 | 8/2005 | Benkovic et al. |
| 6,958,217 B2 | 10/2005 | Pedersen |
| 6,977,148 B2 | 12/2005 | Dean et al. |
| 7,074,600 B2 | 7/2006 | Dean et al. |
| 7,112,423 B2 | 9/2006 | Van Ness et al. |
| 7,270,981 B2 | 9/2007 | Armes et al. |
| RE39,885 E | 10/2007 | Nadeau et al. |
| 7,276,597 B2 | 10/2007 | Sorge |
| 7,297,485 B2 | 11/2007 | Bornarth et al. |
| 7,309,573 B2 | 12/2007 | Sorge |
| 7,399,590 B2 | 7/2008 | Piepenburg et al. |
| 7,972,820 B2 | 7/2011 | Mayer |
| 2002/0042059 A1 | 4/2002 | Makarov et al. |
| 2002/0150919 A1 | 10/2002 | Weismann et al. |
| 2003/0082590 A1 | 5/2003 | Van Ness et al. |
| 2003/0138800 A1 | 7/2003 | Van Ness et al. |
| 2003/0165911 A1 | 9/2003 | Van Ness et al. |
| 2004/0038256 A1 | 2/2004 | Van Ness et al. |
| 2004/0058349 A1 | 3/2004 | Van Ness et al. |
| 2004/0058378 A1 | 3/2004 | Kong et al. |
| 2005/0009050 A1 | 1/2005 | Nadeau et al. |
| 2005/0042601 A1 | 2/2005 | Wolfe |
| 2005/0112639 A1 | 5/2005 | Wang et al. |
| 2005/0147973 A1 | 7/2005 | Knott |
| 2005/0164207 A1 | 7/2005 | Shapero |
| 2005/0202490 A1 | 9/2005 | Makarov et al. |
| 2005/0233332 A1 | 10/2005 | Collis |
| 2005/0266417 A1 | 12/2005 | Barany et al. |
| 2006/0154286 A1 | 7/2006 | Kong et al. |
| 2006/0160759 A1 | 7/2006 | Chen et al. |
| 2006/0257860 A1 | 11/2006 | Marlowe et al. |
| 2007/0020639 A1 | 1/2007 | Shapero |
| 2007/0031857 A1 | 2/2007 | Makarov et al. |
| 2008/0038782 A1 | 2/2008 | Borns |
| 2008/0096257 A1 | 4/2008 | Yao et al. |
| 2009/0011472 A1* | 1/2009 | Nelson ............... C12Q 1/6858 435/91.53 |
| 2009/0017453 A1 | 1/2009 | Maples et al. |
| 2009/0081670 A1 | 3/2009 | Maples et al. |
| 2009/0092967 A1* | 4/2009 | Yao et al. ............... 435/6 |
| 2009/0111089 A1 | 4/2009 | Lindstrom et al. |
| 2010/0184205 A1 | 7/2010 | Bentwich et al. |
| 2010/0204297 A1 | 8/2010 | Chen et al. |
| 2014/0072978 A1 | 3/2014 | Maples et al. |
| 2014/0093883 A1 | 4/2014 | Maples et al. |

FOREIGN PATENT DOCUMENTS

| | | |
|---|---|---|
| EP | 2660333 | 11/2013 |
| EP | 2824189 | 1/2015 |
| GB | 2416352 | 1/2006 |
| WO | WO94/03635 | 2/1994 |
| WO | WO 98/39485 | 9/1998 |
| WO | WO 99/07409 | 2/1999 |
| WO | WO 99/32619 | 7/1999 |
| WO | WO 00/01846 | 1/2000 |
| WO | WO 00/28084 | 5/2000 |
| WO | WO 00/44895 | 8/2000 |
| WO | WO 00/44914 | 8/2000 |
| WO | WO 01/29058 | 4/2001 |
| WO | WO 01/36646 | 5/2001 |
| WO | WO 03/008622 | 1/2003 |
| WO | WO 03/008624 | 1/2003 |
| WO | WO 03/008642 | 1/2003 |
| WO | WO03/012066 | 2/2003 |
| WO | WO 03/066802 | 8/2003 |
| WO | WO 03/072805 | 9/2003 |
| WO | WO 03/080645 | 10/2003 |
| WO | WO 03080645 A2 * | 10/2003 |
| WO | WO 2004/022701 | 3/2004 |
| WO | WO 2004/067726 | 8/2004 |
| WO | WO 2004/067764 | 8/2004 |
| WO | WO 2004/081183 | 9/2004 |
| WO | WO 2005/026329 | 3/2005 |
| WO | WO 2005/118853 | 12/2005 |
| WO | WO2007/028833 | 3/2007 |
| WO | WO2007/096182 | 8/2007 |
| WO | WO2007096702 | 8/2007 |
| WO | WO2008/002920 | 1/2008 |
| WO | WO2011/085160 | 7/2011 |
| WO | WO2015/113828 | 8/2015 |
| WO | WO2016/004333 | 1/2016 |

OTHER PUBLICATIONS

Elbashir et al., Nature, 411:494-498 (2001).
Hall et al., Science, 297:2232-37 (2002).
Hiquchi et al., Nature Biotechnol., 10:413-417(1992).
Hite et al., Nucl. Acids Res., 1996, 24: 2429-34 (1996).
Hutvagner et al., Science, 297:2056-60 (2002).
Jenuwein, Science, 297:2215-18 (2002).
Koster et al., Nature Biotechnol., 14:1123-28 (1996).
Kurn et al., Clin. Chem., 51:1973-81 (2005).
Lagos-Quintana et al, Science, 294:853-858 (2001).
Lau et al., Science, 294:858-862 (2001).
Lee et al., Science, 294:862.864 (2001).
Limbach P, Mass Spectrom. Rev., 15:297-336 (1996).
Lizardi et al., Nature Biotech, 6:1197-1202 (1998).
Llave, Science, 297:2053-56 (2002).
McManus et al., RNA, 8:842-850 (2002).
Murray K., J. Mass Spectrom., 31:1203-15 (1996).
Notomi et al., Nucl. Acids Res., 28, 12, e63 (2000).
Reinhart et al., Genes Dev., 16:1616-26 (2002).
Reinhart et al., Science, 297:1831 (2002).
Ruvkun G., Science, 294:797-799 (2001).
Singer et al., Anal. Biochem., 249:229-238 (1997).
Tan et al., Anal. Chem., 77:7984-92 (2005).
Tyagi et al., Nature Biotechnol., 14:303-308 (1996).
Van Ness et al., Proc. Natl. Acad. Sci. USA, 100:4504-09 (2003).
Volpe et al., Science, 297:1833-37 (2002).
Wade N., "Studies Reveal an Immune System Regulator", New York Times (2007).
Zamore et al., Cell, 101:25-33 (2000).
Restriction Requirement issued in U.S. Appl. No. 11/778,018, mailed Jun. 5, 2009.
Grant Anderson LLP, Response to Restrictions Requirement issued in U.S. Appl. No. 11/778,018, mailed Jul. 2, 2009.
Non-Final Office Action issued in U.S. Appl. No. 11/778,018, mailed Sep. 16, 2009.
Grant Anderson LLP, Response to Non-Final Office Action issued in U.S. Appl. No. 11/778,018, mailed Dec. 9, 2009.
Interview Summary issued in U.S. Appl. No. 11/778,018, mailed Mar. 24, 2010.
Final Office Action issued in U.S. Appl. No. 11/778,018, mailed Mar. 26, 2010.
Grant Anderson LLP, Request for Continued Examination and Response to Final Office Action issued in U.S. Appl. No. 11/778,018, mailed Jul. 26, 2010.
International Search Report, for the corresponding PCT Application No. PCT/US2008/070023, dated Jan. 19, 2009.
EP Office Action for corresponding EP Application No. 08 781827.4, dated Mar. 13, 2012.
Final Office Action in U.S. Appl. No. 11/778,018, mailed Feb. 6, 2012.
English translation of Chinese Second Office action, for corresponding Chinese application CN 200880105424.7. dated Jun. 5, 2013.
Kentaro Nagimine et al., "Loop-mediated Isothermal Amplification Reaction Using a Nondenatured Template," Clinical Chemistry, 47(9):1742-1743 (2001).

(56) References Cited

OTHER PUBLICATIONS

English translation and Chinese Office action, for corresponding Chinese application CN 200880105424.7. dated Jul. 23, 2012.
AU Office Action for corresponding AU Application No. 2008276118, 4 pages, dated May 1, 2013.
English translation of Chinese Third Office action, for corresponding Chinese application CN 200880105424.7. dated Feb. 8, 2014.
Notification of the Final Rejection for corresponding Chinese application CN 200880105424.7. dated Jun. 5, 2014.
Sequence of vector pUC19, downloaded from http://genome-www.stanford.edu/vectordb/vector_descrip/COMPLET . . . On Mar. 27, 2014.
Notice of Opposition in corresponding EP Application No. 08781827.4, dated May 6, 2014, pp. 1-36.
Notice of Allowance in corresponding Japanese Application No. 2010-517111, dated Jan. 15, 2015, pp. 1-3.
Response to Examination Report in corresponding Australian Application No. 2008276118, dated Jan. 23, 2015, pp. 1-5.
Response to Office Action dated Jul. 31, 2014, for corresponding Canadian Application No. 2693805, dated Jan. 30, 2015, pp. 1-62.
Response of Patentee to Opposition in corresponding EP Application No. 08781827.4 (EP 2 181 196), dated Jan. 7, 2015, pp. 1-36.
Walker et al., "Isothermal in vitro amplification of DNA by a restriction enzyme/DNA polymerase system," PNAS, 89:392-396 (1992).
Interview Summary from corresponding U.S. Appl. No. 14/067,623, dated Dec. 12, 2014, pp. 1-3.
Interview Summary from corresponding U.S. Appl. No. 14/067,620, dated Dec. 12, 2014, pp. 1-3.
Interview Summary from corresponding U.S. Appl. No. 11/778,018, dated Dec. 15, 2014, pp. 1-3.
Summons to Oral Proceedings in corresponding European Application No. 08781827.4, dated Jan. 14, 2016, pp. 1-17.
Walker et al., "Strand displacement amplification- an iso-thermal, in vitro DNA amplification technique," Nucl. Acids Res. 20:1691-1696 (1992).
Walker et al., "Multiplex strand displacement amplification (SDA) and detection of DNA sequences from *Mycobacterium tuberculosis* and other mycobacteria," Nucl. Acids Res. 22:2670-2677 (1994).
Walker, "Empirical Aspects of Strand Displacement Amplification," PCR Methods and Appl., 3:1-6 (1993).
Walker, et al., "Strand displacement amplification as an in vitro model for rolling-circle replication: Deletion formation and evolution during serial transfer," PNAS, 91:7937-7941 (1994).
Nuovo GJ, "In situ strand displacement amplification: an improved technique for the detection of low copy nucleic acids," Diagnostic Molecular Pathology, 2000, 9(4):195-202.
Zhu et al., "Engineering strand-specific DNA nicking enzymes from the type IIS restriction endonucleases BsaI, BsmBI, and BsmAI," J. Mol. Biol. 2004, 337:573-583.
Notice of Opposition in corresponding Application No. 08781827.4/2181196, dated Aug. 7, 2015, pp. 1-21.

Extended European Search Report in corresponding Application No. 13799829.0, dated Mar. 31, 2016, pp. 1-10.
Arena et al., "Calcium- and Magnesium-EDTA Complexes. Stability Constants and Their Dependence on Temperature and Ionic Strength," Thermochimica Acta, 61 (1983) 129-138.
Examiner's Report in corresponding Canadian Application No. 2,693,805 dated Mar. 18, 2016, pp. 1-5.
Little et al., "Molecular Diagnostics and Genetics," Clinical Chemistry, 45:6, 777-784 (1999).
Wang et al., "Homogeneous Real-Time Detection of Single-Nucleotide Polymorphisms by Strand Displacement Amplification on the BD ProbeTec ET System," Clinical Chemistry, 49:10, 1599-1607 (2003).
C.A. Spargo et al., "Detection of M. tuberculosis DNA using Thermophilic Strand Displacement Amplification," Molecular and Cellular Probes (1996) 10, 247-256.
Chinese Office Action in Application No. 201410465144.4, dated Jun. 28, 2016, pp. 1-9.
Notification of Reexamination in Chinese Application No. 200880105424.7, pp. 1-8.
Chinese Office Action in Application No. 201410466581.8, dated Jan. 21, 2016, pp. 1-20.
Chinese Office Action in Application No. 201410465144.4, dated Dec. 1, 2015, pp. 1-7.
Ehses et al., "Optimization and design of oligonucleotide setup for strand displacement amplification," J. Biochem. Biophys. Methods, 63 (2005) 170-186.
Artificial DNA: Methods and Applications (2003), Khudyakov Y.E. & Fields, H.A. (Eds), *Synthetic DNA Used in Amplification Reactions* (pp. 115-159), CRC Press LLC.
Nadezhda V. Zyrina et al., "N.BspD6I DNA nickase strongly stimulates template-independent synthesis of non-palindromic repetitive DNA by Bst DNA polymerase," Biol. Chem. vol. 388, pp. 367-372, Apr. 2007.
Baudin et al., "Structure of influenza virus RNP. I. Influenza virus nucleoprotein melts secondary structure in panhandle RNA and exposes the bases to the solvent," EMBO J., 13(13):3158-3165, Jul. 1, 1994.
Brown et al., "Secondary structure of the 5' nontranslated regions of hepatitis C virus and pestivirus genomic RNAs," Nucleic Acids Res., 20(19):5041-5045, Oct. 11, 1992.
McDowell DG, Burns NA, Parkes HC. Localised sequence regions possessing high melting temperatures prevent the amplification of a DNA mimic in competitive PCR. Nucleic Acids Res. Jul. 15, 1998; 26(14):3340-7.
Australian Office Action in corresponding Application No. 2015202439, dated Sep. 28, 2016, pp. 1-4.
Extended European Search Report in EP Application No. 12195331.9, dated Oct. 2, 2013, pp. 1-7.
Extended European Search Report in EP Application No. 12195333.5, dated Oct. 9, 2013, pp. 1-9.

* cited by examiner

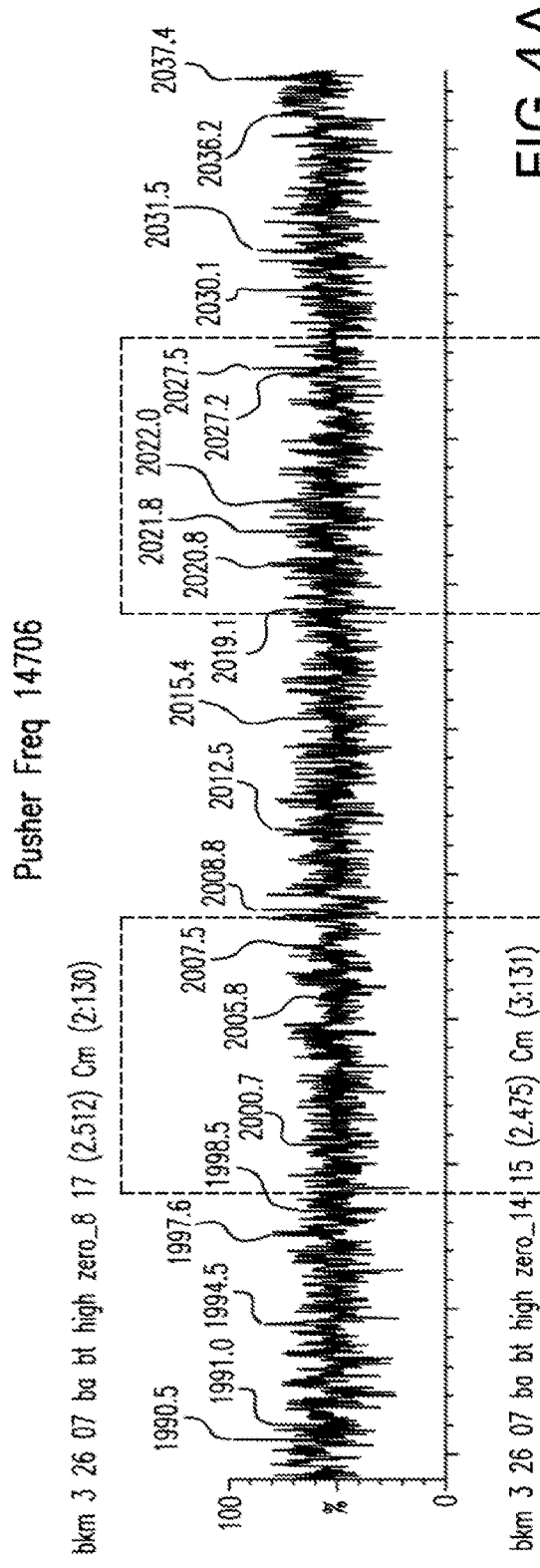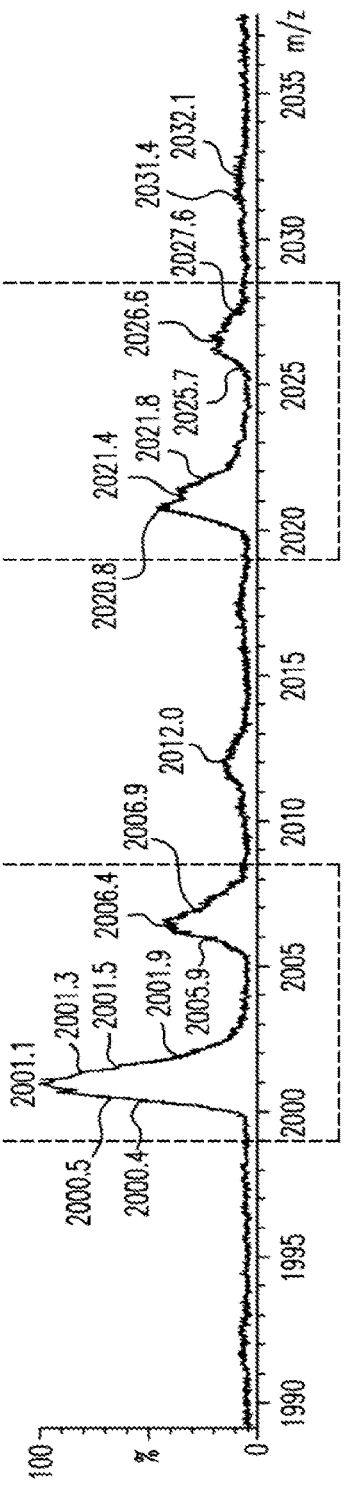

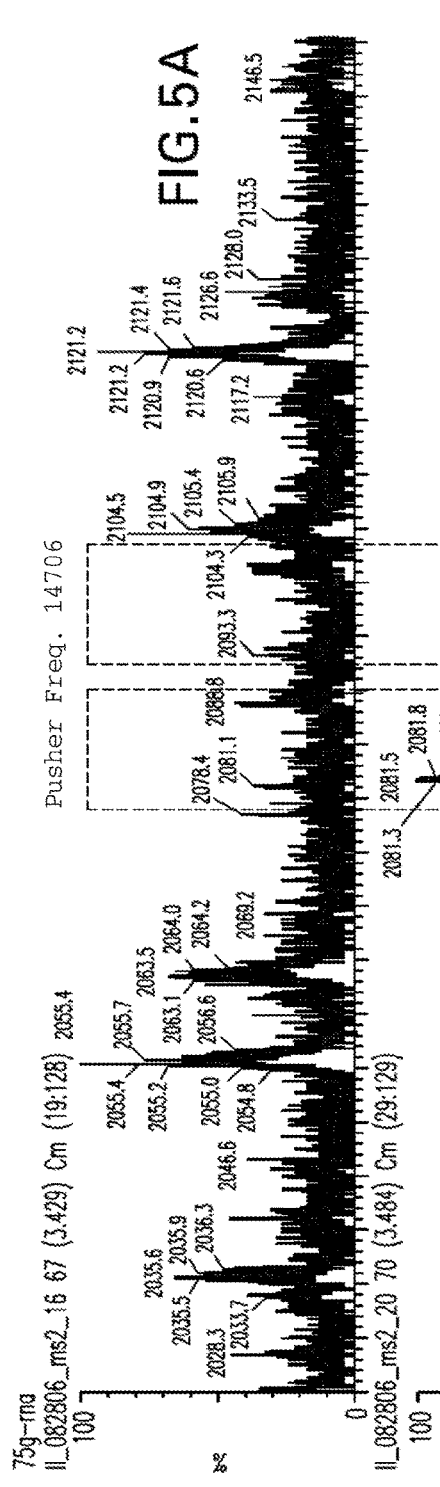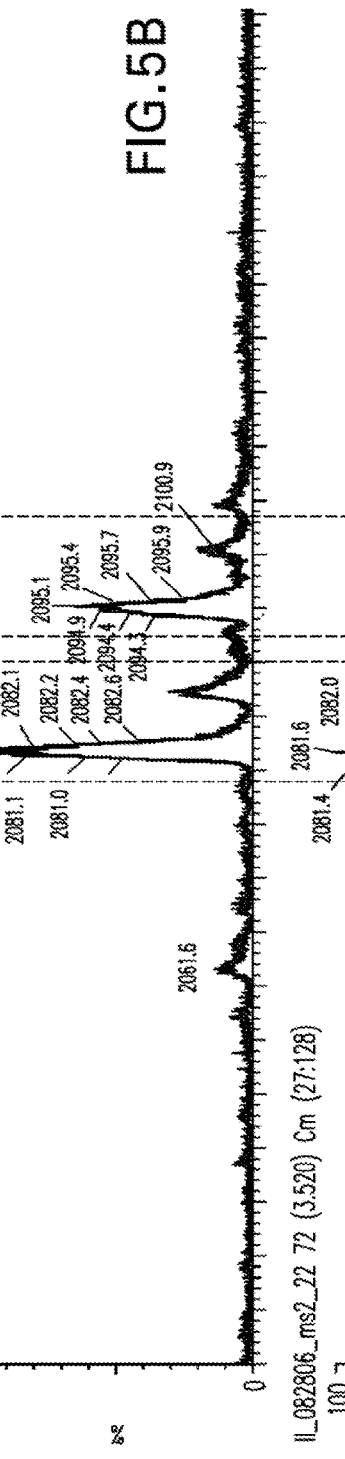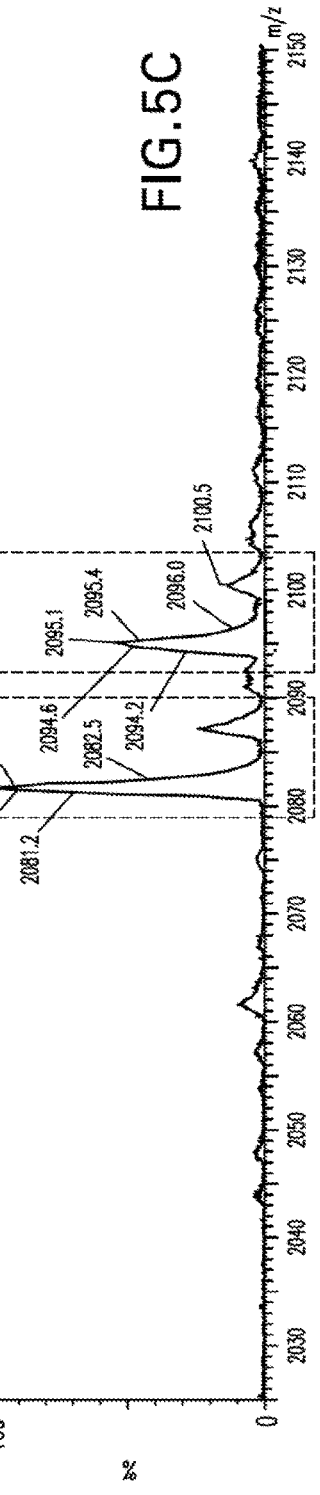

Marker 0 0 0 0 +MS2 +MS2 +MS2/Ebola

← 27mer
← 25mer
← 23mer

FIG. 18

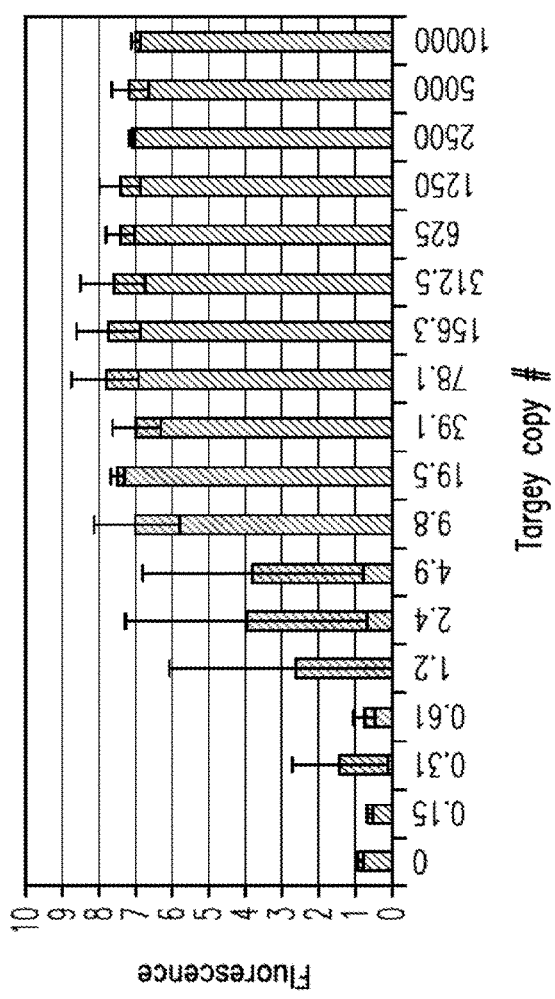
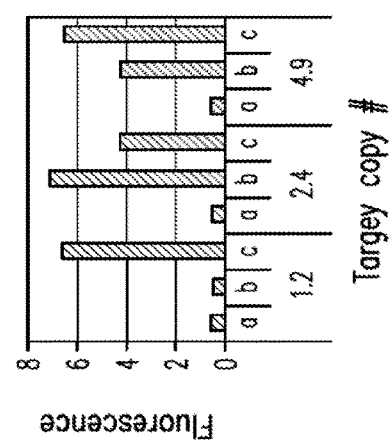
FIG.22A
FIG.22B

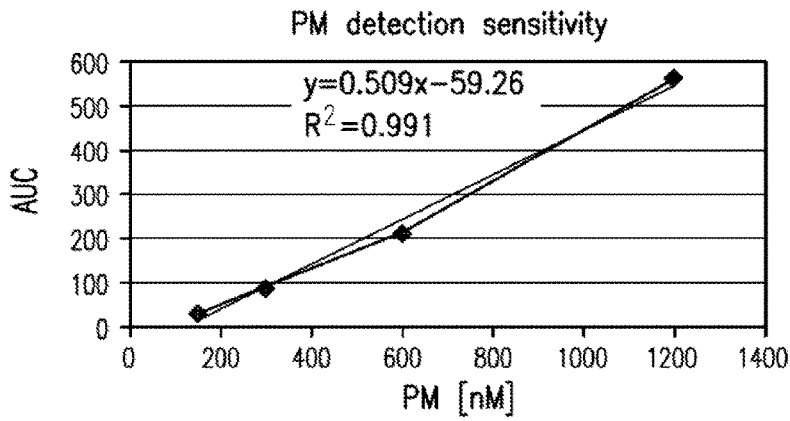
FIG.28A
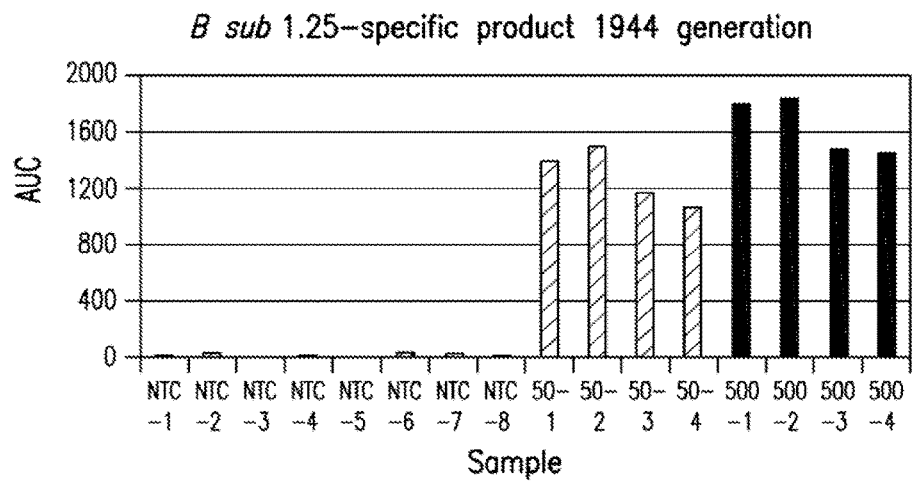
FIG.28B
| Specific product 1944 yields (x=y-b/m) | | |
|---|---|---|
| Sample | AUC signal | Product [nM] |
| 50-1 | 1394 | 2851 |
| 50-2 | 1495 | 3049 |
| 50-3 | 1175 | 2421 |
| 50-4 | 1072 | 2219 |
| 500-1 | 1799 | 3645 |
| 500-2 | 1837 | 3720 |
| 500-3 | 1472 | 3004 |
| 500-4 | 1438 | 2937 |
FIG.28C

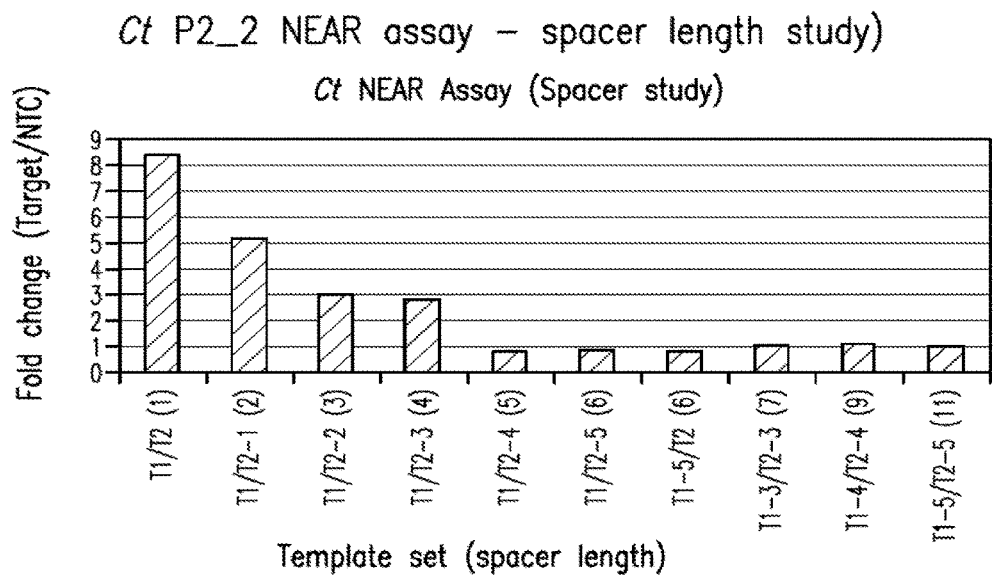

FIG. 29A

| Temp1 | 12mer | | ATGCATGCATGAGTCACATAGGCTTATGGAG |
|---|---|---|---|
| Temp1 | -1 | 12mer | ATGCATGCATGAGTCACATgAGGCTTATGGA |
| Temp1 | -2 | 12mer | ATGCATGCATGAGTCACATagAGGCTTATGG |
| Temp1 | -3 | 12mer | ATGCATGCATGAGTCACATtagAGGCTTATG |
| Temp1 | -4 | 12mer | ATGCATGCATGAGTCACATttagAGGCTTAT |
| Temp1 | -5 | 12mer | ATGCATGCATGAGTCACATcttagAGGCTTA |
| | | | |
| Temp2 | 12mer | | ATGCATGCATGAGTCACATTTATACCGCTTA |
| Temp2 | -1 | 12mer | ATGCATGCATGAGTCACATtTTATACCGCTT |
| Temp2 | -2 | 12mer | ATGCATGCATGAGTCACATttTTATACCGCT |
| Temp2 | -3 | 12mer | ATGCATGCATGAGTCACATgttTTATACCGC |
| Temp2 | -4 | 12mer | ATGCATGCATGAGTCACATtgttTTATACCG |
| Temp2 | -5 | 12mer | ATGCATGCATGAGTCACATatgttTTATACC |

FIG. 29B

Ct NEAR assay–Template designs to analyze effect of spacer length

| Seq ID | Seq orientation | Sequence |
|---|---|---|
| T2-5 | 3'/5' | CCATATTTtgtaTACACTGAGTACGTACGTA |
| T2-4 | 3'/5' | GCCATATTTtgtaTACACTGAGTACGTACGTA |
| T2-3 | 3'/5' | CGCCATATTTtgtaTACACTGAGTACGTACGTA |
| T2-2 | 3'/5' | TCGCCATATTTtTACACTGAGTACGTACGTA |
| T2-1 | 3'/5' | TTCGCCATATTtTACACTGAGTACGTACGTA |
| T2 | 3'/5' | ATTCGCCCATATTTACACTGAGTACGTACGTA |
| Target-sense | 5'/3' | cttagAGGCTTATGGAGTTAACCGGTATAAG |
| Target-antisense | 3'/5' | gaatcTCCGAATACCTCAATTGGCCATATTTtgta |
| T1 | 5'/3' | ATGCATGCATGAGTCACATGAGCTTATGGAG |
| T1-1 | 5'/3' | ATGCATGCATGAGTCACATGAGCTTATGGA |
| T1-2 | 5'/3' | ATGCATGCATGAGTCACATGAGCTTATGG |
| T1-3 | 5'/3' | ATGCATGCATGAGTCACATagAGGCTTATG |
| T1-4 | 5'/3' | ATGCATGCATGAGTCACATtagAGGCTTA |
| T1-5 | 5'/3' | ATGCATGCATGAGTCACATcttagAGGCTTA |

Example – 11mer spacer

| Seq ID | Seq orientation | Sequence |
|---|---|---|
| T2-5 | 3'/5' | CCATATTTtgtaTACACTGAGTACGTACGTA |
| Target-sense | 5'/3' | cttagAGGCTTATGGAGTTAACCGGTATAAG |
| Target-antisense | 3'/5' | gaatcTCCGAATACCTCAATTGGCCATATTTtgta |
| T1-5 | 5'/3' | cttagAGGCTTATGGAGTTAACCGGTATAAG |
| Product (35mer) | 5'/3' | ATGCATGCATGAGTCACATcttagAGGCTTA | stabilizing region — nicking site — spacer region

FIG. 30

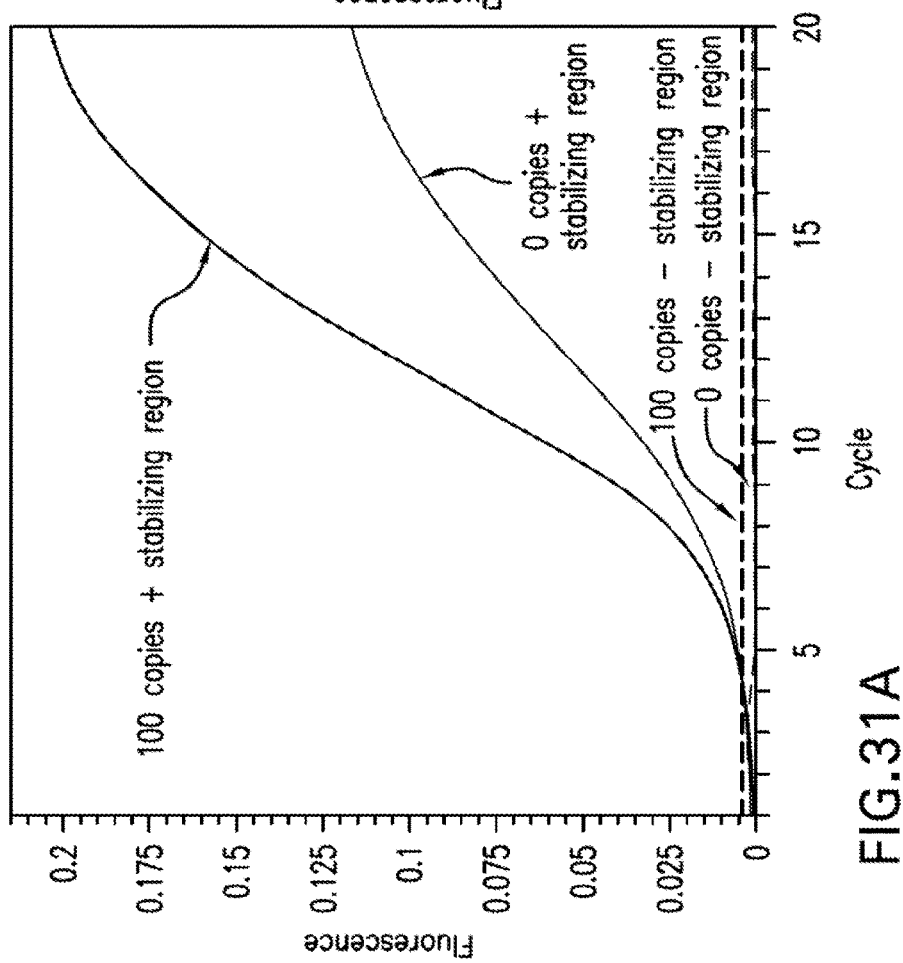
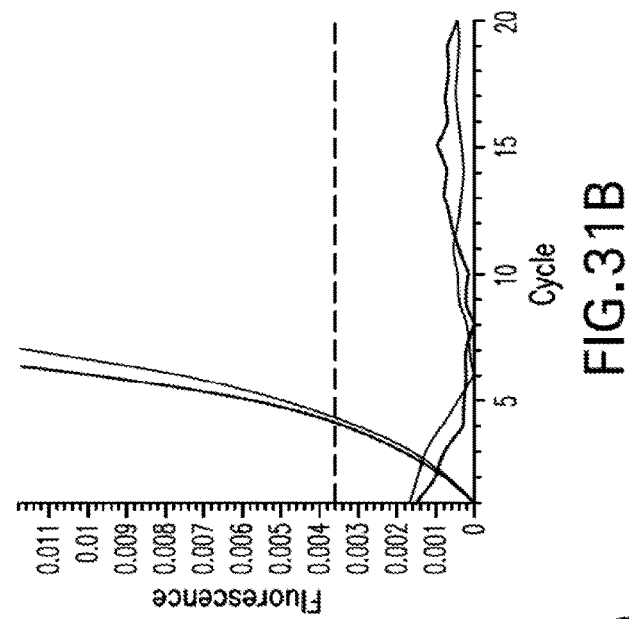
FIG. 31A
FIG. 31B

Ct NEAR assay-Mg+2[] titration

| Assay ID | Ct Ps_2 | |
|---|---|---|
| Target | Chlamydia trachomatis | |
| | synthetic | |
| MB ID/[nM] | MB5.18/400 | |
| Template ratio [nM] | 200:100 | |
| Replicates | 2 | |
| Experiment Date | 1/14/2008 | |
| Step | Time (min) | Temp (°C) |
| Reaction | 5 | 56 |
| Enzyme Inactivation | 2 | 80 |
| Readout | 1 | 56 |
| Comments: Comments: In-house buffer was used at 50mM Tris-HCl, pH8.6, 1mM DTT, 0.1% Tx-100 | | |

| Target Organism | Target | Genome | Assay |
|---|---|---|---|
| Chlamydia trachomatis | Bacteria | DNA | P2_2 |
| C trachomatis | Bacteria | RNA | P2_2 |
| Neisseria gonorrhoeae | Bacteria | DNA | 16S-4 |
| N gonorrhoeae | Bacteria | DNA | pilQ 1.6 |
| Mycobacterium tuberculosis | Bacteria | DNA | ITS.23s.5s.A.F/R1.12 |
| Enterovirus | Virus | RNA | F8/R9.11 |
| Clostridium difficile | Bacteria | DNA | TcdB F24/R25 |
| C difficile | Bacteria | DNA | TcdB F25/R25 |
| C difficile | Bacteria | DNA | TcdB F24/R24 |
| Listeria monocytogenes | Bacteria | DNA | Lmono 579 |
| Foot & Mouth disease virus | Virus | RNA | F1.2/R1.2 |
| Foot & Mouth disease virus | Virus | RNA | F1.7/R1.7 |
| Human miRNA | Eukaryote | RNA | miRNA 21 |
| Human miRNA | Eukaryote | RNA | miRNA 335 |
| Bacillus subtilis | Bacteria | DNA | ppsA 1.25 |
| B subtilis | Bacteria | RNA | ppsA 1.25 |
| Adenovirus 5 | Virus | DNA | E1A 1.11 |
| Methicillin-resistant Staphylococcus aureus | Bacteria | DNA | mecA 1359 |
| MRSA | Bacteria | DNA | mecA 1520 |
| MRSA | Bacteria | DNA | SA_nuc 355 |
| MRSA | Bacteria | DNA | SA_nuc 368 |
| MRSA | Bacteria | DNA | SA_nuc 662 |
| Salmonella spp | Bacteria | DNA | spaO 4 |
| Acinetobacter baumanii | Bacteria | DNA | A.ba.gyrB.A.12.F9/R9 |
| Escherichia coli | Bacteria | DNA | Ecoli 4.F/R |

FIG.34A

| Template (5'-3') | Template 2 (5'-3') | Target (5'-3') |
|---|---|---|
| ATCATGCATGCACATAGCTTATGGAG | ATCATCCATGCATGAGTCACATTTATACCGCTTA | AGGCTTATGGAGTTAAGCGGTATAA |
| ATCATGCATGCACATAGCTTATGGAG | ATCATCCATGCATGAGTCACATTTATACCGCTTA | AGGCTTATGGAGTTAAGCGGTATAA |
| ATCATGCATGCACATCGCATACGTCTT | ATCATCCATGCATGAGTCACATCCTGCTTTCCT | CGCATACGTCTTCGAGGGGAAACCAGG |
| ATCATGCATGCACATTTTTCGAGTCC | ATCATCCATGCATGAGTCACATACTCTACCAACA | ACTCTACCAACACGGAACTCAAAAA |
| ATCATGCATGCACATAAACAAACTCGC | ATCATCCATGCATGAGTCACATAACGGATGTGGT | AAACAAACTCCAACACACATCCGTT |
| ATCATGCATGCACATCGACTACTTTGG | ATCATCCATGCATGAGTCACATCGAAACACGGAC | CGACTACTTTGGGTGTCCGTGTTTC |
| ATCATGCATGCACATAGAAAACTGGAGA | ATCATCCATGCATGAGTCACATCTACAAATATAG | AGAAAACTGGAGAATCTATATTTGTAG |
| ATCATGCATGCACATGAAAACTGGGAC | ATCATCCATGCATGAGTCACATCTACAAATATAG | GAAAACTGGAGAATCTATATTTGTAG |
| ATCATGCATGCACATAGAAAACTGGAC | ATCATCCATGCATGAGTCACATCAAATATAGAT | AGAAACTGGAGAATCTATATTTG |
| ATCATGCATGCACATAAAGCAAGAGAA | ATCATCCATGCATGAGTCACATATATAACCGATAAC | AAACAAGAGAAAGTATGCGTGTAT |
| ATCATGCATGCACATAGCCTAAGGATG | ATCATCCATGCATGAGTCACATGGTACCTGAAGG | AGGCTAAGGATGCCCTTCAGGTACC |
| ATCATGCATGCACATGCCCTTCAGGTA | ATCATCCATGCATGAGTCACATTGTTACCTGGGG | GCCCTTCAGGTACCCGAGTAACA |
| ATCATGCATGCACATTACCTTATCA | ATCATCCATGCATGAGTCACATTCAACATCAG | UACCUAUCACACUGCAUCUUGA |
| ATCATGCATGCACATTCAAGAGCAA | ATCATCCATGCATGAGTCACATACATTTTTCGT | UCAAGAGCAAUAACUGAAAAAUGU |
| ATCATGCATGCACATCCAAGCTCAAAA | ATCATCCATGCATGAGTCACATTTCAGGATTCCT | CCAAGCTCAAAAAGAATCGTGAA |
| ATCATGCATGCACATCCAAGCTCAAAA | ATCATCCATGCATGAGTCACATGTACCTGAAGG | CCAAGCTCAAAAAGAATCGTGAA |
| ATCATGCATGCACATCAACACCTACC | ATCATCCATGCATGAGTCACATTAGCGACGGC | CAACACCTACCCGCCGGTCCTAAA |
| ATCATGCATGCACATGATACCTTGGTT | ATCATCCATGCATGAGTCACATGATACCTTGTT | GATACCTTGGTTCCACTTAAACCCG |
| ATCATGCATGCACATGCCAATTCCACA | ATCATCCATGCATGAGTCACATAGACCGAAACA | GCCAATTCCACATTGTTTCGGTCTA |
| ATCATGCATGCACATGAAATGACCTAA | ATCATCCATGCATGAGTCACATTAGGATGCTTTG | GATACCGTGAAACAAAGCATCCTA |
| ATCATGCATGCACATCAAAAGCATCTA | ATCATCCATGCATGAGTCACATCTCTACACCTTT | CAAAGCATCCTAAAAAAGGTGTAGA |
| ATCATGCATGCACATCAACACCGCTG | ATCATCCATGCATGAGTCACATATTGACCTGAA | AAGACAACCCTGATTCAGGTCAATA |
| ATCATGCATGCACATAGAAATGACCTAA | ATCATCCATGCATGAGTCACATTACGCGAAAAA | GAAATGACCTAACTTTTTCGCGTAG |
| ATCATGCATGCACATAAATTCTCGTCT | ATCATCCATGCATGAGTCACATTTCTTTGTCT | AAATTCTCGTCTCAGAACAAAGAAA |
| ATGCATGCATGCACATAGTTTCGACTGT | ATCATCCATGCATGAGTCACATGTTAAGCAGGAA | AGTTTCGACTGTTTTCCTGCTTAAC |

FIG. 34B

```
                       SEQUENCE LISTING

<160> NUMBER OF SEQ ID NOS: 99

<210> SEQ ID NO 1
<211> LENGTH: 25
<212> TYPE: DNA
<213> ORGANISM: Bacillus subtilis

<400> SEQUENCE: 1
ttaacgtctc taatttcagc ttttg                                          25

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atgcatgcat gagtcacatt taacgtctct a                                   31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgcatgcat gagtcacatc aaaagctgaa a                                   31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgcatgcat gagtcacata ggcttatgga g                                   31

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgcatgcat gagtcacatt tataccgctt a                                   31
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctggctaccg cttaactcca taagccag                                          28

<210> SEQ ID NO 7
<211> LENGTH: 25
<212> TYPE: DNA
<213> ORGANISM: Chlamydia trachomatis

<400> SEQUENCE: 7
aggcttatgg agttaagcgg tataa                                             25

<210> SEQ ID NO 8
<211> LENGTH: 25
<212> TYPE: DNA
<213> ORGANISM: Listeria monocytogenes

<400> SEQUENCE: 8
aaagcaagag aaagttatcg tgtat                                             25

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgcatgcat gagtcacata aagcaagaga a                                      31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgcatgcat gagtcacata tacacgataa c                                      31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atgcatgcat gagtcacatc atcgtcaacc a                                      31

<210> SEQ ID NO 12
<211> LENGTH: 31
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 12
atgcatgcat gagtcacatt gtctcgatgt a                                         31

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catcgtcaac cactacatcg agaca                                                25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgtctcgatg tagtggttga cgatg                                                25

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cctcgccgtc aaccactaca tcgagcgagg                                           30

<210> SEQ ID NO 16
<211> LENGTH: 22
<212> TYPE: RNA
<213> ORGANISM: Homo sapiens

<400> SEQUENCE: 16
uagcuuauca gacugauguu ga                                                   22

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
atgcatgcat gagtcacatt agcttatca                                            29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
```

```
atgcatgcat gagtcacatt caacatcag                                      29

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tagcttatca gactgatgtt ga                                             22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcaacatcag tctgataagc ta                                             22

<210> SEQ ID NO 21
<211> LENGTH: 25
<212> TYPE: DNA
<213> ORGANISM: Neisseria gonorrhoeae

<400> SEQUENCE: 21
actctaccaa cacggaactc aaaaa                                          25

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
atgcatgcat gagtcacatt ttttgagttc c                                   31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atgcatgcat gagtcacata ctctaccaac a                                   31

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgcatggagt tccgtgttgg tagacatgcg                                     30
```

```
<210> SEQ ID NO 25
<211> LENGTH: 25
<212> TYPE: DNA
<213> ORGANISM: Bacillis subtilis

<400> SEQUENCE: 25
ccaagctcaa aaaggaatc gtgaa                                          25

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atgcatgcat gagtcacatc caagctcaaa a                                  31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atgcatgcat gagtcacatt tcacgattcc t                                  31

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atgcatgcat                                                          10

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atgcatgcat gagtcacatg aggcttatgg a                                  31

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atgcatgcat gagtcacata gaggcttatg g                                  31

<210> SEQ ID NO 31
<211> LENGTH: 31
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 31
atgcatgcat gagtcacatt agaggcttat g                                 31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atgcatgcat gagtcacatt tagaggctta t                                 31

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgcatgcat gagtcacatc ttagaggctt a                                 31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgcatgcat gagtcacatt ttataccgct t                                 31

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atgcatgcat gagtcacatt tttataccgc t                                 31

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atgcatgcat gagtcacatg ttttataccg c                                 31

<210> SEQ ID NO 37
<211> LENGTH: 31
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 37
atgcatgcat gagtcacatt gttttatacc g                             31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atgcatgcat gagtcacata tgttttatac c                             31

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccatattttg tatacactga gtacgtacgt a                             31

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gccatatttt gttacactga gtacgtacgt a                             31

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgccatattt tgtacactga gtacgtacgt a                             31

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcgccatatt tttacactga gtacgtacgt a                             31

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
ttcgccatat tttacactga gtacgtacgt a                              31

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
attcgccata tttacactga gtacgtacgt a                              31

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cttagaggct tatggagtta agcggtataa aacat                          35

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gaatctccga atacctcaat tcgccatatt ttgta                          35

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atgcatgcat gagtcacatc gcatacgtct t                              31

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atgcatgcat gagtcacata aacaaactcg c                              31

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atgcatgcat gagtcacatc gactactttg g    31

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgcatgcat gagtcacata gaaactggag a    31

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atgcatgcat gagtcacatg aaactggaga a    31

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atgcatgcat gagtcacata gaaactggag    30

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atgcatgcat gagtcacata ggctaaggat g    31

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atgcatgcat gagtcacatg cccttcaggt a    31

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 55
atgcatgcat gagtcacatt caagagcaa                                    29

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
atgcatgcat gagtcacatc aagacctacc                                   30

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atgcatgcat gagtcacatc ggttttaagt g                                 31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
atgcatgcat gagtcacatg ccaattccac a                                 31

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
atgcatgcat gagtcacatg atacacctga a                                 31

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
atgcatgcat gagtcacatc aaagcatcct a                                 31

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
```
atgcatgcat gagtcacata agacaacgct g                                              31

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atgcatgcat gagtcacatg aaatgaccta a                                              31

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atgcatgcat gagtcacata aattctcgtc t                                              31

<210> SEQ ID NO 64
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atgcatgcat gagtcacata gtttcgactg t                                              31

<210> SEQ ID NO 65
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atgcatgcat gagtcacatc ctgctttccc t                                              31

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
atgcatgcat gagtcacata acggatgtgg t                                              31

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atgcatgcat gagtcacatg aaacacggac                                    30

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
atgcatgcat gagtcacatc tacaaatata g                                  31

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atgcatgcat gagtcacatc aaatatagat                                    30

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
atgcatgcat gagtcacatg gtacctgaag g                                  31

<210> SEQ ID NO 71
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atgcatgcat gagtcacatt gttacctcgg g                                  31

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atgcatgcat gagtcacata cattttcgt                                     30

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atgcatgcat gagtcacatt ttaggacggc                                    30

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atgcatgcat gagtcacatg ataccttcgt t                                   31

<210> SEQ ID NO 75
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atgcatgcat gagtcacatt agaccgaaac a                                   31

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
atgcatgcat gagtcacatt aggatgcttt g                                   31

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atgcatgcat gagtcacatt ctacacctttt t                                  31

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
atgcatgcat gagtcacatt attgacctga a                                   31

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
atgcatgcat gagtcacatc tacgcgaaaa a                                   31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
atgcatgcat gagtcacatt ttcttttgtc t                            31

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
atgcatgcat gagtcacatg ttaagcagga a                            31

<210> SEQ ID NO 82
<211> LENGTH: 27
<212> TYPE: DNA
<213> ORGANISM: Neisseria gonorrhoeae

<400> SEQUENCE: 82
cgcatacgtc ttgagaggga aagcagg                                 27

<210> SEQ ID NO 83
<211> LENGTH: 25
<212> TYPE: DNA
<213> ORGANISM: Mycobacterium tuberculosis

<400> SEQUENCE: 83
aaacaaactc gcaaccacat ccgtt                                   25

<210> SEQ ID NO 84
<211> LENGTH: 25
<212> TYPE: DNA
<213> ORGANISM: Enterovirus

<400> SEQUENCE: 84
cgactacttt gggtgtccgt gtttc                                   25

<210> SEQ ID NO 85
<211> LENGTH: 26
<212> TYPE: DNA
<213> ORGANISM: Clostridium difficile

<400> SEQUENCE: 85
agaaactgga gaatctatat ttgtag                                  26

<210> SEQ ID NO 86
<211> LENGTH: 25
<212> TYPE: DNA
<213> ORGANISM: Clostridium difficile

<400> SEQUENCE: 86
gaaactggag aatctatatt tgtag                                   25

<210> SEQ ID NO 87
<211> LENGTH: 23

```
<212> TYPE: DNA
<213> ORGANISM: Clostridium difficile

<400> SEQUENCE: 87
agaaactgga gaatctatat ttg                                          23

<210> SEQ ID NO 88
<211> LENGTH: 25
<212> TYPE: DNA
<213> ORGANISM: Foot and Mouth Disease Virus

<400> SEQUENCE: 88
aggctaagga tgcccttcag gtacc                                        25

<210> SEQ ID NO 89
<211> LENGTH: 25
<212> TYPE: DNA
<213> ORGANISM: Foot and Mouth Disease Virus

<400> SEQUENCE: 89
gcccttcagg taccccgagg taaca                                        25

<210> SEQ ID NO 90
<211> LENGTH: 23
<212> TYPE: RNA
<213> ORGANISM: Homo sapiens

<400> SEQUENCE: 90
ucaagagcaa uaacgaaaaa ugu                                          23

<210> SEQ ID NO 91
<211> LENGTH: 23
<212> TYPE: DNA
<213> ORGANISM: Adenovirus 5

<400> SEQUENCE: 91
caagacctac ccgccgtcct aaa                                          23

<210> SEQ ID NO 92
<211> LENGTH: 25
<212> TYPE: DNA
<213> ORGANISM: Staphylococcus aureus

<400> SEQUENCE: 92
gataccttcg ttccacttaa aaccg                                        25

<210> SEQ ID NO 93
<211> LENGTH: 25
<212> TYPE: DNA
<213> ORGANISM: Staphylococcus aureus

<400> SEQUENCE: 93
gccaattcca cattgtttcg gtcta                                        25

<210> SEQ ID NO 94
<211> LENGTH: 25
<212> TYPE: DNA
<213> ORGANISM: Staphylococcus aureus

<400> SEQUENCE: 94
gatacacctg aaacaaagca tccta                                        25

<210> SEQ ID NO 95
```

```
<211> LENGTH: 25
<212> TYPE: DNA
<213> ORGANISM: Staphylococcus aureus

<400> SEQUENCE: 95
caaagcatcc taaaaaggt gtaga                                            25

<210> SEQ ID NO 96
<211> LENGTH: 25
<212> TYPE: DNA
<213> ORGANISM: Staphylococcus aureus

<400> SEQUENCE: 96
aagacaacgc tgattcaggt caata                                           25

<210> SEQ ID NO 97
<211> LENGTH: 25
<212> TYPE: DNA
<213> ORGANISM: Salmonella sp.

<400> SEQUENCE: 97
gaaatgacct aactttttcg cgtag                                           25

<210> SEQ ID NO 98
<211> LENGTH: 25
<212> TYPE: DNA
<213> ORGANISM: Acinetobacter baumanii

<400> SEQUENCE: 98
aaattctcgt ctcagacaaa agaaa                                           25

<210> SEQ ID NO 99
<211> LENGTH: 25
<212> TYPE: DNA
<213> ORGANISM: Escherichia coli

<400> SEQUENCE: 99
agtttcgact gttttcctgc ttaac                                           25
```

NICKING AND EXTENSION AMPLIFICATION REACTION FOR THE EXPONENTIAL AMPLIFICATION OF NUCLEIC ACIDS

RELATED APPLICATIONS

Priority is claimed to U.S. patent application Ser. No. 11/778,018, filed Jul. 14, 2007, and entitled Nicking and Extension Amplification Reaction for the Exponential Amplification of Nucleic Acids, which is referred to and incorporated herein by reference in its entirety.

FIELD OF THE INVENTION

The invention is in general directed to the rapid exponential amplification of short DNA or RNA sequences at a constant temperature.

BACKGROUND

The field of in vitro diagnostics is quickly expanding as the need for systems that can rapidly detect the presence of harmful species or determine the genetic sequence of a region of interest is increasing exponentially. Current molecular diagnostics focus on the detection of biomarkers and include small molecule detection, immuno-based assays, and nucleic acid tests. The built-in specificity between two complementary or substantially complementary nucleic acid strands allows for fast and specific recognition using unique DNA or RNA sequences, the simplicity of which makes a nucleic acid test an attractive prospect. Identification of bacterial and viral threat agents, genetically modified food products, and single nucleotide polymorphisms for disease management are only a few areas where the advancement of these molecular diagnostic tools becomes extremely advantageous. To meet these growing needs, nucleic acid amplification technologies have been developed and tailored to these needs of specificity and sensitivity.

Historically, the most common amplification technique is the polymerase chain reaction (PCR), which has in many cases become the gold standard for detection methods because of its reliability and specificity. This technique requires the cycling of temperatures to proceed through the steps of denaturation of the dsDNA, annealing of short oligonucleotide primers, and extension of the primer along the template by a thermostable polymerase. Though many new advances in engineering have successfully shortened these reaction times to 20-30 minutes, there is still a steep power requirement to meet the needs of these thermocycling units.

Various isothermal amplification techniques have been developed to circumvent the need for temperature cycling. From this demand, both DNA and RNA isothermal amplification technologies have emerged.

Transcription-Mediated Amplification (TMA) employs a reverse transcriptase with RNase activity, an RNA polymerase, and primers with a promoter sequence at the 5' end. The reverse transcriptase synthesizes cDNA from the primer, degrades the RNA target, and synthesizes the second strand after the reverse primer binds. RNA polymerase then binds to the promoter region of the dsDNA and transcribes new RNA transcripts which can serve as templates for further reverse transcription. The reaction can produce a billion fold amplification in 20-30 minutes. This system is not as robust as other DNA amplification techniques and is therefore, not a field-deployable test due to the ubiquitous presence of RNAases outside of a sterile laboratory. This amplification technique is very similar to Self-Sustained Sequence Replication (3SR) and Nucleic Acid Sequence Based Amplification (NASBA), but varies in the enzymes employed.

Single Primer Isothermal Amplification (SPIA) also involves multiple polymerases and RNaseH. First, a reverse transcriptase extends a chimeric primer along an RNA target. RNaseH degrades the RNA target and allows a DNA polymerase to synthesize the second strand of cDNA. RNaseH then degrades a portion of the chimeric primer to release a portion of the cDNA and open a binding site for the next chimeric primer to bind and the amplification process proceeds through the cycle again. The linear amplification system can amplify very low levels of RNA target in roughly 3.5 hrs.

The Q-Beta replicase system is a probe amplification method. A probe region complementary or substantially complementary to the target of choice is inserted into MDV-1 RNA, a naturally occurring template for Q-Beta replicase. Q-Beta replicates the MDV-1 plasmid so that the synthesized product is itself a template for Q-Beta replicase, resulting in exponential amplification as long as the there is excess replicase to template. Because the Q-Beta replication process is so sensitive and can amplify whether the target is present or not, multiple wash steps are required to purge the sample of non-specifically bound replication plasmids. The exponential amplification takes approximately 30 minutes; however, the total time including all wash steps is approximately 4 hours.

Numerous isothermal DNA amplification technologies have been developed as well. Rolling circle amplification (RCA) was developed based on the natural replication of plasmids and viruses. A primer extends along a circular template resulting in the synthesis of a single-stranded tandem repeat. Capture, washing, and ligation steps are necessary to preferentially circularize the template in the presence of target and reduce background amplification. Ramification amplification (RAM) adds cascading primers for additional geometric amplification. This technique involves amplification of non-specifically sized strands that are either double or single-stranded.

Helicase-dependent amplification (HDA) takes advantage of a thermostable helicase (Tte-UvrD) to unwind dsDNA to create single-strands that are then available for hybridization and extension of primers by polymerase. The thermostable HDA method does not require the accessory proteins that the non-thermostable HDA requires. The reaction can be performed at a single temperature, though an initial heat denaturation to bind the primers generates more product. Reaction times are reported to be over 1 hour to amplify products 70-120 base pairs in length.

Loop mediated amplification (LAMP) is a sensitive and specific isothermal amplification method that employs a thermostable polymerase with strand displacement capabilities and four or more primers. The primers are designed to anneal consecutively along the target in the forward and reverse direction. Extension of the outer primers displaces the extended inner primers to release single strands. Each primer is designed to have hairpin ends that, once displaced, snap into a hairpin to facilitate self-priming and further polymerase extension. Additional loop primers can decrease the amplification time, but complicates the reaction mixture. Overall, LAMP is a difficult amplification method to multiplex, that is, to amplify more than one target sequence at a time, although it is reported to be extremely specific due to the multiple primers that must anneal to the target to further the amplification process. Though the reaction proceeds under isothermal conditions, an initial heat denaturation step is required for double-stranded targets. Amplification proceeds in 25 to 50 minutes and yields a ladder pattern of various length products.

Strand displacement amplification (SDA) was developed by Walker et. al. in 1992. This amplification method uses two sets of primers, a strand displacing polymerase, and a restriction endonuclease. The bumper primers serve to displace the initially extended primers to create a single-strand for the next primer to bind. A restriction site is present in the 5' region of the primer. Thiol-modified nucleotides are incorporated into the synthesized products to inhibit cleavage of the synthesized strand. This modification creates a nick site on the primer side of the strand, which the polymerase can extend. This approach requires an initial heat denaturation step for double-stranded targets. The reaction is then run at a temperature below the melting temperature of the double-stranded target region. Products 60 to 100 bases in length are usually amplified in 30-45 minutes using this method.

These and other amplification methods are discussed in, for example, VanNess, J, et al., PNAS 2003. vol 100, no 8, p 4504-4509; Tan, E., et al., Anal. Chem. 2005, 77, 7984-7992; Lizard, P., et al., Nature Biotech. 1998, 6, 1197-1202; Notomi, T., et al., NAR 2000, 28, 12, e63; and Kurn, N., et al., Clin. Chem. 2005, 51:10, 1973-1981. Other references for these general amplification techniques include, for example, U.S. Pat. Nos. 7,112,423; 5,455,166; 5,712,124; 5,744,311; 5,916,779; 5,556,751; 5,733,733; 5,834,202; 5,354,668; 5,591,609; 5,614,389; 5,942,391; and U.S. patent publication numbers US20030082590; US20030138800; US20040058378; and US20060154286.

SUMMARY

Provided herein are methods of amplifying nucleic acid target sequences that rely on nicking and extension reactions to amplify shorter sequences in a quicker timeframe than traditional amplification reactions, such as, for example, strand displacement amplification reactions. Embodiments of the invention include, for example, reactions that use only two templates to amplify a target sequence, one or two nicking enzymes, and a polymerase, under isothermal conditions. In exemplary embodiments, the polymerase and the nicking enzyme are thermophilic, and the reaction temperature is significantly below the melting temperature of the hybridized target region. The nicking enzyme nicks only one strand in a double-stranded duplex, so that incorporation of modified nucleotides is not necessary as in the case of conventional strand displacement amplification. An initial heat denaturation step is not required for the methods of the present invention. Due to the simplicity of the reaction, in exemplary embodiments, the reaction is very easy to perform, requires no special equipment, such as a thermocycler, and can amplify 20-30mer products $10^8$ to $10^{10}$ fold from genomic DNA in only about 2.5 to about 10 minutes. Furthermore, in other exemplary embodiments, the method is able to amplify RNA without a separate reverse transcription step.

Thus, provided in a first embodiment of the present invention is a method for amplifying a double-stranded nucleic acid target sequence, comprising contacting a target DNA molecule comprising a double-stranded target sequence having a sense strand and an antisense strand, with a forward template and a reverse template, wherein said forward template comprises a nucleic acid sequence comprising a recognition region at the 3' end that is complementary or substantially complementary to the 3' end of the target sequence antisense strand; a nicking enzyme binding site and a nicking site upstream of said recognition region, and a stabilizing region upstream of said nicking enzyme binding site and said nicking site; said reverse template comprises a nucleotide sequence comprising a recognition region at the 3' end that is complementary or substantially complementary to the 3' end of the target sequence sense strand, a nicking enzyme binding site and a nicking site upstream of said recognition region, and a stabilizing region upstream of said nicking enzyme binding site and said nicking site; providing a first nicking enzyme that is capable of nicking at the nicking site of said forward template, and does not nick within said target sequence; providing a second nicking enzyme that is capable of nicking at the nicking site of said reverse template and does not nick within said target sequence; and providing a DNA polymerase; under conditions wherein amplification is performed by multiple cycles of said polymerase extending said forward and reverse templates along said target sequence producing a double-stranded nicking site, and said nicking enzymes nicking at said nicking sites, producing an amplification product.

In certain embodiments of the invention, the DNA polymerase is a thermophilic polymerase. In other examples of the invention, the polymerase and said nicking enzymes are stable at temperatures up to 37° C., 42° C., 60° C., 65° C., 70° C., 75° C., 80° C., or 85° C. In certain embodiments, the polymerase is stable up to 60° C. The polymerase may, for example, be selected from the group consisting of Bst (large fragment), 9° N, Vent$_R$® (exo-) DNA Polymerase, Therminator, and Therminator II.

The nicking enzyme may, for example, nick upstream of the nicking enzyme binding site, or, in exemplary embodiments, the nicking enzyme may nick downstream of the nicking enzyme binding site. In certain embodiments, the forward and reverse templates comprise nicking sites recognized by the same nicking enzyme and said first and said second nicking enzyme are the same. The nicking enzyme may, for example, be selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, and Nt.Bpu10I.

In certain aspects of the present invention, the target sequence comprises from 1 to 5 nucleotides more than the sum of the nucleotides of said forward template recognition region and said reverse template recognition region.

The DNA molecule may be, for example, genomic DNA. The DNA molecule may be, for example, selected from the group consisting of plasmid, mitochondrial, and viral DNA. In certain embodiments, the forward template is provided at the same concentration as the reverse template. In other examples, the forward template is provided at a ratio to the reverse template at the range of ratios of 1:100 to 100:1.

In other examples of the invention, the method further comprises the use of a second polymerase. The amplification may be, for example, conducted at a constant temperature. This temperature may be, for example, between 54° C. and 60° C. As to the length of time for the reaction to take place, in certain examples, the amplification reaction is held at constant temperature for 1 to 10 minutes.

The present invention further comprises detecting the amplification product, for example, by a method selected from the group consisting of gel electrophoresis, mass spectrometry, SYBR I fluorescence, SYBR II fluorescence, SYBR Gold, Pico Green, TOTO-3, intercalating dye detection, FRET, molecular beacon detection, surface capture, capillary electrophoresis, incorporation of labeled nucleotides to allow detection by capture, fluorescence polarization, and lateral flow capture. The amplification products may be, for example, detected using a solid surface method, for example, where at least one capture probe is immobilized on the solid surface that binds to the amplified sequence.

The present invention may be used for multiplex amplification. Thus, for example, in certain embodiments of the present invention at least two target sequences are capable of being amplified. By "capable of being amplified" is meant the amplification reaction comprises the appropriate templates and enzymes to amplify at least two target sequences. Thus, for example, the amplification reaction may be prepared to detect at least two target sequences, but only one of the target sequences may actually be present in the sample being tested, such that both sequences are capable of being amplified, even though only one sequence may actually be amplified. Or, where two target sequences are present, the amplification reaction may result in the amplification of both of the target sequences. The multiplex amplification reaction may result in the amplification of one, some, or all, of the target sequences for which it comprises the appropriate templates and enzymes.

At least one of the templates, for example, may comprise a spacer, a blocking group, or a modified nucleotide.

Also provided as an embodiment of the present invention is a method for amplifying a single-stranded nucleic acid target sequence, comprising contacting a target nucleic acid comprising a single-stranded target sequence with a reverse template, wherein said reverse template comprises a nucleotide sequence comprising a recognition region at the 3' end that is complementary or substantially complementary to the 3' end of the target sequence, a nicking enzyme binding site and a nicking site upstream of said recognition region, and a stabilizing region upstream of said nicking enzyme binding site and said nicking site; providing a first nicking enzyme that is capable of nicking at the nicking site of said reverse template, and does not nick within said target sequence; providing a DNA polymerase under conditions wherein said polymerase extends said reverse template along said target sequence; contacting said extended reverse template with a forward template, wherein said forward template comprises a recognition region at the 3' end that is identical to the 5' end of the target sequence a nicking enzyme binding site and a nicking site upstream of said recognition region, and a stabilizing region upstream of said nicking enzyme binding site and said nicking site; providing a second nicking enzyme that is capable of nicking at the nicking site of said forward template and does not nick within said target sequence; under conditions wherein amplification is performed by multiple cycles of said polymerase extending said forward and reverse templates along said target sequence producing a double-stranded nicking site, and said nicking enzymes nicking at said nicking sites, producing an amplification product.

Those of ordinary skill in the art understand that the examples presented herein relating to the amplification of a double-stranded nucleic acid target sequence and the detection of the amplified product also apply to the amplification of a single-stranded nucleic acid target sequence and the detection of the amplified product. Furthermore, in examples of the present invention, the target sequence may be, for example, RNA, for example, but not limited to, messenger RNA (mRNA), ribosomal RNA (rRNA), viral RNA, microRNA, a microRNA precursor, or siRNA. In exemplary embodiments of the present invention, for example, where the target sequence is RNA, the polymerase has reverse transcription activity. In yet other examples of the present invention, the target sequence is DNA, such as, for example, genomic DNA, or for example, the target sequence is selected from the group consisting of plasmid, mitochondrial, and viral DNA, or even a PCR product.

Where the method, in accordance with the present invention, involves the use of more than one polymerase, in exemplary embodiments at least one of the polymerases may have reverse transcriptase activity.

In other embodiments of the present invention, a set of oligonucleotide templates is provided, comprising a first template for nucleic acid amplification, comprising a recognition region at the 3' end that is complementary or substantially complementary to the 3' end of a target sequence antisense strand; a nicking enzyme binding site and a nicking site upstream of said recognition region; and a stabilizing region upstream of said nicking enzyme binding site and said nicking site; and a second template for nucleic acid amplification, comprising a recognition region at the 3' end that is identical to the 5' of said target sequence antisense strand; nicking enzyme binding site and a nicking site upstream of said recognition region; and a stabilizing region upstream of said nicking enzyme binding site and said nicking site; wherein said target sequence comprises from 1 to 5 spacer bases between said 3' end of the antisense strand and said 5' end of said antisense strand that do not bind to either template.

In yet other embodiments, a kit is provided for following the methods of the present invention for nucleic acid amplification, comprising a DNA polymerase; a first template for nucleic acid amplification, comprising a recognition region at the 3' end that is complementary or substantially complementary to the 3' end of a target sequence antisense strand; a nicking enzyme binding site and a nicking site upstream of said recognition region; and a stabilizing region upstream of said nicking enzyme binding site and said nicking site; a second template for nucleic acid amplification, comprising a recognition region at the 3' end that is complementary or substantially complementary to the 3' end of a target sequence sense strand; nicking enzyme binding site and a nicking site upstream of said recognition region; and a stabilizing region upstream of said nicking enzyme binding site and said nicking site; one or two thermostable nicking enzymes, wherein either one enzyme is capable of nicking at the nicking site of said first and said second templates, or a first enzyme is capable of nicking at the nicking site of said first primer and a second enzyme is capable of nicking at the enzyme site of said second primer.

The kit may, for example, provide said polymerase, nicking enzymes, and templates in a container. The kit may provide, for example, said polymerase, nicking enzymes, and templates in two containers. In certain examples, the polymerase and nicking enzymes are in a first container, and said templates are in a second container. In certain examples, the polymerase and nicking enzymes are lyophilized. The kit may, for example, further comprise instructions for following the amplification methods of the present invention. The kit may, for example, further comprise a cuvette. The kit may, for example, further comprise a lateral flow device or dipstick. The lateral flow device or dipstick may, for example, further comprise a capture probe, wherein said capture probe binds to amplified product. The kit may, for example, further comprise a detector component, for example, one selected from the group consisting of a fluorescent dye, colloidal gold particles, latex particles, a molecular beacon, polystyrene beads, and the like. In other examples, at least one of the templates of the kit may comprise a spacer, blocking group, or a modified nucleotide.

Deoxynucleoside triphosphates (dNTPs) are included in the amplification reaction. One or more of the dNTPs may be modified, or labeled, as discussed herein, however, the use of modified NTPs is not required in the present method. Nucleotides are designated as follows. A ribonucleoside triphosphate is referred to as NTP or rNTP; wherein N can be A, G, C, U or m5U to denote specific ribonucleotides. Deoxynucleoside triphosphate substrates are indicated as dNTPs, wherein N can be A, G, C, T, or U. Throughout the text, monomeric nucleotide subunits may be denoted as A, G, C, or T with no particular reference to DNA or RNA.

In another embodiment, a method is provided for nucleic acid amplification comprising forming a mixture of a target nucleic acid comprising a double-stranded target sequence having a sense strand and an antisense strand; a forward template comprising a nucleic acid sequence comprising a recognition region at the 3' end that is complementary or substantially complementary to the 3' end of the target sequence antisense strand; a nicking enzyme binding site and a nicking site upstream of said recognition region, and a stabilizing region upstream of said nicking enzyme binding site and said nicking site; a reverse template comprising a nucleotide sequence comprising a recognition region at the 3' end that is complementary or substantially complementary to the 3' end of the target sequence sense strand, a nicking enzyme binding site and a nicking site upstream of said recognition region and a stabilizing region upstream of said nicking enzyme binding site and said nicking site; a first nicking enzyme that is capable of nicking at the nicking site of said forward template, and does not nick within said target sequence; a second nicking enzyme that is capable of nicking at the nicking site of said reverse template and does not nick within said target sequence; and a thermophilic polymerase under conditions wherein amplification is performed by multiple cycles of said polymerase extending said forward and reverse templates along said target sequence producing a double-stranded nicking site, and said nicking enzymes nicking at said nicking sites, producing an amplification product. In certain embodiments, the nicking enzyme binding sites on the forward and reverse templates are recognized by the same nicking enzyme, and only one nicking enzyme is used for the reaction.

In another embodiment, a method is provided for nucleic acid amplification comprising forming a mixture of a target nucleic acid comprising a single-stranded target sequence; a reverse template, wherein said reverse template comprises a nucleotide sequence comprising a recognition region at the 3' end that is complementary or substantially complementary to the 3' end of the target sequence, a nicking enzyme binding site and a nicking site upstream of said recognition region, and a stabilizing region upstream of said nicking enzyme binding site and said nicking site; a first nicking enzyme that is capable of nicking at the nicking site of said reverse template, and does not nick within said target sequence; a thermophilic polymerase under conditions wherein said polymerase extends said reverse template along said target sequence; a forward template, wherein said forward template comprises a nucleic acid sequence comprising a recognition region at the 3' end that is identical or substantially identical to the 5' end of the target sequence; and a second nicking enzyme that is capable of nicking at the nicking site of said forward template and does not nick within said target sequence; under conditions wherein amplification is performed by multiple cycles of said polymerase extending said forward and reverse templates along said target sequence producing a double-stranded nicking site, and said nicking enzymes nicking at said nicking sites, producing an amplification product. In certain embodiments, the nicking enzyme binding sites on the forward and reverse templates are recognized by the same nicking enzyme, and only one nicking enzyme is used for the reaction.

In other embodiments of the invention are provided methods for the separation of amplified nucleic acids obtained by the amplification methods of the invention. In yet further embodiments of the invention are provided methods for detecting and/or analyzing the amplified nucleic acids obtained by the amplification methods of the invention, including, for example, methods using SYBR I, II, SYBR Gold, Pico Green, TOTO-3, and most intercalating dyes, molecular beacons, FRET, surface capture using immobilized probes with fluorescence, electrochemical, or colorimetric detection, mass spectrometry, capillary electrophoresis, the incorporation of labeled nucleotides to allow detection by capture or fluorescence polarization, lateral flow, and other methods involving capture probes.

Methods using capture probes for detection include, for example, the use of a nucleic acid molecule (the capture probe) comprising a sequence that is complementary to, or substantially complementary to, an amplification product strand such that the capture probe binds to amplified nucleic acid. The probe may be linked to a detectable label in certain embodiments, and amplification product may be detected based on the detectable label of the probe specifically hybridized to the amplification product. The reaction may, for example, further comprise an antibody directed against a molecule incorporated into or attached to the capture probe. Or, for example, the capture probe, or a molecule that binds to the capture probe, may incorporate, for example, an enzyme label, for example, peroxidase, alkaline phosphatase, or beta-galactosidase, a fluorescent label, such as, for example, fluorescein or rhodamine, or, for example, other molecules having chemiluminescent or bioluminescent activity. In some embodiments, the probe is linked to a solid support, and amplification product strands may be specifically immobilized to the capture probe linked to the solid support under conditions known and selected by the person of ordinary skill in the art. In the latter embodiments, solid support-immobilized amplification product may be subjected to processing steps, such as washing, ion exchange, release from the solid support, or other processing steps. An amplification product may be detected when immobilized to a solid support in some embodiments. The embodiments of the present invention also comprise combinations of these detection and analysis methods.

BRIEF DESCRIPTION OF THE DRAWINGS

FIG. 1D is a legend for FIG. 1.

A reaction following the present methods was run for 2.5 minutes at 56° C., then heat denatured at 94° C. for 4 minutes. Six microliters of the reaction was run on a 20% polyacrylamide gel at 160V for ~2.5 hrs. The gel was stained with SYBR II gel stain. Lane 1: no target control for 25mer assay. Lane 2: no target control for 27mer assay. Lane 3: for 25mer assay with 3.5E+5 copies of genomic *Bacillus subtilis* DNA. Lane 4: for 27mer assay with 1.1E+6 copies of genomic *Bacillus subtilis* DNA.

Figure 3:
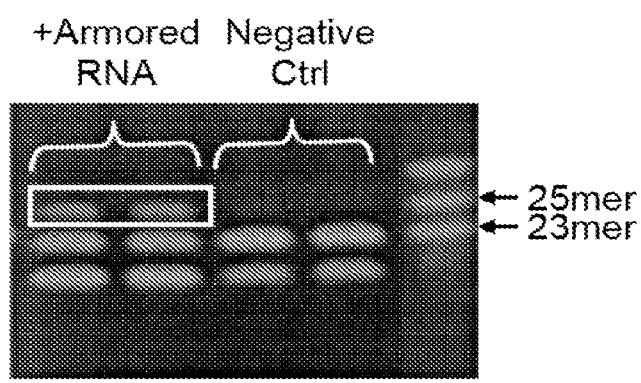

FIG. 3. 20% polyacrylamide gel of reaction products from an RNA assay using the present methods.

Figure 17:
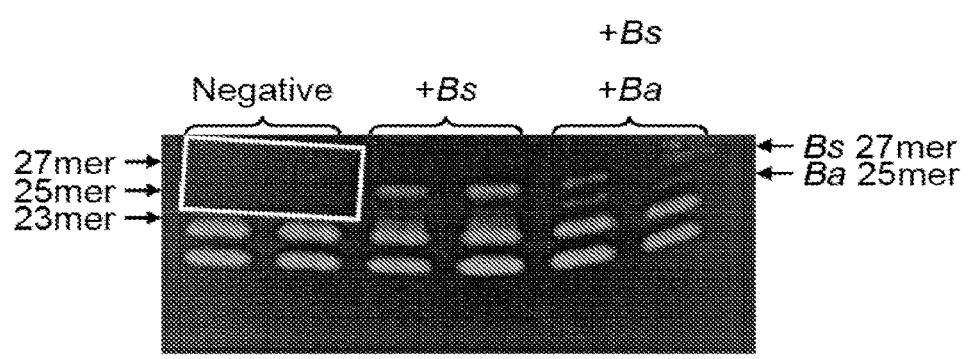

The reaction was run for 12 minutes at 56° C., then heat denatured at 94° C. for 4 minutes. Six microliters of the reaction was run on a 20% polyacrylamide gel at 160V for about 2.5 hrs. The gel was stained with SYBR II gel stain. Lane 1 and 2: reaction for 25mer assay with 1E+6 copies of Ebola Armored RNA (Ambion). Lane 3 and 4: reaction no target control for 25mer assay. 25mer reaction products are outlined in the white box.

FIG. 4. Mass Spectrum of *Bacillus anthracis* DNA assay products.

A) 0 copies of target or B) 5E+5 copies of genomic DNA added to the reaction. The reaction was run for 10 minutes, then heat denatured at 94° C. for 4 minutes. Ten microliters of sample was injected into the LC/ESI-MS. The (−4) charge state of the 26mer product and its complementary sequence are outlined in a black box. The smaller adjacent peaks are the sodium adducts of the main product.

FIG. 5. Mass Spectrum of MS2 genomic RNA assay products.

A) 0 copies of target, B) 1E+6 copies of MS2 genomic RNA, or C) 1E+6 copies of synthetic target DNA added to the reaction. The reaction was run for 10 minutes, then heat denatured at 94° C. for 4 minutes. Ten microliters of sample was injected into the LC/ESI-MS. The (−4) charge state of the 27mer product and its complement sequence are outlined in a black box. The smaller adjacent peaks are the sodium adducts of the main product.

FIG. 6. Real-time detection of amplification using intercalating fluorescent dyes.

Real-time amplification of *Yersinia pestis* genomic DNA at 500 copies (squares) compared to the no target control (NTC, open triangles). The reaction was run for 10 minutes at 58° C. and monitored by the real-time fluorescence with SYBR II (n=5).

FIG. 7. Real-time detection of amplification using fluorescence resonance energy transfer (FRET).

Real-time amplification of *Yersinia pestis* synthetic DNA at 10,000 copies (squares) compared to the no target control (NTC, open triangles). The reaction was run for 10 minutes at 57° C., n=3.

FIG. 8. *Francisella tularensis* DNA amplification detected in real-time using molecular beacons.

Either 0 copies (open triangles) or 1E+5 copies (squares) were added to the reaction mix and run for 10 minutes at 57.5° C.

FIG. 9. False positive rate testing results comparing average AUC values.

Error bars denote one standard deviation. *Bacillus subtilis* assays were run for 10 min at 55° C. in the presence and absence of *Bacillus subtilis* genomic DNA. Enzymes were heat denatured at 94° C. for 4 min. A 10 μL sample was injected into the LC/ESI-MS and the area under the curve (AUC) of the product peaks were analyzed. True Positives contained 10,000 copies of *Bacillus subtilis* DNA along with 990,000 copies of near neighbor (*Bacillus thuringiensis*) DNA. True Negatives contained 10,000 copies of *E. coli* DNA with 990,000 copies of near neighbor DNA, and water negatives contained no DNA as a control.

FIG. 10. Replication study using molecular beacon detection with different operators performing the experiments on two different days.

The reaction was run for 10 minutes at 57.5° C. (in the presence and absence of 500 copies of *Francisella tularensis* genomic DNA) with a 4 min heat kill at 94° C. 300 nM molecular beacon was added and monitored at 45, 50, and 57° C. (n=24).

FIG. 11. Sensitivity of the reaction using molecular beacon detection.

The assay was run for 10 minutes 57.5° C. The reaction was stopped with a 4 min heat inactivation step at 94° C. 300 nM molecular beacon was added and the fluorescence was monitored at 57.5° C. (n=3). Fluorescence was monitored for beacon opening in the presence of reactions amplified with 1E+6, 5E+5, 5E+4, 5E+2, 50, and 0 (NTC) input copies of *Francisella tularensis* genomic DNA, and compared to the background fluorescence of the beacon alone (MB).

FIG. 12. Final concentration of amplified products in the NEAR reaction.

The NEAR™ reaction was run for 10 min at 55° C. with varying copies of *Bacillus subtilis* genomic DNA. The reaction was stopped with a heat inactivation step at 94° C. for 4 minutes. A 10 microliter sample was injected into the LC/ESI-MS and the AUC of the product peak at 1944 Daltons was analyzed and compared to a standard curve.

FIG. 13. Correlation of the input RNA target copy number to the final concentration of amplified products.

The Ebola NEAR™ assay was run for 12 min at 55° C. with varying copies of synthetic RNA corresponding to the Ebola genome DNA. The reaction was stopped with a heat inactivation step at 94° C. for 4 minutes. A 10 microliter sample was injected into the LC/ESI-MS and the AUC of the product peak at 1936 Daltons was analyzed and compared to the standard curve of AUC values. (n=3)

FIG. 14. Mass spec product analysis demonstrating NEAR reaction specificity.

The *Bacillus anthracis* NEAR™ reaction was run in the presence of a dilution of copies of *Bacillus thuringiensis* for 10 min at 56° C. (n=3), then heat denatured at 94° C. for 4 minutes. A 10 μL sample was injected into the LC/ESI-MS and AUC values of product peaks analyzed.

FIG. 15. The effect of an interferent panel on amplification.

*Bacillus subtilis* DNA reactions were run for 10 min at 55° C. and heated to 94° C. for 4 minutes to stop the reaction. Reactions were run in triplicate in the presence 1E+5 copies of *Bacillus subtilis* genomic DNA ("_1E+5") or with no target DNA present ("_0"). Sample x is the control assay with no interferent added. Interferents A through F were added at 50% reaction volume to the *Bacillus subtilis* assay. The AUC of mass spec product peaks were analyzed using a two-way ANOVA and Bonferroni t-test. (Key: A=none; B=House dust, skim milk; C=AZ test dust, humic acid; D=Diesel soot; E=Skim milk; F=Mold spores)

FIG. 16. Gel electrophoresis results for the *Bacillus subtilis/Bacillus anthracis* DNA duplex reaction.

The NEAR™ reaction including templates specific for both *Bacillus subtilis* (Bs) and *Bacillus anthracis* (Ba) DNA was run in the absence of target DNA (negative), in the presence of *Bacillus subtilis* only (positive for 27mer product), and in the presence of both *Bacillus subtilis* and *Bacillus anthracis* (positive for 27mer and 25mer product respectively). The target copy number used in this assay was 500,000 copies. The assay was run for 10 min at 57° C. Templates varied in concentration between the assays to control the amplification (100 nM for *Bacillus anthracis* and 50 nM for *Bacillus subtilis*). Samples were run on a 20% polyacrylamide gel at 160 V for about 2 hours. The gel was stained with SYBR II fluorescent dye and imaged. The fluorescent bands were quantified and analyzed as the integrated optical density (IOD) (n=8).

FIG. 17. Specificity results for the *Bacillus subtilis/Bacillus anthracis* DNA duplex reaction shown by gel electrophoresis.

The NEAR™ reaction including templates for both a *Bacillus subtilis* (Bs) and *Bacillus anthracis* (Ba) DNA was run in the absence of target DNA (negative), in the presence of *Bacillus subtilis* DNA only (27mer product), and in the presence of both *Bacillus subtilis* and *Bacillus anthracis* DNA (27mer and 25mer product respectively). The target copy number for each genome present in this assay was 500,000 copies. All reactions contained 500,000 copies of *Bacillus thuringiensis* as exogenous nucleic acids. Templates varied in concentration between the assays to control the amplification. The assay was run for 10 min at 57° C., heat denatured at 94° C. for 4 min, and 6 microliters was loaded on to a 20% gel run at 160 V for about 2 hours. The gel was stained with SYBR II fluorescent dye and imaged. The fluorescent bands were quantified and analyzed as the integrated optical density (IOD).

Figure 18:
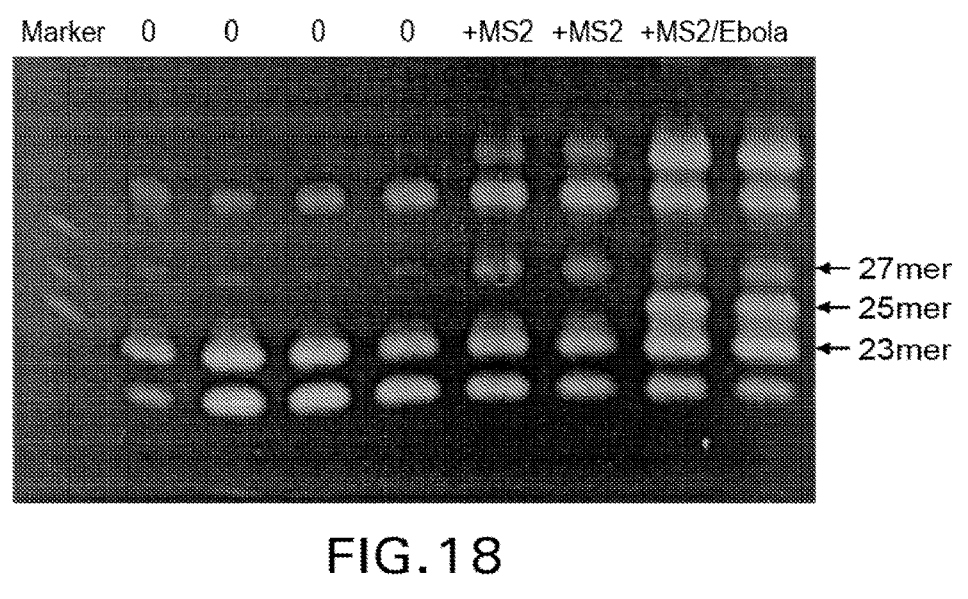

FIG. 18. Gel electrophoresis results for the MS2/Ebola RNA duplex reaction.

The NEAR™ reaction including templates for both a MS2 and Ebola assay was run in the absence of target RNA (negative, lanes 2-5), in the presence of MS2 only (27mer product, lanes 6 and 7), and in the presence of both MS2 and Ebola RNA (27mer and 25mer product respectively, lanes 8 and 9). The target copy number used in this assay was 1E+6 copies. The assay was run for 10 min at 57° C. Templates varied in concentration between the assays to control the amplification. Samples were run on a 20% polyacrylamide gel at 160 V for ~2.5 hours. The gel was stained with SYBR II fluorescent dye and imaged. The fluorescent bands were quantified and analyzed as the integrated optical density (IOD).

Figure 19:
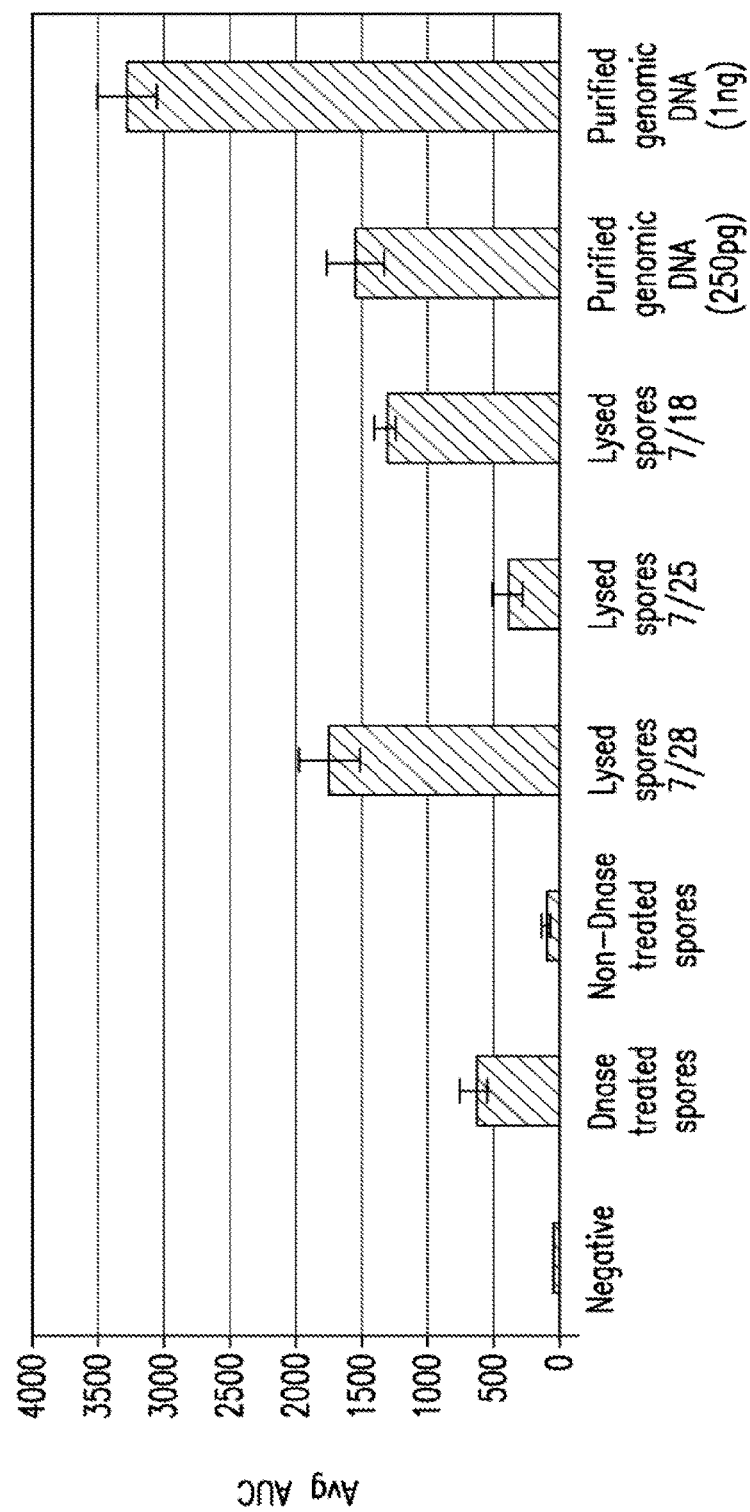

FIG. 19. Mass spec analysis of amplification of DNA from lysed spores.

Average AUC values from amplified product masses compared for lysed and unlysed samples. Lysed spore samples were then added to master mix and run for 10 minutes at 55° C., heat denatured for 4 minutes at 94° C., and run on the mass spec for analysis. AUC values of product peaks were averaged and compared (n=3).

Figure 20:
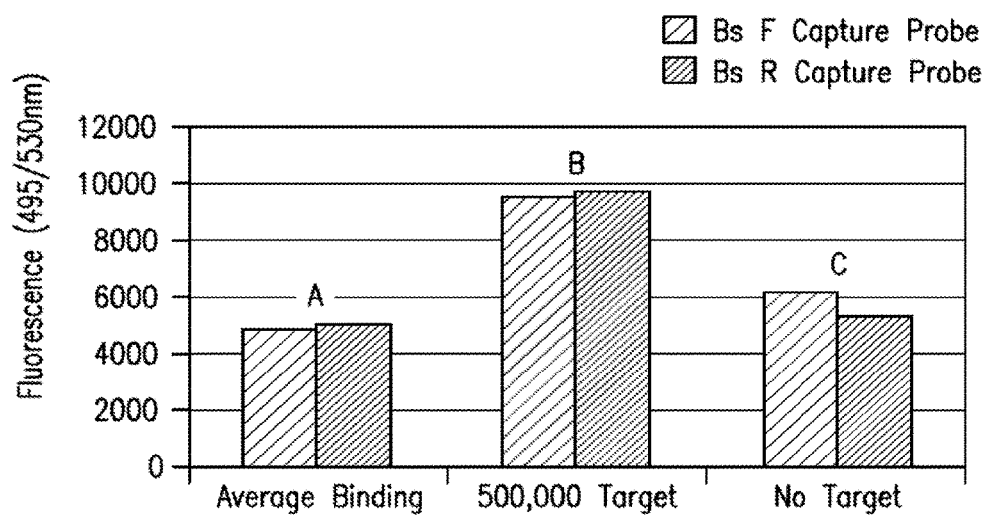

FIG. 20. Demonstration of the capture and extension approach for surface detection.

A.) Average binding (positive reaction product with no added polymerase), B.) 500,000 target (positive reaction product with added polymerase), and C.) No target (negative reaction with added polymerase) are compared. The NEAR™ assay was run for 10 minutes at 55° C., heat denatured at 94° C. for 4 minutes, then added to the plate with capture probe bound to the surface on the 5' end. Polymerase is added to one well of the positive reaction. The plate is incubated at 55° C. for 30 min, washed, SYBR II added, washed 3 times, and read on a Tecan plate reader (495 nm excitation/530 nm emission).

Figure 21:
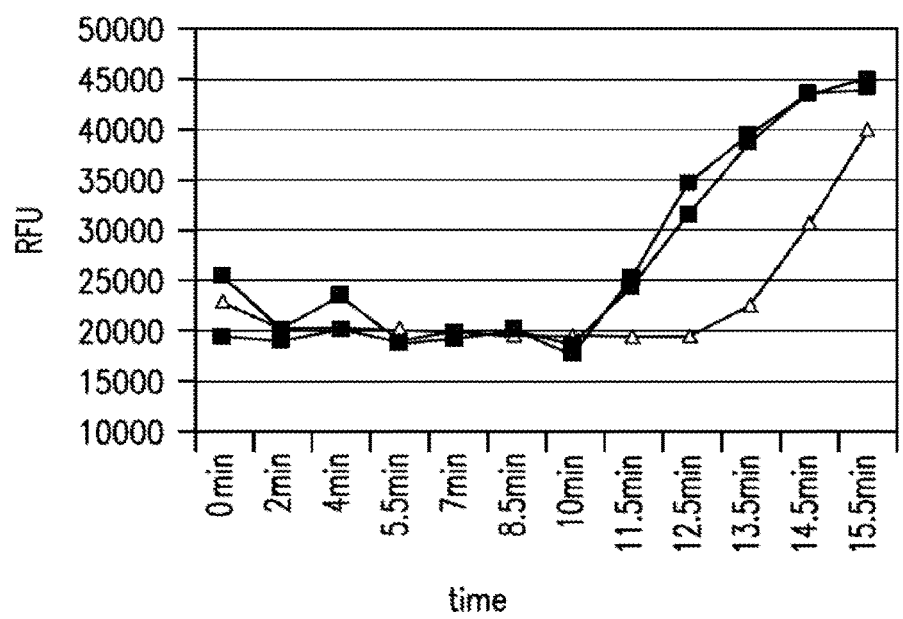

FIG. 21. Pseudo-real-time fluorescence detection of the NEAR™ FRET assay with a single template immobilized on a surface in the presence (squares) and absence (open triangles) of 1E+6 copies of genomic DNA.

Reactions were performed in flat bottom 96-well plates covered with neutravidin. A solution of 1 micromolar FRET-labeled reverse template was incubated with gentle mixing for 1 hr at 37° C. Wells were washed 3 times with a PBS-Tween solution to release unbound template. NEAR™ reaction mix of the present method was added to the wells (one for each time point taken) and incubated at 58° C. on a heating block in a shaking incubator set to 135 RPM. Time points were taken by adding 1 microliter EDTA to the well to stop the reaction. The fluorescence was read from the bottom using a Tecan 100 plate reader.

FIG. 22. Limit of Detection Assay for *Chlamydia trachomatis*. A series of assays was performed using 2-fold dilutions of *Chlamydia* target. A) Bar graph of fluorescence detection showing the limit of detection as averaged from 3 assays. B) Bar graph showing the results of individual assays.

Figure 23:
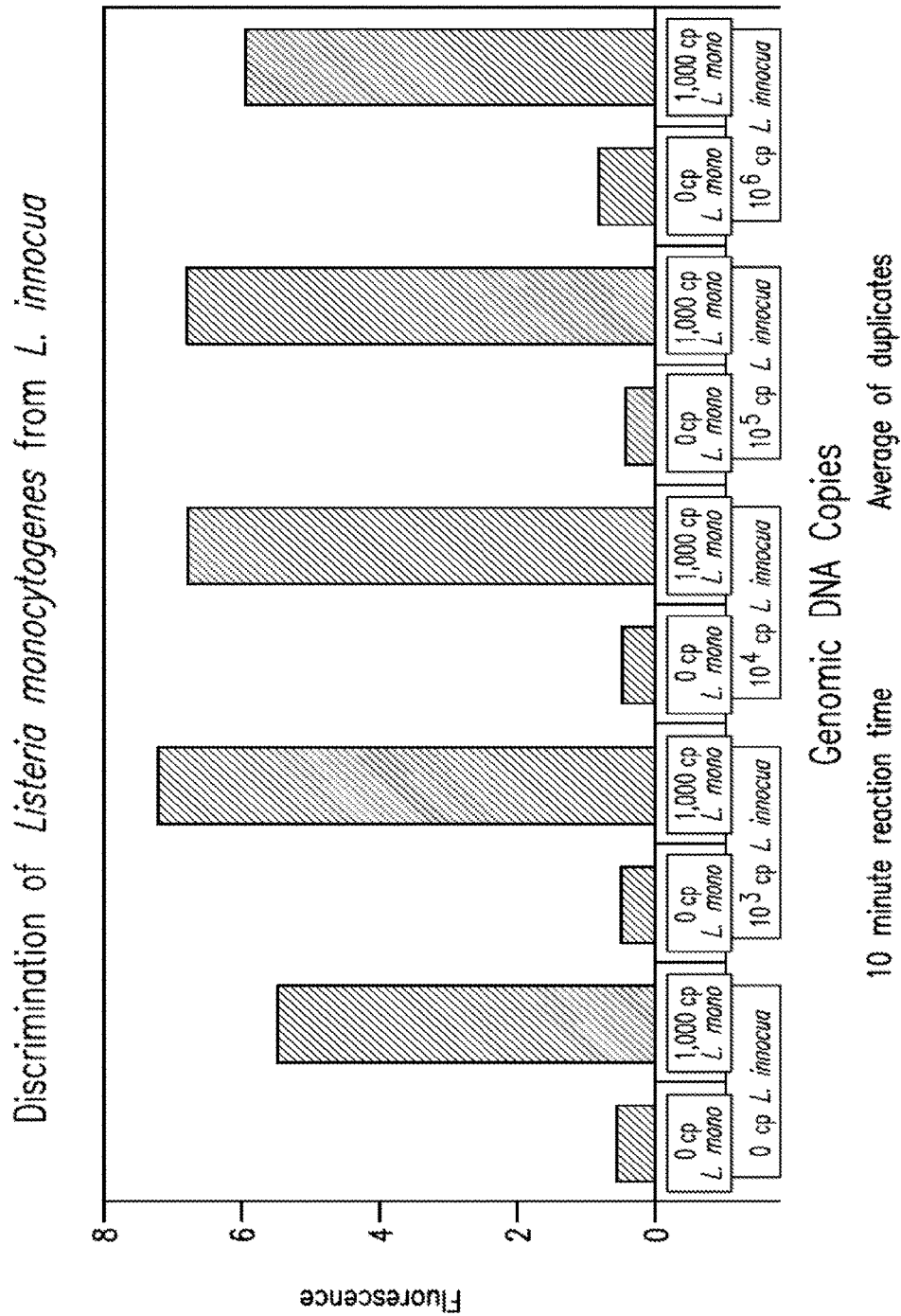

FIG. 23. Discrimination of *Listeria monocytogenes* from *L. innocua*. Bar graph showing the results of a series of assays that was performed to determine the ability of the assays to discriminate between two different bacteria.

Figure 24:
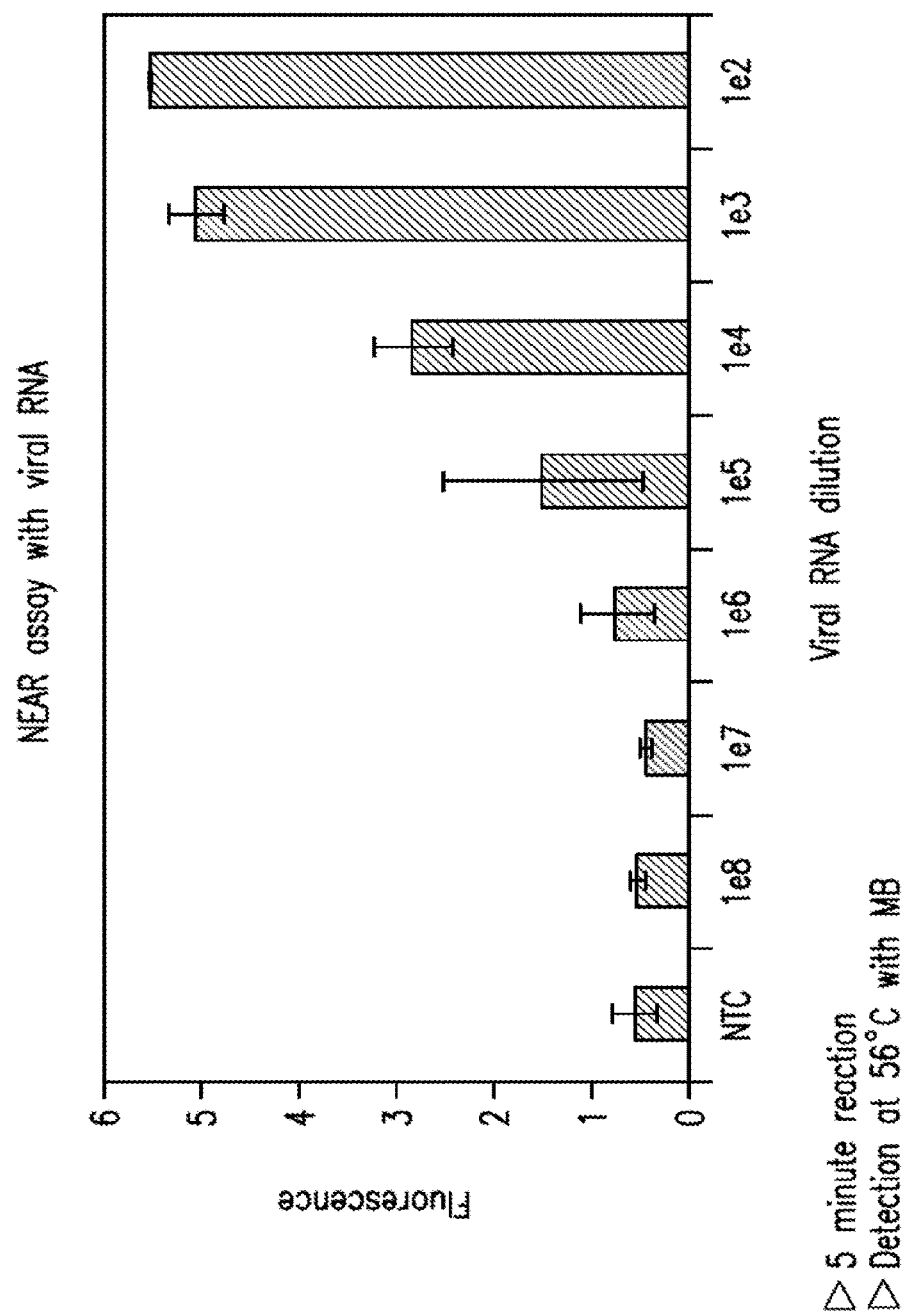

FIG. 24. Assay with Viral RNA. Bar graph showing the results of a series of assays of the present methods with various dilutions of a viral RNA target.

Figure 25:
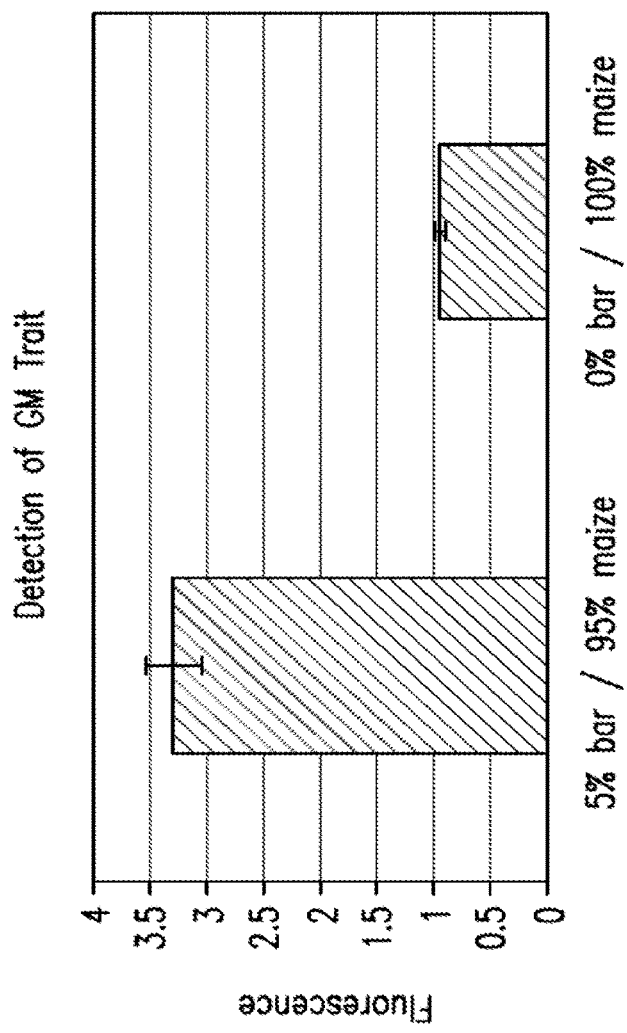

FIG. 25. Bar graph showing the results of anassay for etection of the bar gene target sequence.

Figure 26:
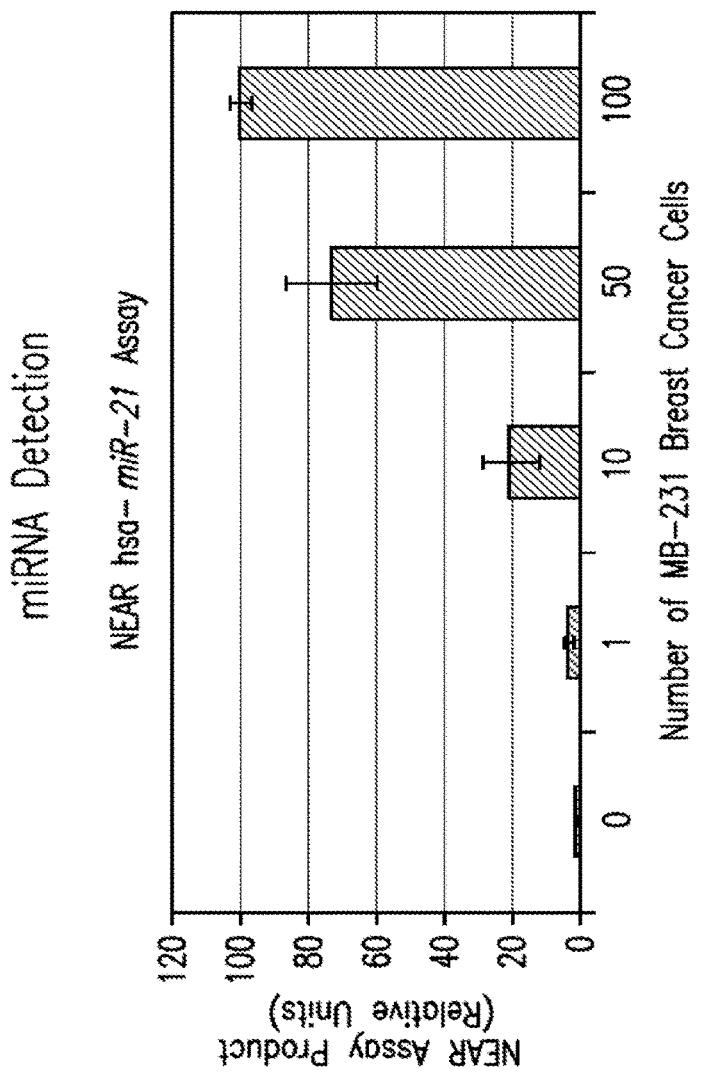

FIG. 26. Bar graph showing the results of a assay of the present methods for detection of an miRNA target sequence.

Figure 27A:
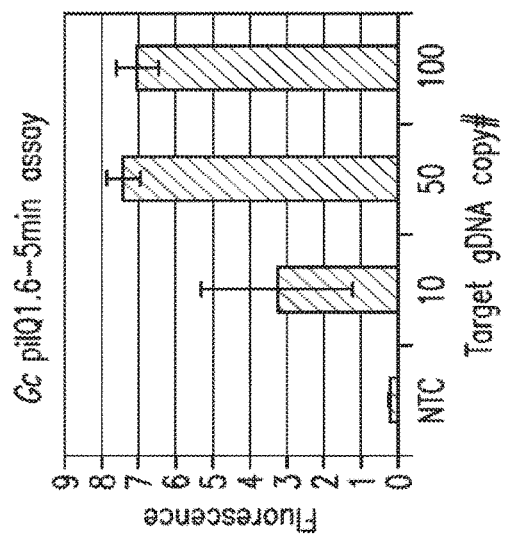
Figure 27B:
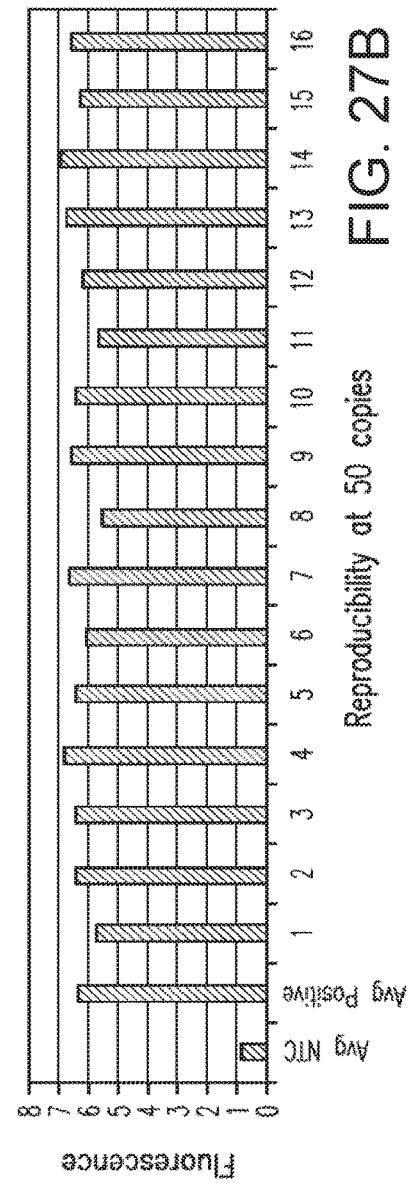

FIG. 27. Gc Assay: LOD. A) Bar graph showing the average of a series of assays for detection of a genomic target sequence. B) Results of individual assays, including 50 genomic copies each.

FIG. 28. *B. subtilis* NEAR™ assay. A) Standard curve to determine correlation between amount of reference oligonucleotide added to a sample and area under the curve (AUC). B) Bar graph showing the results of assays of the present methods to determine the amount of specific product generated. C) Table showing results of the assay.

FIG. 29. Spacer length study. A) Bar graph showing the results of an assay of the present methods to determine the effect of various spacer lengths. B) Template sequences (SEQ ID NOS 4, 29-33, 5, and 34-38,respectively in order of appearance) used to obtain different spacer lengths.

FIG. 30. Template designs used for the assay shown in FIG. 29 (SEQ ID NOS 39-46, 4, 29-33, 39, 45-46, 33, and 45, respectively in order of appearance).

FIG. 31. Effect of stabilizing region. A) Graph of the results of assays of the present methods using oligo templates that either include, or don't include, stabilizing regions. B) Expansion of part of the graph of A).

Figures 32A, 32B:
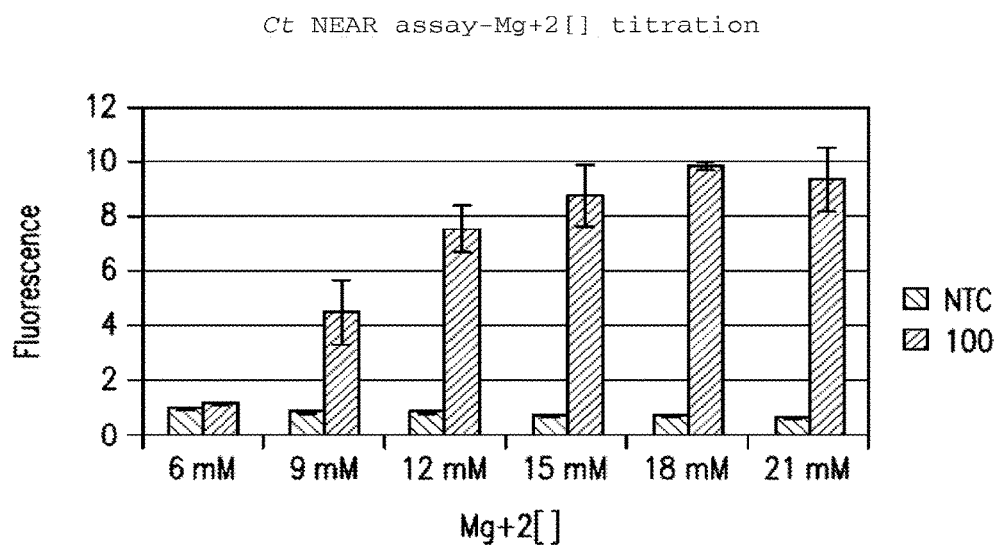

FIG. 32. Titration of $Mg^{+2}$ concentration A) Bar graph showing the results of set of NEAR assays using varying amounts of $Mg^{+2}$. B) Chart describing components of assays.

Figure 33:
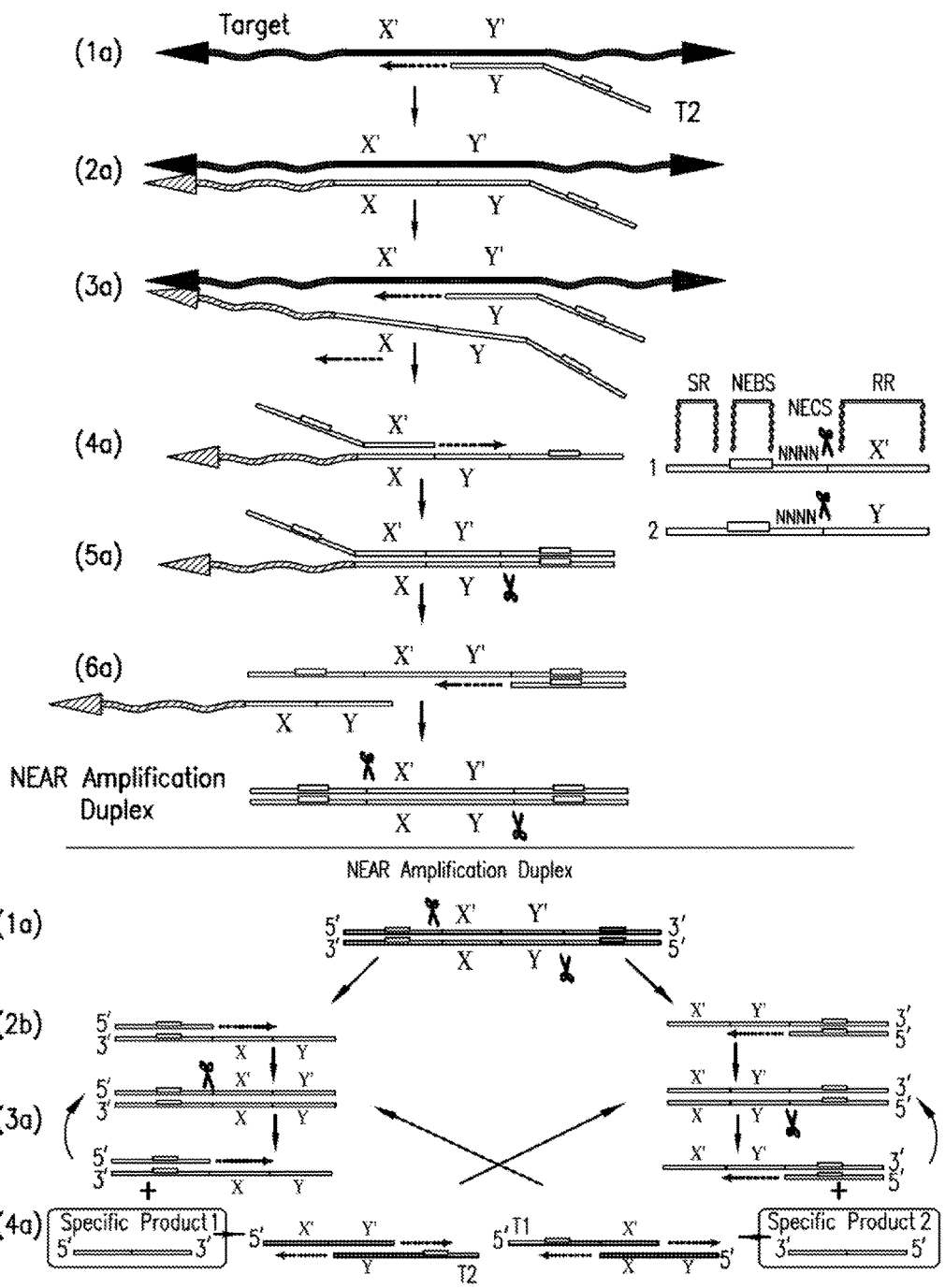

FIG. 33. Drawing depicting mechanisms of the reactions of the present methods.

FIG. 34. FIGS. 34A-34B show a list of examples of target (SEQ ID NOS 7, 7, 82, 21, 83-87, 8, 88-89, 16, 90, 25, 25, and 91-99, respectively in order of appearance in column "Target (5'-3')") and oligo template sequences (SEQ ID NOS 4, 4, 47, 22, 48-52, 9, 53-54, 17, 55, 26, 26, and 56-64, respectively in order of appearance in column "Template (5'-3')"). Template 2 sequences are disclosed as SEQ ID NOS 5, 5, 65, 23, 66-69, 10, 70-71, 18, 72, 27, 27, and 73-81, respectively in order of appearance in column "Template 2 (5'-3')".

DETAILED DESCRIPTION

Provided herein are methods for the exponential amplification of short DNA or RNA sequences.

Target nucleic acids of the present invention include double-stranded and single-stranded nucleic acid molecules. The nucleic acid may be, for example, DNA or RNA. Where the target nucleic acid is an RNA molecule, the molecule may be, for example, double-stranded, single-stranded, or the RNA molecule may comprise a target sequence that is single-stranded. Where the target nucleic acid is an RNA molecule, the molecule may be double-stranded or single-stranded, or may comprise a target sequence that is single-stranded. Target nucleic acids include, for example, genomic, plasmid, mitochondrial, cellular, and viral nucleic acid. The target nucleic acid may be, for example, genomic, chromosomal, plasmid DNA, a gene, any type of cellular RNA, or a synthetic oligonucleotide. By "genomic nucleic acid" is meant any nucleic acid from any genome, for example, including animal, plant, insect, and bacterial genomes, including, for example, genomes present in spores. Double stranded DNA target nucleic acids include, for example, genomic DNA, plasmid DNA, mitochondrial DNA, viral DNA, and synthetic double stranded DNA or other types of DNA described herein or known in the art. Single-stranded DNA target nucleic acids include, for example, viral DNA, cDNA, and synthetic single-stranded DNA, or other types of DNA described herein or known in the art. RNA target nucleic acids include, for example, messenger RNA, viral RNA, ribosomal RNA, transfer RNA, microRNA and microRNA precursors, and siRNAs or other RNAs described herein or known in the art.

MicroRNAs, miRNAs, or small temporal RNAs (stRNAs), are short single-stranded RNA sequences, about 21-23 nucleotides long that are involved in gene regulation. MicroRNAs are thought to interfere with the translation of messenger RNAs as they are partially complementary to messenger RNAs. (see, for example, Ruvkun, Gl, Science 294:797-99 (2001); Lagos-Quintana, M., et al., Science 294:854-58 (2001); Lau, N. C., et al, Science 294:858-62 (2001); Lee, R. C., and Ambros, V., Science 294:862-64 (2001); Baulcombe, D., et al., Science 297:2002-03 (2002); Llave, C., Science 297:2053-56 (2002); Hutvagner, G., and Zamore, P. D., Science 297:2056-60 (2002)). MicroRNA may also have a role in the immune system, based on studies recently reported in knock-out mice. (see, for example, Wade, N., "Studies Reveal and Immune System Regulator" New York Times, Apr. 27, 2007). MicroRNA precursors that may also be detected using the methods of the present invention include, for example, the primary transcript (pri-miRNA) and the pre-miRNA stem-loop-structured RNA that is further processed into miRNA.

Short interfering RNAs, or siRNAs are at least partially double-stranded, about 20-25 nucleotide long RNA molecules that are found to be involved in RNA interference, for example, in the down-regulation of viral replication or gene expression (see for example Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

The use of the term "target sequence" may refer to either the sense or antisense strand of the sequence, and also refers to the sequences as they exist on target nucleic acids, amplified copies, or amplification products, of the original target sequence. The amplification product may be a larger molecule that comprises the target sequence, as well as at least one other sequence, or other nucleotides. The length of the target sequence, and the guanosine:cytosine (GC) concentration (percent), is dependent on the temperature at which the reaction is run; this temperature is dependent on the stability of the polymerases and nicking enzymes used in the reaction. Those of ordinary skill in the art may run sample assays to determine the appropriate length and GC concentration for the reaction conditions. For example, where the polymerase and nicking enzyme are stable up to 60° C., then the target sequence may be, for example, from 19 to 50 nucleotides in length, or for example, from 20 to 45, 20 to 40, 22 to 35, or 23 to 32 nucleotides in length. The GC concentration under these conditions may be, for example, less than 60%, less than 55%, minutes at 56° C. with 10,000 copies of Bacillus subtilis genomic DNA plus 100,000 copies of Bacillus thuringiensis genomic DNA (True positives), 10,000 copies of Escherichia coli genomic DNA plus 100,000 Bacillus thuringiensis genomic DNA (True negatives) or no target (water control). Aliquots of each sample were then analyzed by electrospray ionization mass spectrometry to determine the amount of specific product made in each reaction using area under the curve (AUC) calculations. 50%, or less than 45%. The target sequence and nicking enzymes are selected such that the target sequence does not contain nicking sites for any nicking enzymes that will be included in the reaction mix.

The target sequences may be amplified from many types of samples including, but not limited to samples containing spores, viruses, cells, nucleic acid from prokaryotes or eukaryotes, or any free nucleic acid. For example, the assay can detect the DNA on the outside of spores without the need for lysis. The sample may be isolated from any material suspected of containing the target sequence. For example, for animals, for example, mammals, such as, for example, humans, the sample may comprise blood, bone marrow, mucus, lymph, hard tissues, for example, liver, spleen, kidney, lung, or ovary, biopsies, sputum, saliva, tears, feces, or urine. Or, the target sequence may be present in air, plant, soil, or other materials suspected of containing biological organisms.

Target sequences may be present in samples that may also contain environmental and contaminants such as dust, pollen, and soot (for example, from diesel exhaust), or clinically relevant matrices such as urine, mucus, or saliva. Target sequences may also be present in waste water, drinking water, air, milk, or other food. Depending on the concentration of these contaminants, sample purification methods known to those of ordinary skill in the art may be required to remove inhibitors for successful amplification. Purification may, for example, involve the use of detergent lysates, sonication, vortexing with glass beads, or a French press. This purification could also result in concentration of the sample target. Samples may also, for be further purified, for example, by filtration, phenol extraction, chromatography, ion exchange, gel electrophoresis, or density dependent centrifugation. In particular embodiments, the sample can be added directly to the reaction mix or pre-diluted and then added to the reaction mix without prior purification of target nucleic acid.

An oligonucleotide is a molecule comprising two or more deoxyribonucleotides or ribonucleotides, for example, more than three. The length of an oligonucleotide will depend on how it is to be used. The oligonucleotide may be derived synthetically or by cloning.

The term "complementary" as it refers to two nucleic acid sequences generally refers to the ability of the two sequences to form sufficient hydrogen bonding between the two nucleic acids to stabilize a double-stranded nucleotide sequence formed by hybridization of the two nucleic acids. In the two sequences, all nucleotides in one sequence may be complementary to counterpart nucleotides in the other sequence. In some embodiments, there may be a few mismatches between counterpart nucleotides in the two sequences (i.e., non-complementary nucleotides), such as 1 mismatch in 10 nucleotides, 1 mismatch in 20 nucleotides, or 1 mismatch in 30 nucleotides, for example, which sequences are referred to as "substantially complementary" herein. As shown in FIGS. 1A-1D, each template nucleic acid often includes a recognition region complementary to, or substantially complementary to, a target nucleic acid strand (or complement thereof) to which the template nucleic acid hybridizes. Also shown in FIGS. 1A-1D, each template nucleic acid often includes a stabilizing region 5' of the recognition region and nick agent recognition region that is not complementary or substantially complementary to the target nucleic acid sequence or complement thereof.

As used herein, "hybridization" and "binding" are used interchangeably and refer to the non-covalent binding or "base pairing" of complementary nucleic acid sequences to one another. Whether or not a particular probe remains base paired with a polynucleotide sequence depends on the degree of complementarity, the length of the probe, and the stringency of the binding conditions. The higher the stringency, the higher must be the degree of complementarity, and/or the longer the probe for binding or base pairing to remain stable.

As used herein, "stringency" refers to the combination of conditions to which nucleic acids are subjected that cause double-stranded nucleic acid to dissociate into component single strands such as pH extremes, high temperature, and salt concentration. The phrase "high stringency" refers to hybridization conditions that are sufficiently stringent or restrictive such that only specific base pairings will occur. The specificity should be sufficient to allow for the detection of unique sequences using an oligonucleotide probe or closely related sequence under standard Southern hybridization protocols (as described in J. Mol. Biol. 98:503 (1975)).

Templates are defined as oligonucleotides that bind to a recognition region of a target sequence and also contain a nicking enzyme binding region upstream of the recognition region and a stabilizing region upstream to the nicking enzyme binding region.

By "recognition region" is meant a nucleic acid sequence on the template that is complementary or substantially complementary to a nucleic acid sequence on the target sequence. By "recognition region on the target sequence" is meant the nucleotide sequence on the target sequence that is complementary or substantially complementary to, and binds to, the template.

By "stabilizing region" is meant a nucleic acid sequence having, for example, about 50% GC content, designed to stabilize the molecule for, for example, the nicking and/or extension reactions.

In describing the positioning of certain sequences on nucleic acid molecules, such as, for example, in the target sequence, or the template, it is understood by those of ordinary skill in the art that the terms "3'" and "5'" refer to a location of a particular sequence or region in relation to another. Thus, when a sequence or a region is 3' to or 3' of another sequence or region, the location is between that sequence or region and the 3' hydroxyl of that strand of nucleic acid. When a location in a nucleic acid is 5' to or 5' of another sequence or region, that means that the location is between that sequence or region and the 5' phosphate of that strand of nucleic acid.

The polymerase is a protein able to catalyze the specific incorporation of nucleotides to extend a 3' hydroxyl terminus of a primer molecule, such as, for example, the template oligonucleotide, against a nucleic acid target sequence. The polymerase may be, for example, thermophilic so that it is active at an elevated reaction temperature. It may also, for example, have strand displacement capabilities. It does not, however, need to be very processive (30-40 nucleotides for a single synthesis are sufficient). Often, the polymerase used does not have 5'-3' exonuclease activity. If the polymerase also has reverse transcriptase activity (such as Bst (large fragment), 9° N, Therminator, Therminator II, etc.) the reaction can also amplify RNA targets in a single step without the use of a separate reverse transcriptase. More than one polymerase may be included in the reaction, in one example one of the polymerases may have reverse transcriptase activity and the other polymerase may lack reverse transcriptase activity. In exemplary embodiments, the polymerase is BST (large fragment). The polymerase may be selected from, for example, the group consisting of one or more of the polymerases listed in Table 1.

TABLE 1

| Polymerase |
| --- |
| Bst DNA polymerase |
| Bst DNA polymerase (Large fragment) |
| 9° Nm DNA polymerase |
| Phi29 DNA polymerase |
| DNA polymerase I (*E. coli*) |
| DNA polymerase I, Large (Klenow) fragment |
| Klenow fragment (3'-5' exo-) |
| T4 DNA polymerase |
| T7 DNA polymerase |
| Deep Vent$_R$ ™ (exo-) DNA Polymerase |
| Deep Vent$_R$ ™ DNA Polymerase |
| DyNAzyme ™ EXT DNA |
| DyNAzyme ™ II Hot Start DNA Polymerase |
| Phusion ™ High-Fidelity DNA Polymerase |
| Therminator ™ DNA Polymerase |
| Therminator ™ II DNA Polymerase |
| Vent$_R$ ® DNA Polymerase |
| Vent$_R$ ® (exo-) DNA Polymerase |
| RepliPHI ™ Phi29 DNA Polymerase |
| rBst DNA Polymerase |
| rBst DNA Polymerase, Large Fragment (IsoTherm ™ DNA Polymerase) |
| MasterAmp ™ AmpliTherm ™ DNA Polymerase |
| Taq DNA polymerase |
| Tth DNA polymerase |
| Tfl DNA polymerase |
| Tgo DNA polymerase |
| SP6 DNA polymerase |
| Tbr DNA polymerase |
| DNA polymerase Beta |
| ThermoPhi DNA polymerase |
| Pyrophage 3173 (Lucigen) |

The following non-limiting examples of Reverse Transcriptases (RT) can be used in the reactions of the present method to improve performance when detecting an RNA sequence: OmniScript (Qiagen), SensiScript (Qiagen), MonsterScript (Epicentre), Transcriptor (Roche), HIV RT (Ambion), SuperScript III (Invitrogen), ThermoScript (Invitrogen), Thermo-X (Invitrogen), ImProm II (Promega).

These different RTs perform at different levels in the standard reaction buffer, and this performance rating is listed below. A "+" indicates that the amplification reaction results in specific product. More "+"s indicate that the reaction works better, with "+++++" indicating excellent results. A "−" indicates that the reaction did not result in specific product, or did not result in specific product over background.

TABLE 2

| | |
|---|---|
| OmniScript** (Qiagen) | +++++ |
| SensiScript (Qiagen) | +++ |
| MonsterScript (Epicentre) | +++ |
| Transcriptor (Roche) | ++ |
| HIV RT* (Ambion) | + |
| SuperScript III (Invitrogen) | − |
| ThermoScript (Invitrogen) | − |
| Thermo-X (Invitrogen) | − |
| ImProm II (Promega) | − |

"Nicking" refers to the cleavage of only one strand of the double-stranded portion of a fully or partially double-stranded nucleic acid. The position where the nucleic acid is nicked is referred to as the nicking site or nicking site. The recognition sequence that the nicking enzyme recognizes is referred to as the nicking enzyme binding site. "Capable of nicking" refers to an enzymatic capability of a nicking enzyme.

The nicking enzyme is a protein that binds to double-stranded DNA and cleaves one strand of a double-stranded duplex. The nicking enzyme may cleave either upstream or downstream of the binding site, or nicking enzyme recognition site. In exemplary embodiments, the reaction comprises the use of nicking enzymes that cleave or nick downstream of the binding site (top strand nicking enzymes) so that the product sequence does not contain the nicking site. Using an enzyme that cleaves downstream of the binding site allows the polymerase to more easily extend without having to displace the nicking enzyme. The nicking enzyme must be functional in the same reaction conditions as the polymerase, so optimization between the two ideal conditions for both is necessary. Nicking enzymes are available from, for example, New England Biolabs (NEB) and Fermentas. The nicking enzyme may, for example, be selected from the group consisting of one or more of the nicking enzymes listed in Table 3.

TABLE 3

| Nicking Enzyme | Alternate Name |
|---|---|
| Nb.BbvCI | |
| Nb.Bpu10I | |
| Nb.BsaI | |
| Nb.BsmI | |
| Nb.BsrDI | |
| Nb.BstNBIP | |
| Nb.BstSEIP | |
| Nb.BtsI | |
| Nb.SapI | |
| Nt.AlwI | |
| Nt.BbvCI | |
| Nt.BhaIIIP | |
| Nt.Bpu10I | |
| Nt.Bpu10IB | |

TABLE 3-continued

| Nicking Enzyme | Alternate Name |
|---|---|
| Nt.BsaI | |
| Nt.BsmAI | |
| Nt.BsmBI | |
| Nt.BspD6I | |
| Nt.BspQI | |
| Nt.Bst9I | |
| Nt.BstNBI | N.BstNB I |
| Nt.BstSEI | |
| Nt.CviARORFMP | |
| Nt.CviFRORFAP | |
| Nt.CviPII | Nt.CviPIIm |
| Nt.CviQII | |
| Nt.CviQXI | |
| Nt.EsaSS1198P | |
| Nt.MlyI | |
| Nt.SapI | |

Nicking enzymes may be, for example, selected from the group consisting of Nt.BspQI(NEB), Nb.BbvCI(NEB), Nb.BsmI(NEB), Nb.BsrDI(NEB), Nb.BtsI(NEB), Nt.AlwI (NEB), Nt.BbvCI(NEB), Nt.BstNBI(NEB), Nt.CviPII (NEB), Nb.Bpu10I(Fermantas), and Nt.Bpu10I(Fermentas). In certain embodiments, the nicking enzyme is selected from the group consisting of Nt.NBst.NBI, Nb.BsmI, and Nb.BsrDI. Those of ordinary skill in the art are aware that various nicking enzymes other than those mentioned specifically herein may be used in the present methods.

Nicking enzymes and polymerases of the present methods may be, for example, stable at room temperature, the enzymes may also, for example, be stable at temperatures up to 37° C. 42° C. 60° C., 65° C., 70° C., 75° C., 80° C., or 85° C. In certain embodiments, the enzymes are stable up to 60° C.

An enzyme is "thermophilic" when it is stable at temperatures up to 37° C., 42° C., 50-60 C, 54-60° C., 56-58° C., 60° C., 65° C., 70° C., 75° C., 80° C., or 85° C.

Product or amplified product is defined as the end result of the extension of the template along the target that is nicked and released. This product can then feed back into the amplification cycle, or it can anneal to its complement or a molecular beacon.

A "native nucleotide" refers to adenylic acid, guanylic acid, cytidylic acid, thymidylic acid, or uridylic acid. A "derivatized nucleotide" is a nucleotide other than a native nucleotide.

The reaction may be conducted in the presence of native nucleotides, such as, for example, dideoxyribonucleoside triphosphates (dNTPs). The reaction may also be carried out in the presence of labeled dNTPs, such as, for example, radiolabels such as, for example, $^{32}P$, $^{33}P$, $^{125}I$, or $^{35}S$, enzyme labels such as alkaline phosphatase, fluorescent labels such as fluorescein isothiocyanate (FITC), biotin, avidin, digoxigenin, antigens, haptens, or fluorochromes. These derivatized nucleotides may, optionally, be present in the templates.

By "constant temperature," "isothermal conditions," "essentially isothermal," or "isothermally" is meant a set of reaction conditions where the temperature of the reaction is kept essentially or substantially constant during the course of the amplification reaction. An advantage of the amplification method of the present methods is that the temperature does not need to be cycled between an upper temperature and a lower temperature. The nicking and the extension reaction will work at the same temperature or within the same narrow temperature range. However, it is not necessary that the temperature be maintained at precisely one temperature. If the equipment used to maintain an elevated temperature allows the temperature of the reaction mixture to vary by a few degrees, or few tenths of a degree, such as, for example, less than 1 degree, 0.8 degrees, 0.6 degrees, 0.4 degrees, or 0.2 degrees, this is not detrimental to the amplification reaction, and may still be considered to be an isothermal reaction.

The term "multiplex amplification" refers to the amplification of more than one nucleic acid of interest. For example, it can refer to the amplification of multiple sequences from the same sample or the amplification of one of several sequences in a sample as discussed, for example, in U.S. Pat. Nos. 5,422,252; and 5,470,723, which provide examples of multiplex strand displacement amplification. The term also refers to the amplification of one or more sequences present in multiple samples either simultaneously or in step-wise fashion.

Template Design

Forward and Reverse templates, and first and second templates, are designed so that there is a stabilizing region at the 5' end, a nicking enzyme binding site and a nicking site downstream of the stabilizing region, and a recognition region downstream of the nicking enzyme binding site and the nicking site on the 3' end of the oligonucleotide. The total oligo length can range from 19 to 40, for example from 19-40, 23-40, 20-30, 20-24, 23-24, 23-32, 25-40, 27-40, or 27-35 nucleotides depending on the length of each individual region, the temperature, the length of the target sequence, and the GC concentration. One of ordinary skill in the art would know how to balance these features of the templates. The templates may be designed so that they, together, would bind to less than or equal to 100% of the target sequence, one binding to the sense strand, and one to the antisense strand. The length of each template does not need to be the same length as the other template. For example, where the forward template binds to about 60% of the target antisense strand, the reverse template may, for example, bind to about 40% of the target sense strand. The templates may be designed to allow for spacer bases on the target sequence, that do not bind to either template. The templates thus may be designed to bind to about 30%, about 40%, about 50%, or about 60% of the target sequence.

The recognition region of the forward template is designed to be substantially identical or identical to the 5' region of the target sense strand and complementary or substantially complementary to the 3' end of the target site antisense strand. The recognition region of the forward template is of any suitable length, for example, about 8, 9, 10, 11, 12, 13, 14, 15 or 16 bases in length, and sometimes 8-16, 9-16, 10-16, 8-12, 8-15, 9-15, 10-15, or 11-14 nucleotides long. In exemplary embodiments, the length is 11-13, 11-12, 12, or 12-13 nucleotides long. The recognition region of the reverse template is designed to be substantially complementary or complementary to the 3' end of the target site sense strand. The recognition region of the reverse template is of any suitable length, for example, about 8, 9, 10, 11, 12, 13, 14, 15 or 16 bases in length, and sometimes 8-16, 9-16, 10-16, 8-12, 8-15, 9-15, 10-15, or 11-14 nucleotides long. In exemplary embodiments, the length is 11-13, 11-12, 12, or 12-13 nucleotides long. The length of the recognition region of the first template may either be the same as the length of the recognition region of the second template, or may be different.

A recognition sequence of a template often is complementary or substantially complementary to a unique sequence, or substantially unique sequence, of an organism.

The term "unique sequence" as used herein refers to a nucleotide sequence in an organism that is present in no other known organism. A "substantially unique sequence" as used herein refers to a nucleotide sequence present in a specific family of organisms, or in up to only about 1, 2, 3, 4, 5, 6, 7, 8, 9, or 10 other organisms. In some embodiments, a unique sequence or substantially unique sequence is present in ribosomal RNA or in the sense or antisense strand of DNA encoding ribosomal RNA.

Those of ordinary skill in the art are able to determine the appropriate recognition region length for optimal, efficient, amplification. In certain embodiments, to provide appropriate specificity, an 8 base-length template recognition region is a lower limit. The analytical specificity of the reaction is linked to the sum of the recognition regions of the two templates, the forward and the reverse template. If each template has a recognition region of 8 nucleotides, for example, that confers an assay that is able to detect a unique combination of 8+8=16 nucleotides, referred to as the "target size." For a given DNA strand, a target size of 16 nucleotides has $4.29 \times 10^9$ possible combinations. The human genome is $3.3 \times 10^9$ nucleotides long. Therefore, statistically, a specific 16 nucleotide sequence is expected to occur approximately once in the human genome. As the target size decreases, for example to 15 nucleotides, that would be expected to occur, on average, 3 times in the human genome ($1.07 \times 10^9$ possibilities in $3.3 \times 10^9$ occurrences), and would therefore not be as specific as a 16 nucleotide target size. For an assay with a recognition region of 7 nucleotides, conferring an assay target size of 14 bases, this would be expected to be present in the human genome 12 times ($2.68 \times 10^8$ possibilities in $3.3 \times 10^9$ occurrences). This would generate an assay with reduced specificity that would have less value in a diagnostic setting. Therefore, an 8 base recognition region for each template is often considered to be the lower limit for certain assays.

TABLE 4

| Assay Target Size | # unique possibilities |
|---|---|
| N | $4^N$ |
| 14 | 2.68E+08 |
| 15 | 1.07E+09 |
| 16 | 4.29E+09 |
| 17 | 1.72E+10 |
| 18 | 6.87E+10 |
| 19 | 2.75E+11 |
| 20 | 1.10E+12 |
| 21 | 4.40E+12 |
| 22 | 1.76E+13 |
| 23 | 7.04E+13 |
| 24 | 2.81E+14 |
| 25 | 1.13E+15 |
| 26 | 4.50E+15 |

Amplification assays in accordance with the present invention were conducted to determine the optimal length of the recognition region. In 10 minute assays, using either 0 or 100,000 copies of target DNA, a 20 mer recognition region template set did not produce detectable specific product, while specific product was detected using a 12 mer recognition region template set. The use of a 16 mer recognition region template set resulted in specific detectable product, but four-fold less specific product was detected than in an assay using the 12 mer recognition region template set. In certain embodiments, the use of a 15 mer recognition region template set generated more specific product than a 16 mer recognition region template set.

Thus, in certain exemplary embodiments, methods are provided for amplifying a double stranded nucleic acid target sequence comprising contacting a target DNA molecule comprising a double-stranded target sequence, having a sense strand and an antisense strand, with a forward template and a reverse template, wherein the forward template comprises a nucleic acid sequence comprising a recognition region at the 3' end that is complementary or substantially complementary to the 3' end of the target sequence antisense strand, wherein the recognition region is from 8 to 15 nucleotides in length; a nicking enzyme binding site and a nicking site upstream of the recognition region and a stabilizing region upstream of the nicking enzyme binding site and the nicking site; the reverse template comprises a nucleotide sequence comprising a recognition region at the 3' end that is complementary or substantially complementary to the 3' end of the target sequence sense strand, wherein the recognition region is from 8 to 15 nucleotides in length, a nicking enzyme binding site and a nicking site upstream of the recognition region, and a stabilizing region upstream of the nicking enzyme binding site and the nicking site; providing a first nicking enzyme that is capable of nicking at the nicking site of the forward template, and does not nick within the target sequence; providing a second nicking enzyme that is capable of nicking at the nicking site of the reverse template and does not nick within the target sequence; and providing a DNA polymerase; under conditions wherein amplification is performed by multiple cycles of the polymerase extending the forward and reverse templates along the target sequence producing a double-stranded nicking site, and the nicking enzymes nicking at the nicking sites, producing an amplification product. Thus, in certain embodiments, the recognition region of the forward or reverse template, or each of the forward and reverse templates is 8, 9, 10, 11, 12, 13, 14, or 15 nucleotides in length. In certain embodiments, the target sequence comprises from 1 to 5 nucleotides more than the sum of the nucleotides of the forward template recognition region and the reverse template recognition region In another exemplary embodiment, methods are provided for amplifying a single-stranded nucleic acid target sequence, comprising contacting a target nucleic acid comprising a single-stranded target sequence with a reverse template, wherein the reverse template comprises a nucleotide sequence comprising a recognition region at the 3' end that is complementary or substantially complementary to the 3' end of the target sequence wherein the recognition region is from 8 to 15 nucleotides in length, a nicking enzyme binding site and a nicking site upstream of the recognition region, and a stabilizing region upstream of the nicking enzyme binding site and the nicking site; providing a first nicking enzyme that is capable of nicking at the nicking site of the reverse template, and does not nick within the target sequence; providing a DNA polymerase under conditions wherein the polymerase extends the reverse template along the target sequence; contacting the extended reverse template with a forward template, wherein the forward template comprises a recognition region at the 3' end that is identical to the 5' end of the target sequence wherein the recognition region is from 8 to 15 nucleotides in length, a nicking enzyme binding site and a nicking site upstream of the recognition region, and a stabilizing region upstream of the nicking enzyme binding site and the nicking site; providing a second nicking enzyme that is capable of nicking at the nicking site of the forward template and does not nick within the target sequence; under conditions wherein amplification is performed by multiple cycles of the polymerase extending the forward and reverse templates along the target sequence producing a double-stranded nicking site, and the nicking enzymes nicking at the nicking sites, producing an amplification. Thus, in certain embodiments, the recognition region of the forward or reverse template, or each of the forward and reverse templates, is 8, 9, 10, 11, 12, 13, 14, or 15 nucleotides in length. In certain embodiments, the target sequence comprises from 1 to 5 nucleotides more than the sum of the nucleotides of the forward template recognition region and the reverse template recognition region In certain embodiments, the temperature at which the amplification reaction is conducted is lower than the melting temperature ($T_m$) of a template and target. In certain embodiments, the reaction temperature is, for example, from 1° C.-10° C., 1° C.-8° C., 1° C.-6° C., 1° C.-4° C., 1° C.-2° C., 2° C.-10° C., 2° C.-8° C., 2° C.-6° C., 2° C.-4° C., 2° C.-2° C. from 2° C.-4° C. or from 2° C., 3° C., 4° C., 5° C., 6° C., 7° C., or 8° C. less than the $T_m$ of a template and target. The reaction temperature also often is lower than the $T_m$ of the reaction products (e.g., products of nicking and polymerase extension of the amplification duplex shown in FIG. 1B and FIG. 1C after step 9A). The reaction temperature may be higher than the $T_m$ of the initial template/target sequence complex (drawing above step (1) of FIG. 1A). Once the template is extended to form a stable complex, the $T_m$ of the stable complex is higher than the reaction temperature.

Thus, the $T_m$ of a template/target nucleic acid target often is higher than the reaction temperature, and sometimes the $T_m$ is 5° C. or more higher than the reaction temperature, or for example, about 1° C., 2° C., 3° C., 4° C., 5° C., 6° C., 7° C., or 8° C. or more higher than the reaction temperature. The $T_m$ of each portion of the nicked strand after nicking often is higher than the reaction temperature, and sometimes the $T_m$ of each nicked portion is 5° C. or more higher than the reaction temperature, or for example, about 1° C., 2° C., 3° C., 4° C., 5° C., 6° C., 7° C., or 8° C. or more higher than the reaction temperature. The $T_m$ of the template and target may be calculated, for example, using the program provided for the IDT Oligo Analyzer (Integrated DNA Technologies) at World Wide Web URL idtdna.com/analyzer/Applications/OligoAnalyzer/ considering the salt concentration of the reaction conditions. As discussed at the IDT website, the $T_m$ calculations using the Analyzer are conducted as follows:

Melting temperature ($T_M$) is the temperature at which an oligonucleotide duplex is 50% in single-stranded form and 50% in double-stranded form. The Oligo Analyzer estimates $T_M$ from the nearest-neighbor two-state model, which is applicable to short DNA duplexes, $$T_M(° C.) = \frac{\Delta H°}{\Delta S° + R\ln[oligo]} - 273.15$$

where $\Delta H°$ (enthalpy) and $\Delta S°$ (entropy) are the melting parameters calculated from the sequence and the published nearest neighbor thermodynamic parameters, R is the ideal gas constant (1.987 cal·K$^{-1}$ mole$^{-1}$), [oligo] is the molar concentration of an oligonucleotide, and the constant of −273.15 converts temperature from Kelvin to degrees of Celsius. The most accurate, nearest-neighbor parameters were obtained from the following *publications* for DNA/DNA base pairs (Allawi, H., Santa Lucia, J., Jr., *Biochemistry*, 36, 10581), RNA/DNA base pairs (Sugimoto, N. et al., *Biochemistry*, 34, 11211), RNA/RNA base pairs (Xia, T. et al., *Biochemistry*, 37, 14719), and LNA/DNA base pairs (Mc-Tigue, P. M. et al., *Biochemistry*, 43, 5388).

$T_M$ depends on monovalent salt concentration ($[Na^+]$) of the solvent. The linear $T_M$ correction is a method known in the art. As discussed in the IDT website, scientists at IDT performed a large set of UV melting experiments (~3000 measurements) on about 100 short DNA duplexes in a variety of sodium buffers and determined that this linear function is inaccurate. OligoAnalyzer employs the improved quadratic $T_M$ salt correction function (Owczarzy, R. et al., *Biochemistry*, 43, 3537), $$\frac{1}{T_M(Na^+)} = \frac{1}{T_M(1M\ Na^+)} + (4.29 f(GC) - 3.95) \times 10^{-5} \ln[Na^+] + 9.40 \times 10^{-6} \ln^2[Na^+]$$

where f(GC) is the fraction of GC base pairs.

In certain embodiments, the lengths of the recognition regions are adjusted so that there is at least one nucleotide in the target sequence that is not in the forward template's recognition region and also does not have its complement in the reverse template's recognition region. These spacer bases (which form the "spacer region") are nucleotides contained within the target sequence that lie in between the 3' ends of the forward and reverse templates. The spacer bases are shown in, for example, FIG. 30, where they are indicated as the section of the target sense and antisense sequences between the 3' ends of the forward and reverse templates, also indicated within the "spacer region." For example, when templates T2 and T1 of FIG. 30 are used with the target, the target sense strand has 1 spacer base (or, a gap of 1 nucleotide)—T, and the target antisense strand has 1 spacer base (or, a gap of 1-nucleotide)—A. In certain embodiments, 5 spacer bases or less are present in the target sequence. In exemplary embodiments, the number of spacer bases is 2 to 3. In certain embodiments, the number of spacer bases is 1, 2, or 3. In other embodiments, there is 1 spacer base. In other embodiments, there are 2 spacer bases. In other embodiments, there are 3 spacer bases. In other embodiments, the number of spacer bases is 1, 2, 3, 4, or 5.

Thus, in exemplary embodiments of the present methods, the target sequence comprises from 1 to 5 nucleotides between the target sequence nucleotide that hybridizes to the 3' end of the first template and the corresponding nucleotide to the nucleotide of the complement of the first strand that hybridizes to the 3' end of the second template. By "corresponding nucleotide" is meant the nucleotide on one strand of the target nucleotide sequence that hybridizes to the complementary strand of the target nucleotide sequence when the two strands are aligned. These 1 to 5 nucleotides are also called spacer bases.

These spacer bases allow for distinction of the true amplified product from any background products amplified by extension due to overlapping templates in a similar manner to primer-dimers. This consideration allows for improved discrimination between background noise and amplification of a target sequence. However, these spacer bases are not required for the amplification to proceed.

Thus, in certain exemplary embodiments, methods are provided for amplifying a double stranded nucleic acid target sequence comprising contacting a target DNA molecule comprising a double-stranded target sequence, having a sense strand and an antisense strand, with a forward template and a reverse template, wherein the forward template comprises a nucleic acid sequence comprising a recognition region at the 3' end that is complementary or substantially complementary to the 3' end of the target sequence antisense strand; a nicking enzyme binding site and a nicking enzyme binding site and a nicking site upstream of the recognition region and a stabilizing region upstream of the nicking enzyme binding site and the nicking site; the reverse template comprises a nucleotide sequence comprising a recognition region at the 3' end that is complementary or substantially complementary to the 3' end of the target sequence sense strand, a nicking enzyme binding site and a nicking site upstream of the recognition region, and a stabilizing region upstream of the nicking enzyme binding site and the nicking site; providing a first nicking enzyme that is capable of nicking at the nicking site of the forward template, and does not nick within the target sequence; providing a second nicking enzyme that is capable of nicking at the nicking site of the reverse template and does not nick within the target sequence; and providing a DNA polymerase; under conditions wherein amplification is performed by multiple cycles of the polymerase extending the forward and reverse templates along the target sequence producing a double-stranded nicking site, and the nicking enzymes nicking at the nicking sites, producing an amplification product, wherein the target sequence comprises from 1 to 5 nucleotides more than the sum of the nucleotides of the forward template recognition region and the reverse template recognition region. Thus, in certain embodiments, the target sequence comprises 1, 2, 3, 4, or 5 nucleotides more than the sum of the nucleotides of the forward template recognition region and the reverse template recognition region.

In another exemplary embodiment, methods are provided for amplifying a single-stranded nucleic acid target sequence, comprising contacting a target nucleic acid comprising a single-stranded target sequence with a reverse template, wherein the reverse template comprises a nucleotide sequence comprising a recognition region at the 3' end that is complementary or substantially complementary to the 3' end of the target sequence, a nicking enzyme binding site and a nicking site upstream of the recognition region, and a stabilizing region upstream of the nicking enzyme binding site and the nicking site; providing a first nicking enzyme that is capable of nicking at the nicking site of the reverse template, and does not nick within the target sequence; providing a DNA polymerase under conditions wherein the polymerase extends the reverse template along the target sequence; contacting the extended reverse template with a forward template, wherein the forward template comprises a recognition region at the 3' end that is identical to the 5' end of the target sequence a nicking enzyme binding site and a nicking site upstream of the recognition region, and a stabilizing region upstream of the nicking enzyme binding site and the nicking site; providing a second nicking enzyme that is capable of nicking at the nicking site of the forward template and does not nick within the target sequence; under conditions wherein amplification is performed by multiple cycles of the polymerase extending the forward and reverse templates along the target sequence producing a double-stranded nicking site, and the nicking enzymes nicking at the nicking sites, producing an amplification product, wherein the target sequence comprises from 1 to 5 nucleotides more than the sum of the nucleotides of the forward template recognition region and the reverse template recognition region. Thus, in certain embodiments, the target sequence comprises 1, 2, 3, 4, or 5 nucleotides more than the sum of the nucleotides of the forward template recognition region and the reverse template recognition region.

The nicking enzyme binding site sequence of the template depends on which nicking enzyme is chosen for each template. Different nicking enzymes may be used in a single assay, but a simple amplification may, for example, employ a single nicking enzyme for use with both templates. Thus, the embodiments of the present methods include those where both templates comprise recognition sites for the same nicking enzyme, and only one nicking enzyme is used in the reaction. In these embodiments, both the first and second nicking enzymes are the same. The present method also includes those embodiments where each template comprises a recognition site for a different nicking enzyme, and two nicking enzymes are used in the reaction.

For example, in the case of Nt.BstNBI, the enzyme binding site is 5'-GAGTC-3' and the enzyme nicks the top strand four nucleotides down stream of this site (i.e., GAGTCNNNN^). The amplification reaction shows little dependence on the sequence of these four nucleotides (N), though optimal sequence of this region is 25% or less GC content and with a thymine adjacent to the 5' nucleotide of the binding region. The latter stipulation allows for the priming ability of products that have an additional adenine added on by the polymerase. The sequence of the four nucleotides can be optimized to create or eliminate the presence of hairpins, self-dimers, or heterodimers, depending on the application.

The stabilizing region on the 5' end of the template oligonucleotide is designed to be roughly 50% GC. Thus, the GC content may be, for example, about 40%-60%, about 42%-58%, about 44%-56%, about 46%-54%, about 48%-52%, or about 49%-51%. These parameters result in a stabilizing region length of 8-11 nucleotides for the Nt.BstNBI enzyme, though lengths as short as 6 and as long as 15 nucleotides have been tested and were shown to work in this amplification method. Longer stabilizing regions or increased % GC to greater than 50% could further stabilize the nicking and extension reactions at higher reaction temperatures. The sequence of the 5' stabilizing regions of forward and reverse templates are usually identical, but can be varied if the aim is to capture each product strand independently. The sequence of this region should not interfere with the nicking site or the recognition region, though short internal hairpins within the template sequence have been shown to have improved real-time results.

In certain embodiments, one or more agents that destabilize nucleic acid interaction (e.g., inter-strand or intra-strand interactions) are included in an amplification process, and in alternative embodiments, one or more of such agents are not included in an amplification process. Examples of agents that destabilize nucleic acid interaction are those that destabilize double-stranded structure (e.g., double-stranded DNA), and/or structures within a strand (e.g., secondary or tertiary structures in RNA), and include, without limitation, betaines and other tetra-ammonium compounds, formamide, glycerol, sorbitol, sodium perchlorate, dimethylsulfoxide (DMSO), lower alkyl alcohols (e.g., ethanol; 1-4 carbon alcohols), urea, trialkyl ammonium salts (e.g., triethyl ammonium chloride), single strand binding (ssb) proteins, such as, for example, *E. coli* ssb, helicases, such as, for example, *E. coli* DNA helicases I, II, or IV, lower alkyl (1-4 C) alcohols, and the like. Without being bound by theory, such agents lower the melting temperature ($T_m$) of nucleic acid interactions (e.g., lower duplex $T_m$). Those of ordinary skill in the art may determine the appropriate destabilizing agent and appropriate destabilizing agent concentration for the reaction, considering, for example, the amount of destabilization as well as the need to maintain enzymatic activity.

Examples of concentrations include about 10% glycerol, about 10% sodium perchlorate, about 10% DMSO, about 10% sorbitol, about 2.4 molar triethyl ammonium chloride, and about greater than 1, 2, 3, 4, or 5 molar betaine, for example, about 5-6 molar betaine. Betaine, or N,N,N-trimethylglycine, may be purchased from, for example Sigma-Aldrich, for example, catalog numbers B2629 or B0300. It may be used, for example, in combination with low concentrations of DMSO, for example, about 1-2, or about 1.3% DMSO to about IM betaine.

The templates of the present methods may include, for example, spacers, blocking groups, and modified nucleotides. Modified nucleotides are nucleotides or nucleotide triphosphates that differ in composition and/or structure from natural nucleotide and nucleotide triphosphates. Modified nucleotide or nucleotide triphosphates used herein may, for example, be modified in such a way that, when the modifications are present on one strand of a double-stranded nucleic acid where there is a restriction endonuclease recognition site, the modified nucleotide or nucleotide triphosphates protect the modified strand against cleavage by restriction enzymes. Thus, the presence of the modified nucleotides or nucleotide triphosphates encourages the nicking rather than the cleavage of the double-stranded nucleic acid. Blocking groups are chemical moieties that can be added to the template to inhibit target sequence-independent nucleic acid polymerization by the polymerase. Blocking groups are usually located at the 3' end of the template. Examples of blocking groups include, for example, alkyl groups, non-nucleotide linkers, phosphorothioate, alkanediol residues, peptide nucleic acid, and nucleotide derivatives lacking a 3'-OH, including, for example, cordycepin. Examples of spacers, include, for example, C3 spacers. Spacers may be used, for example, within the template, and also, for example, at the 5' end, to attach other groups, such as, for example, labels.

Unmodified nucleotides often are provided for template extension. Unmodified nucleotides and nucleotide derivatives often are not provided for incorporation into extended templates. In certain embodiments, however, one or more modified nucleotides or nucleotide derivatives may be provided and incorporated into an extended template.

The amplification reaction may also include helper oligonucleotides. Helper oligonucleotides are oligonucleotides that are, for example, about 5-10, 5-15, 5-20, nucleotides long. The presence of helper oligonucleotides may increase the speed, amount, or sensitivity of the amplification reaction. Helper oligonucleotides are not incorporated into the final product. Those of ordinary skill in the art would be able to determine the appropriate helper oligonucleotides to add to a reaction, as well as the amount to add. One example of a way to determine the appropriate helper oligonucleotides is to synthesize oligonucleotides that are complementary to various regions of the target nucleic acid or its complement, and add them to the assay in varying amounts, comparing the assay with the helper oligonucleotides to one without helper oligonucleotides as a control. Helper oligonucleotides may be synthesized that are complementary to regions upstream or downstream of the recognition region, or its complement. For example, sets of helper oligonucleotides about 10 bases long may be synthesized that are complementary to regions spaced every 5-10 bases upstream or downstream of the recognition region, then tested in pairs for their ability to enhance the amplification reaction.

Detailed Mechanism of Amplification

Amplification reactions of the present methods require the presence of a nucleic acid target, at least two template oligonucleotides, a nicking enzyme, for example, a thermophilic nicking enzyme, a thermophilic polymerase, and buffer components all held at the reaction temperature. The recognition region of the templates interacts with the complementary or substantially complementary target sequence. Since the melting temperature of the complementary or substantially complementary regions of the target and template is well below the reaction temperature, the interaction between the two nucleic acid strands is transient, but allows enough time for a thermophilic polymerase to extend from the 3' end of the template along the target strand. Experiments have shown that certain polymerases bind to single-stranded oligonucleotides. The pre-formation of this complex can facilitate the speed of the amplification process.

For a double-stranded target, both templates can interact with the corresponding target strands simultaneously (forward template with the antisense strand and reverse template with the sense strand) during the normal breathing of double-stranded DNA. The target may also be generated by a single or double nick sites within the genome sequence. For a single-stranded target (either RNA or DNA), the reverse template binds and extends first (FIG. 1, Step 1 and 2). The extended sequence contains the complement to the forward template. The forward template then displaces a region of the target and binds to the 3' synthesized region complementary or substantially complementary to the recognition region of the forward template (Step 3). Alternatively, another reverse template can also displace the initial extended reverse template at the recognition region to create a single-stranded extended reverse template for the forward template to bind. The initial binding and extension of the templates is facilitated by a non-processive polymerase that extends shorter strands of DNA so that the melting temperature of the synthesized product is above the reaction temperature. The single-stranded product is then available for the next template recognition site to bind and polymerase to extend.

The forward template is extended to the 5' end of the reverse template, creating a double-stranded nicking enzyme binding site for the reverse template (Step 5). The nicking enzyme then binds to the duplex and nicks directly upstream of the recognition sequence of the reverse template strand (in the case of a top-strand nicking enzyme) (Step 6). The nucleic acid sequence downstream of the nick is either released (if the melting temperature is near the reaction temperature) and/or is displaced by the polymerase synthesis from the 3'-OH nick site. Polymerase extends along the forward template to the 5' end of the forward template (Step 8). The double-strand formed from the extension of both templates creates a nicking enzyme binding site on either end of the duplex. This double-strand is termed the NEAR™ amplification duplex. When nicking enzyme binds and nicks, either the target product located in between the two nick sites (with 5'-phosphate and 3'-OH) is released, usually ranging in length from (but is not limited to) 23 to 29 bases (Steps 9-11A), or the singly-nicked product containing the target product and the reverse complement of the nick site and stability region of the template (usually 36 to 48 bases in length) is released (Steps 9-11B). Another depiction of mechanisms of the reaction is presented in FIG. 33.

The ratio of products 1 to 2 can be adjusted by varying the concentrations of the templates. The forward:reverse template ratio may vary from, for example, molar ratios of 100:1, 75:1; 50:1, 40:1, 30:1, 20:1, 10:1, 5:1, 2.5:1, 1:1, 1:2.5, 1:5, 1:10, 1:20, 1:30, 1:40, 1:50, 1:75, or 1:100. The ratio of products (A to B) is dependent on the ratio of nicking enzyme to polymerase, i.e. a higher concentration of polymerase results in more of the longer length product (B) since there is comparatively less nicking enzyme to nick both strands simultaneously before the polymerase extends. Since displaced/released product of the reverse template feeds into the forward template and vice versa, exponential amplification is achieved. The nicking enzyme:polymerase ratio may vary from, for example, enzyme unit ratios of 20:1, 15:1; 10:1, 5:1, 4:1, 3:1, 2:1, 1.5:1, 1:1, 1:1.5, 1:2, 1:3, 1:4, 1:5, 1:10, 1:15, 1:20. In certain embodiments, the ratio of nicking enzyme to polymerase may, for example, be 1:3, 1:2, 1:1.5, or 1:0.8. Those of ordinary skill in the art recognize that these ratios may represent rounded values. This nicking and polymerase extension process continues until one of the resources (usually dNTPs or enzyme) is exhausted.

As demonstrated in the Examples, the time that the reaction is run may vary from, for example, within about 1 minute, or within about 2, 3, 4, 5, 6, 7, 8, 9, 10, 11, 12, 13, 14, 15, 16, 17, 18, 19 or 20 minutes. Longer reaction times may produce acceptable results where speed is not an issue. In some embodiments, the reaction is between 1-20 minutes, 1-15 minutes or 1-10, 1-8, 1-5, 1-2.5, 2.5-5, 2.5-8, 2.5-10, or 2.5-20 minutes in certain embodiments. The amplification processes described herein are efficient, and in some embodiments, as shown, for example, in the Examples, there is about $1 \times 10^6$-fold or more amplification, about $1 \times 10^7$-fold or more amplification, about $1 \times 10^8$-fold or more amplification, about $1 \times 10^9$-fold or more amplification, or about $1 \times 10^{10}$-fold or more amplification in the time frame of the reaction, for example, in 5 or ten minutes. The reaction is highly sensitive, and is able to detect, for example, as low as about 1, 2, 3, 4, 5, 6, 7, 8, 9, 10, 20, 30, 40, 50, 60, 70, 80, 90, or 100 copies, or more, in a sample, as many as 200, 500, 1,000, 5,000, or 10,000, or more copies in a sample, or, for example, may detect a target that is present at a concentration of, for example, about 3.32E−13 micromolar to about 3.32E−8 micromolar, about 1.66E−12 micromolar to about 3.32E−8 micromolar, about 3.32E−13 micromolar to about 3.32E−7 micromolar, or about 3.32E−13 micromolar to about 3.32E−6 micromolar.

In certain exemplary embodiments, methods are provided for amplifying a double stranded nucleic acid target sequence comprising contacting a target DNA molecule comprising a double-stranded target sequence, having a sense strand and an antisense strand, with a forward template and a reverse template, wherein the forward template comprises a nucleic acid sequence comprising a recognition region at the 3' end that is complementary or substantially complementary to the 3' end of the target sequence antisense strand; a nicking enzyme binding site and a nicking site upstream of the recognition region and a stabilizing region upstream of the nicking enzyme binding site and the nicking site; the reverse template comprises a nucleotide sequence comprising a recognition region at the 3' end that is complementary or substantially complementary to the 3' end of the target sequence sense strand, a nicking enzyme binding site and a nicking site upstream of the recognition region, and a stabilizing region upstream of the nicking enzyme binding site and the nicking site; providing a first nicking enzyme that is capable of nicking at the nicking site of the forward template, and does not nick within the target sequence; providing a second nicking enzyme that is capable of nicking at the nicking site of the reverse template and does not nick within the target sequence; and providing a DNA polymerase; under conditions wherein amplification is performed by multiple cycles of the polymerase extending the forward and reverse templates along the target sequence producing a double-stranded nicking site, and the nicking enzymes nicking at the nicking sites, producing an amplification product, wherein about $10^6$ (1E+06) copies of a target sequence are produced in 10 minutes, under isothermal conditions. In other embodiments, about $10^7$ (1E+07) copies are produced in 10 minutes. For multiplexed assays, the time to produce the same amount of copies may be increased to about, for example, 12, 14, 15, 18, or 20 minutes. The size of the target sequence in these assays, for purposes of calculating the efficiency, may be, for example, from about 20 to about 40 nucleotides, from 20 to 30 nucleotides, or, for example, from about 20 to about 33 nucleotides. The time of the reaction is calculated from the time that all of the reaction products are present in the same vessel, container, or the like, so that the amplification reaction may start, to the time that heat is applied or chemical agents are added to stop the reaction.

In another exemplary embodiment, methods are provided for amplifying a single-stranded nucleic acid target sequence, comprising contacting a target nucleic acid comprising a single-stranded target sequence with a reverse template, wherein the reverse template comprises a nucleotide sequence comprising a recognition region at the 3' end that is complementary or substantially complementary to the 3' end of the target sequence, a nicking enzyme binding site and a nicking site upstream of the recognition region, and a stabilizing region upstream of the nicking enzyme binding site and the nicking site; providing a first nicking enzyme that is capable of nicking at the nicking site of the reverse template, and does not nick within the target sequence; providing a DNA polymerase under conditions wherein the polymerase extends the reverse template along the target sequence; contacting the extended reverse template with a forward template, wherein the forward template comprises a recognition region at the 3' end that is identical to the 5' end of the target sequence a nicking enzyme binding site and a nicking site upstream of the recognition region, and a stabilizing region upstream of the nicking enzyme binding site and the nicking site; providing a second nicking enzyme that is capable of nicking at the nicking site of the forward template and does not nick within the target sequence; under conditions wherein amplification is performed by multiple cycles of the polymerase extending the forward and reverse templates along the target sequence producing a double-stranded nicking site, and the nicking enzymes nicking at the nicking sites, producing an amplification product, wherein about $10^6$ (1E+06) copies of a target sequence are produced in 10 minutes, under isothermal conditions. In other embodiments, about $10^7$ (1E+07) copies are produced in 10 minutes. For multiplexed assays, the time to produce the same amount of copies may be increased to about, for example, 12, 14, 15, 18, or 20 minutes. The size of the target sequence in these assays, for purposes of calculating the efficiency, may be, for example, from about 20 to about 40 nucleotides, or, for example, from about 20 to about 33 nucleotides. The time of the reaction is calculated from the time that all of the reaction products are present in the same vessel, container, or the like, so that the amplification reaction may start.

The present methods do not require the use of temperature cycling, as often is required in methods of amplification to dissociate the target sequence from the amplified nucleic acid. The temperature of the reaction may vary based on the length of the sequence, and the GC concentration, but, as understood by those of ordinary skill in the art, the temperature should be high enough to minimize non-specific binding. The temperature should also be suitable for the enzymes of the reaction, the nicking enzyme and the polymerase. For example, the reaction may be run at about 52° C., 53° C., 54° C., 55° C., 56° C., 57° C., 58° C., 59° C., or 60° C. In some embodiments, the reaction is run at about 37° C.-85° C., 37° C.-60° C., 54° C.-60° C., 55° C.-60° C., 58° C.-60° C. and, in exemplary embodiments, from 56° C.-58° C. In certain embodiments, there is no denaturation step in the process. The entire amplification process, including interacting templates with target nucleic acid, is conducted within substantially isothermal conditions, and without a denaturing step (e.g., no significant temperature increase (e.g., no increase in temperature to 90-110° C.)), in some embodiments of the present methods.

Thus, in certain exemplary embodiments, methods are provided for amplifying a double stranded nucleic acid target sequence comprising contacting a target DNA molecule comprising a double-stranded target sequence, having a sense strand and an antisense strand, with a forward template and a reverse template, wherein the forward template comprises a nucleic acid sequence comprising a recognition region at the 3' end that is complementary or substantially complementary to the 3' end of the target sequence antisense strand; a nicking enzyme binding site and a nicking site upstream of the recognition region and a stabilizing region upstream of the nicking enzyme binding site and the nicking site; the reverse template comprises a nucleotide sequence comprising a recognition region at the 3' end that is complementary or substantially complementary to the 3' end of the target sequence sense strand, a nicking enzyme binding site and a nicking site upstream of the recognition region, and a stabilizing region upstream of the nicking enzyme binding site and the nicking site; providing a first nicking enzyme that is capable of nicking at the nicking site of the forward template, and does not nick within the target sequence; providing a second nicking enzyme that is capable of nicking at the nicking site of the reverse template and does not nick within the target sequence; and providing a DNA polymerase; under conditions wherein amplification is performed by multiple cycles of the polymerase extending the forward and reverse templates along the target sequence producing a double-stranded nicking site, and the nicking enzymes nicking at the nicking sites, producing an amplification product, wherein the foregoing steps are conducted under isothermal conditions.

In another exemplary embodiment, methods are provided for amplifying a single-stranded nucleic acid target sequence, comprising contacting a target nucleic acid comprising a single-stranded target sequence with a reverse template, wherein the reverse template comprises a nucleotide sequence comprising a recognition region at the 3' end that is complementary or substantially complementary to the 3' end of the target sequence, a nicking enzyme binding site and a nicking site upstream of the recognition region, and a stabilizing region upstream of the nicking enzyme binding site and the nicking site; providing a first nicking enzyme that is capable of nicking at the nicking site of the reverse template, and does not nick within the target sequence; providing a DNA polymerase under conditions wherein the polymerase extends the reverse template along the target sequence; contacting the extended reverse template with a forward template, wherein the forward template comprises a recognition region at the 3' end that is identical to the 5' end of the target sequence a nicking enzyme binding site and a nicking site upstream of the recognition region, and a stabilizing region upstream of the nicking enzyme binding site and the nicking site; providing a second nicking enzyme that is capable of nicking at the nicking site of the forward template and does not nick within the target sequence; under conditions wherein amplification is performed by multiple cycles of the polymerase extending the forward and reverse templates along the target sequence producing a double-stranded nicking site, and the nicking enzymes nicking at the nicking sites, producing an amplification product, wherein the foregoing steps are conducted under isothermal conditions.

The polymerase may be mixed with the target nucleic acid molecule before, after, or at the same time as, the nicking enzyme. In exemplary embodiments, a reaction buffer is optimized to be suitable for both the nicking enzyme and the polymerase.

Reactions may be allowed to completion, that is, when one of the resources is exhausted. Or, the reaction may be stopped using methods known to those of ordinary skill in the art, such as, for example, heat inactivation, or the addition of EDTA, high salts, or detergents. In exemplary embodiments, where mass spectrometry is to be used following amplification, EDTA may be used to stop the reaction.

Reaction Components

In a 1.5 mL Eppendorf tube combine the following reagents in order from top to bottom:

| Reagent Added: | microliters Per Reaction |
| --- | --- |
| H$_2$O | 31.4 |
| 10X Thermopol Buffer (NEB) | 5 |
| 10X NEB Buffer 3 | 2.5 |
| 100 mM MgSO$_4$ | 4.5 |
| 10 mM dNTPs | 1.5 |
| 8 U/microliters Bst Pol | 0.6 |
| 10 U/microliters N.BstNBI | 1.5 |
| 20 micromolar Forward Template | 0.25 |
| 20 micromolar Reverse Template | 0.25 |
| Total reaction mixture | 47.5 |
| Target sample | 2.5 |
| Total Reaction Volume | 50 microliters |

The concentrations of components for the reaction conditions in this example are as follows:

| Concentration | Component |
| --- | --- |
| 45.7 mM | Tris-HCl |
| 13.9 mM | KCl |
| 10 mM | (NH$_4$)$_2$SO$_4$ |
| 50 mM | NaCl |
| 0.5 mM | DTT |
| 15 mM | MgCl$_2$ |
| 0.10% | Triton X-100 |
| 0.008 mM | EDTA |
| 6 µg/mL | BSA |
| 3.90% | Glycerol (can be lower if using a more concentrated enzyme stock) |
| 0.3 U/microliter | Nt.BstNBI |
| 0.1-0.4 U/microliter | Bst polymerase (large fragment) |
| 0.1 micromolar | Forward template |
| 0.1 micromolar | Reverse template |

Variations in buffer conditions, MgSO$_4$ concentration, polymerase concentration, and template concentrations all can be optimized based on the assay sequence and desired detection method. The amount of glycerol may, for example, be lowered if a more concentrated enzyme stock is used. In certain embodiments, the concentration of Mg$^{2+}$ ions added as a reactant is about 9 mM to about 25 mM, about 9 mM to 21 mM, about 9 to 21 mM, about 9 to 20 mM, about 9 to 15 mM, and, in exemplary embodiments, about 10 mM to about 18 mM, about 10 mM to about 25 mM, about 10 mM to 21 mM, about 12 to 21 mM, about 10 to 20 mM, about 10 to 15 mM, about 10.3 mM to about 20 mM, about 10.3 mM to about 14.9 mM, or about 15 mM, for example. Also, those of ordinary skill in the art recognize that the reaction may be run without EDTA or BSA; these components may be present in the reaction as part of the storage buffers for the enzymes. The volumes can be scaled for larger or smaller total reaction volumes. The volume is usually between 5 µL and 100 µL.

The template concentrations are typically in excess of the concentration of target. The concentrations of the forward and reverse templates can be at the same or at different concentrations to bias the amplification of one product over the other. The concentration of each is usually between 10 nM and 1 µM.

Additives such as BSA, non-ionic detergents such as Triton X-100 or Tween-20, DMSO, DTT, and RNase inhibitor may be included for optimization purposes without adversely affecting the amplification reaction.

Preparing/Adding Target

Targets may be diluted in 1× Thermopol Buffer II, 1×TE (pH 7.5) or H$_2$0. Hot start conditions allow for faster, more specific amplification. In this case, the reaction mix (minus either enzymes or templates and target) is heated to the reaction temperature for 2 minutes, after which the reaction mix is added to the other component (enzymes or templates/target). The target can be added in any volume up to the total amount of water required in the reaction. In this case, the target would be diluted in water. In the example above for a 50 microliter total reaction volume, 2.5 microliters of the prepared target should be added per reaction to bring the total reaction volume to 50 microliters. Reaction volumes of the present methods can be increased or decreased, depending on the needs of the user. Reaction volumes of, for example, 5, 10, 15, 20, 25, 30, 35, 40, 45, 50 microliters or more, or larger reaction volumes of, for example, 75, 100, 150, 200, 300, 400, 500 microliters, for example, may be used in the present methods.

Running the Reaction

The reaction is run at a constant temperature, usually between 54° C. and 60° C. for the enzyme combination of Bst polymerase (large fragment) and Nt.Bst.NB1 nicking enzyme. Other enzyme combinations may be used and the optimal reaction temperature will be based on the optimal temperature for both the nicking enzyme and polymerase to work in concert as well as the melting temperature of the reaction products. The reaction is held at temperature for 2.5 to 10 minutes, for example, until the desired amount of amplification is achieved. The reaction may be stopped by either a heat inactivation step to inactivate the enzymes (when using enzymes that can be heat-killed). Alternatively, the reaction may be stopped by adding EDTA to the reaction.

Readout

The amplified target sequence may be detected by any method known to one of ordinary skill in the art. By way of non-limiting example, several of these known methods are presented herein. In one method, amplified products may be detected by gel electrophoresis, thus detecting reaction products having a specific length. The nucleotides may, for example, be labeled, such as, for example, with biotin. Biotin-labeled amplified sequences may be captured using avidin bound to a signal generating enzyme, for example, peroxidase.

Nucleic acid detection methods may employ the use of dyes that specifically stain double-stranded DNA. Intercalating dyes that exhibit enhanced fluorescence upon binding to DNA or RNA are a basic tool in molecular and cell biology. Dyes may be, for example, DNA or RNA intercalating fluorophores and may include but are not limited to the following examples: Acridine orange, ethidium bromide, Hoechst dyes, PicoGreen, propidium iodide, SYBR I (an asymmetrical cyanine dye), SYBR II, TOTO (a thiaxole orange dimer) and YOYO (an oxazole yellow dimer), and the like. Dyes provide an opportunity for increasing the sensitivity of nucleic acid detection when used in conjunction with various detection methods and may have varying optimal usage parameters. For example ethidium bromide is commonly used to stain DNA in agarose gels after gel electrophoresis and during PCR (Hiquchi et al., Nature Biotechnology 10; 413-417, April 1992), propidium iodide and Hoechst 33258 are used in flow cytometry to determine DNA ploidy of cells, SYBR Green 1 has been used in the analysis of double-stranded DNA by capillary electrophoresis with laser induced fluorescence detection and Pico Green has been used to enhance the detection of double-stranded DNA after matched ion pair polynucleotide chromatography (Singer et al., Analytical Biochemistry 249, 229-238 1997).

Nucleic acid detection methods may also employ the use of labeled nucleotides incorporated directly into the target sequence or into probes containing complementary or substantially complementary sequences to the target of interest. Such labels may be radioactive and/or fluorescent in nature and can be resolved in any of the manners discussed herein. Labeled nucleotides, which can be detected but otherwise function as native nucleotides, are to be distinguished from modified nucleotides, which do not function as native nucleotides.

Methods of detecting and/or continuously monitoring the amplification of nucleic acid products are also well known to those skilled in the art and several examples are described below.

The production or presence of target nucleic acids and nucleic acid sequences may be detected and monitored by Molecular Beacons. Molecular Beacons are hair-pin shaped oligonucleotides containing a fluorophore on one end and a quenching dye on the opposite end. The loop of the hair-pin contains a probe sequence that is complementary or substantially complementary to a target sequence and the stem is formed by annealing of complementary or substantially complementary arm sequences located on either side of the probe sequence. A fluorophore and a quenching molecule are covalently linked at opposite ends of each arm. Under conditions that prevent the oligonucleotides from hybridizing to its complementary or substantially complementary target or when the molecular beacon is free in solution the fluorescent and quenching molecules are proximal to one another preventing fluorescence resonance energy transfer (FRET). When the molecular beacon encounters a target molecule, hybridization occurs; the loop structure is converted to a stable more rigid conformation causing separation of the fluorophore and quencher molecules leading to fluorescence (Tyagi et al. Nature Biotechnology 14: March 1996, 303-308). Due to the specificity of the probe, the generation of fluorescence is exclusively due to the synthesis of the intended amplified product.

Molecular beacons are extraordinarily specific and can discern a single nucleotide polymorphism. Molecular beacons can also be synthesized with different colored fluorophores and different target sequences, enabling several products in the same reaction to be quantified simultaneously. For quantitative amplification processes, molecular beacons can specifically bind to the amplified target following each cycle of amplification, and because non-hybridized molecular beacons are dark, it is not necessary to isolate the probe-target hybrids to quantitatively determine the amount of amplified product. The resulting signal is proportional to the amount of amplified product. This can be done in real time. As with other real time formats, the specific reaction conditions must be optimized for each primer/probe set to ensure accuracy and precision.

The production or presence of target nucleic acids and nucleic acid sequences may also be detected and monitored by Fluorescence resonance energy transfer (FRET). FRET is an energy transfer mechanism between two chromophores: a donor and an acceptor molecule. Briefly, a donor fluorophore molecule is excited at a specific excitation wavelength. The subsequent emission from the donor molecule as it returns to its ground state may transfer excitation energy to the acceptor molecule through a long range dipole-dipole interaction. The intensity of the emission of the acceptor molecule can be monitored and is a function of the distance between the donor and the acceptor, the overlap of the donor emission spectrum and the acceptor absorption spectrum and the orientation of the donor emission dipole moment and the acceptor absorption dipole moment. FRET is a useful tool to quantify molecular dynamics, for example, in DNA-DNA interactions as seen with Molecular Beacons. For monitoring the production of a specific product a probe can be labeled with a donor molecule on one end and an acceptor molecule on the other. Probe-target hybridization brings a change in the distance or orientation of the donor and acceptor and FRET change is observed. (Joseph R. Lakowicz, "Principles of Fluorescence Spectroscopy", Plenum Publishing Corporation, 2nd edition (Jul. 1, 1999)).

The production or presence of target nucleic acids and nucleic acid sequences may also be detected and monitored by Mass Spectrometry. Mass Spectrometry is an analytical technique that may be used to determine the structure and quantity of the target nucleic acid species and can be used to provide rapid analysis of complex mixtures. Following the method, samples are ionized, the resulting ions separated in electric and/or magnetic fields according to their mass-to-charge ratio, and a detector measures the mass-to-charge ratio of ions. (Crain, P. F. and McCloskey, J. A., Current Opinion in Biotechnology 9: 25-34 (1998)). Mass spectrometry methods include, for example, MALDI, MALDI/TOF, or Electrospray. These methods may be combined with gas chromatography (GC/MS) and liquid chromatography (LC/MS). MS has been applied to the sequence determination of DNA and RNA oligonucleotides (Limbach P., MassSpectrom. Rev. 15: 297-336 (1996); Murray K., J. Mass Spectrom. 31: 1203-1215 (1996)). MS and more particularly, matrix-assisted laser desorption/ionization MS (MALDI MS) has the potential of very high throughput due to high-speed signal acquisition and automated analysis off solid surfaces. It has been pointed out that MS, in addition to saving time, measures an intrinsic property of the molecules, and therefore yields a significantly more informative signal (Koster H. et al., Nature Biotechnol., 14: 1123-1128 (1996)).

The production or presence of target nucleic acids and nucleic acid sequences may also be detected and monitored by various methods of gel electrophoresis. Gel electrophoresis involves the separation of nucleic acids through a matrix, generally a cross-linked polymer, using an electromotive force that pulls the molecules through the matrix.

Molecules move through the matrix at different rates causing a separation between products that can be visualized and interpreted via any one of a number of methods including but not limited to; autoradiography, phosphorimaging, and staining with nucleic acid chelating dyes.

The production or presence of target nucleic acids and nucleic acid sequences may also be detected and monitored by capillary gel electrophoresis. Capillary-gel Electrophoresis (CGE) is a combination of traditional gel electrophoresis and liquid chromatography that employs a medium such as polyacrylamide in a narrow bore capillary to generate fast, high-efficient separations of nucleic acid molecules with up to single base resolution. CGE is commonly combined with laser induced fluorescence (LIF) detection where as few as six molecules of stained DNA can be detected. CGE/LIF detection generally involves the use of fluorescent DNA intercalating dyes including ethidium bromide, YOYO and SYBR Green 1 but can also involve the use of fluorescent DNA derivatives where the fluorescent dye is covalently bound to the DNA. Simultaneous identification of several different target sequences can be made using this method.

The production or presence of target nucleic acids and nucleic acid sequences may also be detected and monitored by various surface capture methods. This is accomplished by the immobilization of specific oligonucleotides to a surface producing a biosensor that is both highly sensitive and selective. Surfaces used in this method may include but are not limited to gold and carbon and may use a number of covalent or noncovalent coupling methods to attach the probe to the surface. The subsequent detection of a target DNA can be monitored by a variety of methods.

Electrochemical methods generally involve measuring the cathodic peak of intercalators, such as methylene blue, on the DNA probe electrode and visualized with square wave voltammograms. Binding of the target sequence can be observed by a decrease in the magnitude of the voltammetric reduction signals of methylene blue as it interacts with dsDNA and ssDNA differently reflecting the extent of the hybrid formation.

Surface Plasmon Resonance (SPR) can also be used to monitor the kinetics of probe attachment as well as the process of target capture. SPR does not require the use of fluorescence probes or other labels. SPR relies on the principle of light being reflected and refracted on an interface of two transparent media of different refractive indexes. Using monochromatic and p-polarized light and two transparent media with an interface comprising a thin layer of gold, total reflection of light is observed beyond a critical angle, however the electromagnetic field component of the light penetrates into the medium of lower refractive index creating an evanescent wave and a sharp shadow (surface plasmon resonance). This is due to the resonance energy transfer between the wave and the surface plasmons. The resonance conditions are influenced by the material absorbed on the thin metal film and nucleic acid molecules, proteins and sugars concentrations are able to be measured based on the relation between resonance units and mass concentration.

The production or presence of target nucleic acids and nucleic acid sequences may also be detected and monitored by lateral flow devices. Lateral Flow devices are well known. These devices generally include a solid phase fluid permeable flow path through which fluid flows through by capillary force. Examples include, but are not limited to, dipstick assays and thin layer chromatographic plates with various appropriate coatings. Immobilized on the flow path are various binding reagents for the sample, binding partners or conjugates involving binding partners for the sample and signal producing systems. Detection of samples can be achieved in several manners; enzymatic detection, nanoparticle detection, calorimetric detection, and fluorescence detection, for example. Enzymatic detection may involve enzyme-labeled probes that are hybridized to complementary or substantially complementary nucleic aid targets on the surface of the lateral flow device. The resulting complex can be treated with appropriate markers to develop a readable signal. Nanoparticle detection involves bead technology that may use colloidal gold, latex and paramagnetic nanoparticles. In one example, beads may be conjugated to an anti-biotin antibody. Target sequences may be directly biotinylated, or target sequences may be hybridized to a sequence specific biotinylated probes. Gold and latex give rise to colorimetric signals visible to the naked eye and paramagnetic particles give rise to a non-visual signal when excited in a magnetic field and can be interpreted by a specialized reader.

Fluorescence-based lateral flow detection methods are also known, for example, dual fluorescein and biotin-labeled oligo probe methods, UPT-NALF utilizing up-converting phosphor reporters composed of lanthanide elements embedded in a crystal (Corstjens et al., Clinical Chemistry, 47:10, 1885-1893, 2001), as well as the use of quantum dots.

Nucleic acids can also be captured on lateral flow devices. Means of capture may include antibody dependent and antibody independent methods. Antibody-dependent capture generally comprises an antibody capture line and a labeled probe that is complementary or substantially complementary sequence to the target. Antibody-independent capture generally uses non-covalent interactions between two binding partners, for example, the high affinity and irreversible linkage between a biotinylated probe and a streptavidin line. Capture probes may be immobilized directly on lateral flow membranes. Both antibody dependent and antibody independent methods may be used in multiplexing.

The production or presence of target nucleic acids and nucleic acid sequences may also be detected and monitored by multiplex DNA sequencing. Multiplex DNA sequencing is a means of identifying target DNA sequences from a pool of DNA. The technique allows for the simultaneous processing of many sequencing templates. Pooled multiple templates can be resolved into individual sequences at the completion of processing. Briefly, DNA molecules are pooled, amplified and chemically fragmented. Products are fractionated by size on sequencing gels and transferred to nylon membranes. The membranes are probed and autoradiographed using methods similar to those used in standard DNA sequencing techniques (Church et al., Science 1998 Apr. 8; 240(4849): 185-188). Autoradiographs can be evaluated and the presence of target nucleic acid sequence can be quantified.

Kits

Kits used for the present methods may comprise, for example, one or more polymerases, forward and reverse templates, and one or more nicking enzymes, as described herein. Where one target is to be amplified, one or two nicking enzymes may be included in the kit. Where multiple target sequences are to be amplified, and the templates designed for those target sequences comprise the nicking enzyme binding sites for the same nicking enzyme, then one or two nicking enzymes may be included. Or, where the templates are recognized by different nicking enzymes, more nicking enzymes may be included in the kit, such as, for example, 3 or more.

The kits used for the present methods may also comprise one or more of the components in any number of separate containers, packets, tubes, vials, microtiter plates and the like, or the components may be combined in various combinations in such containers.

The components of the kit may, for example, be present in one or more containers, for example, all of the components may be in one container, or, for example, the enzymes may be in a separate container from the templates. The components may, for example, be lyophilized, freeze dried, or in a stable buffer. In one example, the polymerase and nicking enzymes are in lyophilized form in a single container, and the templates are either lyophilized, freeze dried, or in buffer, in a different container. Or, in another example, the polymerase, nicking enzymes, and the templates are, in lyophilized form, in a single container. Or, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits used for the present methods may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods, such as, for example, reagents used for FRET, lateral flow devices, dipsticks, fluorescent dye, colloidal gold particles, latex particles, a molecular beacon, or polystyrene beads.

An advantage of the present methods and the present kits is that they can be used in any device that provides a constant temperature, including thermocyclers, incubation ovens, water baths, and heat blocks.

Thus, provided in the present methods is method for nucleotide sequence amplification, which comprises: combining a target nucleic acid having a target nucleotide sequence with (i) a polymerase, (ii) a first template nucleic acid that hybridizes to a first strand of the target nucleotide sequence, and (iii) a second template nucleic acid that hybridizes to the complement of the first strand of the target nucleotide sequence, in an amplification reaction, under conditions in which the polymerase extends the template nucleic acids, thereby generating extended template nucleic acid amplicons; wherein: the target nucleotide sequence is between 20 and 40 nucleotides in length; the target nucleotide sequence is amplified 1E+6-fold or more in about ten minutes; and the foregoing steps are conducted under substantially isothermal conditions.

Also provided is a method for nucleotide sequence amplification, which comprises: combining a target nucleic acid having a target nucleotide sequence with (i) a polymerase, (ii) a first template nucleic acid that hybridizes to the a first strand of the target nucleotide sequence, and (iii) a second template nucleic acid that hybridizes to the complement of the first strand of the target nucleotide sequence, in an amplification reaction, under conditions in which the polymerase extends the template nucleic acids, thereby generating extended template nucleic acid amplicons; wherein: the target nucleotide sequence is between 20 and 40 nucleotides in length; the first template comprises a nucleic acid sequence comprising a first template recognition region at the 3' end that is complementary or substantially complementary to the 3' end of the first strand of the target nucleotide sequence; the second template comprises a nucleotide sequence comprising a second template recognition region at the 3' end that is complementary or substantially complementary to the 3' end of the complement of the first strand of the target nucleotide sequence; the target nucleotide sequence comprises from 1 to 5 nucleotides more than the sum of the nucleotides of the first template recognition region and the second template recognition region; the target nucleotide sequence is amplified 1E+6-fold or more in about ten minutes; and the foregoing steps are conducted under substantially isothermal conditions.

Also provided is a method for nucleotide sequence amplification, which comprises: combining a target nucleic acid having a target nucleotide sequence with (i) a polymerase, (ii) a first template nucleic acid that hybridizes to the a first strand of the target nucleotide sequence, and (iii) a second template nucleic acid that hybridizes to the complement of the first strand of the target nucleotide sequence, in an amplification reaction, under conditions in which the polymerase extends the template nucleic acids, thereby generating extended template nucleic acid amplicons; wherein: the first template comprises a nucleic acid sequence comprising a first template recognition region at the 3' end that is complementary or substantially complementary to the 3' end of the first strand of the target nucleotide sequence, wherein the recognition region is 8-15 nucleotides long; the second template comprises a nucleotide sequence comprising a second template recognition region at the 3' end that is complementary or substantially complementary to the 3' end of the complement of the first strand of the target nucleotide sequence, wherein the recognition region is 8-15 nucleotides long; the target nucleotide sequence is amplified 1E+6-fold or more in about ten minutes; and the foregoing steps are conducted under substantially isothermal conditions.

In certain aspects of the present methods, the first template comprises a nucleic acid sequence comprising a first template recognition region at the 3' end that is complementary or substantially complementary to the 3' end of the first strand of the target nucleotide sequence; and the second template comprises a nucleotide sequence comprising a second template recognition region at the 3' end that is complementary or substantially complementary to the 3' end of the complement of the first strand of the target nucleotide sequence. In certain aspects, the target nucleotide sequence comprises from 1 to 5 nucleotides more than the sum of the nucleotides of the first template recognition region and the second template recognition region. In other aspects, the first template and second templates comprise nicking enzyme binding sites and nicking sites upstream of the recognition regions, and the amplification reaction further comprises one or more nicking enzymes that are capable of nicking at the nicking site of said forward and said reverse templates, wherein either one nicking enzyme is capable of nicking both of said templates, or each template is capable of being nicked by at least one of the nicking enzymes, and wherein said one or more nicking enzymes do not nick within said target sequence.

In some embodiments, the target nucleotide sequence comprises 1 nucleotide more than the sum of the nucleotides of the first template recognition region and the second template recognition region. In other embodiments, the target nucleotide sequence comprises 2 nucleotides more than the sum of the nucleotides of the first template recognition region and the second template recognition region. In yet other embodiments, the target nucleotide sequence comprises 3 nucleotides more than the sum of the nucleotides of the first template recognition region and the second template recognition region.

In certain aspects of the present methods, the target nucleic acid is double stranded or single stranded. In certain aspects, the target nucleic acid is double-stranded DNA. In other aspects, the target nucleic acid is single-stranded DNA. In yet other aspects, the target nucleic acid is RNA. The target nucleic acid may be, for example, selected from the group consisting of genomic DNA, plasmid DNA, viral DNA, mitochondrial DNA, and synthetic double-stranded DNA. The target nucleic acid may be, for example, selected from the group consisting of viral DNA, cDNA, and synthetic single-stranded DNA. The target nucleic acid may be, for example, selected from the group consisting of messenger RNA, viral RNA, ribosomal RNA, transfer RNA, micro RNA, micro RNA precursor, and synthetic RNA.

In the present methods, the DNA polymerase may be, for example, a thermophilic polymerase. The polymerase may, for example, be selected from the group consisting of Bst (large fragment), 9°N, Vent$_R$® (exo-) DNA Polymerase, Therminator, and Therminator II. In certain aspects, the polymerase is Bst (large fragment).

In certain embodiments, the first and second templates comprise nicking enzyme binding sites recognized by the same nicking enzyme and said first and said second nicking enzyme are the same. The nicking enzymes may be, for example, selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, and Nt.Bpu10I.

In some aspects of the present method, the portion of the nucleic acid sequence of the first strand that is complementary or substantially complementary to the first strand of the target nucleotide sequence is 8-15 nucleotides in length and wherein the portion of the second strand that is complementary or substantially complementary to the target nucleotide sequence is 8-15 nucleotides in length. In some aspects, the first template is provided at the same concentration as the second template. In other aspects, one of the first or second templates is provided at a ratio to the other template at the range of ratios of 1:100 to 100:1. The reactions of the present methods may further comprise a second polymerase. In some aspects, at least one of the first or second polymerases comprises reverse transcriptase activity.

In certain embodiments of the present method, the amplification is conducted between 54° C. and 60° C. In other embodiments, the amplification is conducted between 56° C. and 58° C. In certain embodiments, wherein the amplification reaction is held at a constant temperature for 1 to 10 minutes. In other embodiments, the amplification reaction is held at a constant temperature for 1 to 20 minutes.

The present method may further comprise detecting the amplification product. Thus, in certain aspects, the amplification product is detected by detection method selected from the group consisting of gel electrophoresis, mass spectrometry, SYBR I fluorescence, SYBR II fluorescence, SYBR Gold, Pico Green, TOTO-3, intercalating dye detection, fluorescence resonance energy transfer (FRET), molecular beacon detection, surface capture, capillary electrophoresis, incorporation of labeled nucleotides to allow detection by capture, fluorescence polarization, and lateral flow capture.

In some aspects, at least two target sequences are capable of being amplified. In certain aspects, the amplification products are detected on a solid surface. In some aspects, at least one capture probe is immobilized on a solid surface. In some embodiments, at least one of said templates comprises a spacer, blocking group, or a modified nucleotide.

In certain embodiments of the present methods, the target nucleotide sequence is amplified 1E+6-fold or more in about five minutes. In other embodiments, the target nucleotide sequence is amplified 1E+6-fold or more in about 2.5 minutes. In other embodiments, the target nucleotide sequence is amplified 1E+7-fold or more in about five minutes. In other embodiments, the target nucleotide sequence is amplified 1E+8-fold or more in about five minutes. In yet other embodiments, wherein the target nucleotide sequence is amplified 1E+9-fold or more in about five minutes.

The present methods also include a method for amplifying a double-stranded nucleic acid target sequence, comprising contacting a target DNA molecule comprising a double-stranded target sequence, having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme binding site and a nicking site upstream of said recognition region and a stabilizing region upstream of said nicking site, wherein the portion of the nucleic acid sequence that is complementary to the 3' end of the target antisense strand is 8-15 nucleotides in length; said reverse template comprises a nucleotide sequence comprising recognition region at the 3' end that is complementary to the 3' end of the target sequence sense strand, a nicking enzyme binding site and a nicking site upstream of said recognition region, and a stabilizing region upstream of said nicking site, wherein the portion of the nucleic acid sequence that is complementary to the 3' end of the target antisense strand is 8-15 nucleotides in length; providing a first nicking enzyme that is capable of nicking upstream, downstream, or at the nicking site of said forward template, and does not nick within said target sequence; providing a second nicking enzyme that is capable of nicking upstream, downstream, or at the nicking site of said reverse template and does not nick within said target sequence; and providing a DNA polymerase;
under essentially isothermal conditions, wherein amplification is performed by multiple cycles of said polymerase extending said forward and reverse templates along said target sequence producing a double-stranded nicking site, and said nicking enzymes nicking at said nicking sites, or amplified copies of said sites, producing an amplification product.

Also provided is a method for amplifying a single-stranded nucleic acid target sequence, comprising contacting a target nucleic acid comprising a single-stranded target sequence with a reverse template, wherein said reverse template comprises a nucleic acid sequence comprising a recognition region at the 3' end that is complementary to the 3' end of the target sequence, a nicking enzyme binding site and a nicking site upstream of said recognition region, and a stabilizing region upstream of said nicking site, wherein the portion of the nucleic acid sequence that is complementary to the 3' end of the target sequence is 8-15 nucleotides in length; providing a first nicking enzyme that is capable of nicking at the nicking site of said reverse template, and does not nick within said target sequence; providing a DNA polymerase under conditions wherein said polymerase extends said reverse template along said target sequence; contacting said extended reverse template with a forward template, wherein said forward template comprises a recognition region at the 3' end that is complementary to the 3' end of the extended reverse template, a nicking enzyme binding site and a nicking site upstream of said recognition region, and a stabilizing region upstream of said nicking site, wherein the portion of the nucleic acid sequence that is complementary to the 3' end of the target antisense strand is 8-15 nucleotides in length; providing a second nicking enzyme that is capable of nicking at the nicking site of said forward template and does not nick within said target sequence or within the complement of said target sequence; wherein the amplification is conducted under essentially isothermal conditions wherein amplification is performed by multiple cycles of said polymerase extending said forward and reverse templates along said target sequence, producing double-stranded nicking sites, and said nicking enzymes nicking at said nicking sites, producing an amplification product. In some aspects of the present method, the DNA polymerase is a thermophilic polymerase. For example, the polymerase may be selected from the group consisting of Bst (large fragment), 9°N, Vent$_R$® (exo-) DNA Polymerase, Therminator, and Therminator II. In certain aspects, the polymerase is Bst(large fragment).

In certain aspects, the nicking enzymes nick downstream of the nicking enzyme binding site. In other aspects, the forward and reverse templates comprise nicking enzyme binding sites recognized by the same nicking enzyme and said first and said second nicking enzymes are the same. In certain aspects, the nicking enzymes are selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, and Nt.Bpu10I.

In some embodiments of the present methods, the target sequence comprises from 1 to 5 nucleotides more than the sum of the nucleotides of said forward template recognition region and said reverse template recognition region. In certain embodiments, the target sequence comprises 1 nucleotide more than the sum of the nucleotides of said forward template recognition region and said reverse template recognition region. In other embodiments, the target sequence comprises 2 nucleotides more than the sum of the nucleotides of said forward template recognition region and said reverse template recognition region.

In certain aspects, the target DNA molecule is selected from the group consisting of genomic DNA, plasmid, mitochondrial, and viral DNA. In other aspects, the target nucleic acid is selected from the group consisting of viral DNA, messenger RNA, microRNA, and microRNA precursors. In other aspects, the forward template is provided at the same concentration as the reverse template. In yet other aspects, one of the forward or reverse templates is provided at a ratio to the other template at the range of ratios of 1:100 to 100:1

In certain embodiments, the present method further comprises a second polymerase. For example, at least one of the polymerases may comprise reverse transcriptase activity. In certain aspects, the amplification is conducted between 54° C. and 60° C. In other aspects, the amplification reaction is held at a constant temperature for 1 to 10 minutes.

The present method may further comprise detecting the amplification product. For example, the amplification product may be detected by a method selected from the group consisting of gel electrophoresis, mass spectrometry, SYBR I fluorescence, SYBR II fluorescence, SYBR Gold, Pico Green, TOTO-3, intercalating dye detection, FRET, molecular beacon detection, surface capture, capillary electrophoresis, incorporation of labeled nucleotides to allow detection by capture, fluorescence polarization, and lateral flow capture.

In certain aspects, at least two target sequences are capable of being amplified. In other aspects, the amplification products are detected on a solid surface. In some aspects, at least one capture probe is immobilized on a solid surface. In other aspects, at least one of said templates comprises a spacer, blocking group, or a modified nucleotide.

The present methods also include a method for amplifying a double-stranded nucleic acid target sequence, comprising contacting a target DNA molecule comprising a double-stranded target sequence, having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme binding site and a nicking site upstream of said recognition region and a stabilizing region upstream of said nicking site; said reverse template comprises a nucleotide sequence comprising a recognition region at the 3' end that is complementary to the 3' end of the target sequence sense strand, a nicking enzyme binding site and a nicking site upstream of said recognition region, and a stabilizing region upstream of said nicking site; and said target sequence comprises from 1 to 5 nucleotides more than the sum of the nucleotides of said forward template recognition region and said reverse template recognition region; providing a first nicking enzyme that is capable of nicking at the nicking site of said forward template, and does not nick within said target sequence; providing a second nicking enzyme that is capable of nicking at the nicking site of said reverse template and does not nick within said target sequence; and providing a DNA polymerase; under essentially isothermal conditions, wherein amplification is performed by multiple cycles of said polymerase extending said forward and reverse templates along said target sequence producing a double-stranded nicking site, and said nicking enzymes nicking at said nicking sites, or amplified copies of said sites, producing an amplification product.

Also provided is a method for amplifying a single-stranded nucleic acid target sequence, comprising contacting a target nucleic acid comprising a single-stranded target sequence with a reverse template, wherein said reverse template comprises a nucleic acid sequence comprising a recognition region at the 3' end that is complementary to the 3' end of the target sequence, a nicking enzyme binding site and a nicking site upstream of said recognition region, and a stabilizing region upstream of said nicking site, wherein the portion of the nucleic acid sequence that is complementary to the 3' end of the target sequence is 8-15 nucleotides in length; providing a first nicking enzyme that is capable of nicking at the nicking site of said reverse template, and does not nick within said target sequence; providing a DNA polymerase under conditions wherein said polymerase extends said reverse template along said target sequence; contacting said extended reverse template with a forward template, wherein said forward template comprises a recognition region at the 3' end that is complementary to the 3' end of the extended reverse template, a nicking enzyme binding site and a nicking site upstream of said recognition region, and a stabilizing region upstream of said nicking site, wherein said target sequence comprises from 1 to 5 nucleotides more than the sum of the nucleotides of said forward template recognition region and said reverse template recognition region; providing a second nicking enzyme that is capable of nicking at the nicking site of said forward template and does not nick within said target sequence or within the complement of said target sequence; wherein the amplification is conducted under essentially isothermal conditions wherein amplification is performed by multiple cycles of said polymerase extending said forward and reverse templates along said target sequence, producing double-stranded nicking sites, and said nicking enzymes nicking at said nicking sites, producing an amplification product.

In certain embodiments, the target sequence comprises 1 nucleotide more than the sum of the nucleotides of said forward template recognition region and said reverse template recognition region. In other embodiments, the target sequence comprises 2 nucleotides more than the sum of the nucleotides of said forward template recognition region and said reverse template recognition region. In other embodiments, the target sequence comprises 3 nucleotides more than the sum of the nucleotides of said forward template recognition region and said reverse template recognition region.

Also provided is a method for amplifying a double-stranded nucleic acid target sequence, comprising contacting a target DNA molecule comprising a double-stranded target sequence, having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme binding site and a nicking site upstream of said recognition region and a stabilizing region upstream of said nicking site; said reverse template comprises a nucleotide sequence comprising a recognition region at the 3' end that is complementary to the 3' end of the target sequence sense strand, a nicking enzyme binding site and a nicking site upstream of said recognition region, and a stabilizing region upstream of said nicking site; providing a first nicking enzyme that is capable of nicking at the nicking site of said forward template, and does not nick within said target sequence; providing a second nicking enzyme that is capable of nicking at the nicking site of said reverse template and does not nick within said target sequence; and providing a DNA polymerase; under essentially isothermal conditions, wherein amplification is performed by multiple cycles of said polymerase extending said forward and reverse templates along said target sequence producing a double-stranded nicking site, and said nicking enzymes nicking at said nicking sites, or amplified copies of said sites, producing an amplification product.

Also provided is method for amplifying a double-stranded nucleic acid target sequence, comprising contacting a target DNA molecule comprising a double-stranded target sequence, having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme binding site and a nicking site upstream of said recognition region and a stabilizing region upstream of said nicking site; said reverse template comprises a nucleotide sequence comprising recognition region at the 3' end that is complementary to the 3' end of the target sequence sense strand, a nicking enzyme binding site and a nicking site upstream of said recognition region, and a stabilizing region upstream of said nicking site; providing a first nicking enzyme that is capable of nicking upstream, downstream, or at the nicking site of said forward template, and does not nick within said target sequence; providing a second nicking enzyme that is capable of nicking upstream, downstream, or at the nicking site of said reverse template and does not nick within said target sequence; and providing a DNA polymerase; under essentially isothermal conditions, wherein amplification is performed by multiple cycles of said polymerase extending said forward and reverse templates along said target sequence producing a double-stranded nicking site, and said nicking enzymes nicking at said nicking sites, or amplified copies of said sites, producing an amplification product.

Also provided is a method for amplifying a double-stranded nucleic acid target sequence, comprising contacting a target DNA molecule comprising a double-stranded target sequence, having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme binding site and a nicking site upstream of said recognition region and a stabilizing region upstream of said nicking site; said reverse template comprises a nucleotide sequence comprising a recognition region at the 3' end that is complementary to the 3' end of the target sequence sense strand, a nicking enzyme binding site and a nicking site upstream of said recognition region, and a stabilizing region upstream of said nicking site; providing a first nicking enzyme that is capable of nicking at the nicking site of said forward template, and does not nick within said target sequence; providing a second nicking enzyme that is capable of nicking at the nicking site of said reverse template and does not nick within said target sequence; and providing a DNA polymerase; under essentially isothermal conditions, wherein amplification is performed by multiple cycles of said polymerase extending said forward and reverse templates along said target sequence producing a double-stranded nicking site, and said nicking enzymes nicking at said nicking sites, or amplified copies of said sites, producing an amplification product, wherein at least a 1E+7 fold amplification of a 22-35 nucleotide long target sequence is obtained when the amplification reaction is run for twelve minutes.

The present method also provides a method for amplifying a double-stranded nucleic acid target sequence, comprising contacting a target DNA molecule comprising a double-stranded target sequence, having a sense strand and an antisense strand, with a forward template and a reverse template, wherein said forward template comprises a nucleic acid sequence comprising a recognition region at the 3' end that is complementary to the 3' end of the target sequence antisense strand; a nicking enzyme binding site and a nicking site upstream of said recognition region and a stabilizing region upstream of said nicking site, wherein the portion of the nucleic acid sequence that is complementary to the 3' end of the target antisense strand is 8-15 nucleotides in length; said reverse template comprises a nucleotide sequence comprising recognition region at the 3' end that is complementary to the 3' end of the target sequence sense strand, a nicking enzyme binding site and a nicking site upstream of said recognition region, and a stabilizing region upstream of said nicking site, wherein the portion of the nucleic acid sequence that is complementary to the 3' end of the target antisense strand is 8-15 nucleotides in length; providing a first nicking enzyme that is capable of nicking upstream, downstream, or at the nicking site of said forward template, and does not nick within said target sequence; providing a second nicking enzyme that is capable of nicking upstream, downstream, or at the nicking site of said reverse template and does not nick within said target sequence; and providing a DNA polymerase; under essentially isothermal conditions, wherein amplification is performed by multiple cycles of said polymerase extending said forward and reverse templates along said target sequence producing a double-stranded nicking site, and said nicking enzymes nicking at said nicking sites, or amplified copies of said sites, producing an amplification product, wherein at least a 1E+7 fold amplification of a 22-35 nucleotide long target sequence is obtained when the amplification reaction is run for twelve minutes.

Also provided are kits for amplifying a nucleic acid target sequence, comprising a DNA polymerase; a first template for nucleic acid amplification, comprising a recognition region at the 3' end that is complementary to the 3' end of a target sequence sense strand; a nicking enzyme binding site and a nicking site upstream of said recognition region; and a stabilizing region upstream of said nicking site, wherein the portion of the nucleic acid sequence that is complementary to the 3' end of the target sequence sense strand is 8-15 nucleotides in length; a second template for nucleic acid amplification, comprising a recognition region at the 3' end that is complementary to the 3' end of the complement of the target sequence sense strand; a nicking enzyme binding site and a nicking site upstream of said recognition region; and a stabilizing region upstream of said nicking site, wherein the portion of the nucleic acid sequence that is complementary to the 3' end of the complement of the target sequence sense strand is 8-15 nucleotides in length; and one or two thermostable nicking enzymes, wherein either one enzyme is capable of nicking at the nicking site of said first and said second templates, or a first enzyme is capable of nicking at the nicking site of said first primer and a second enzyme is capable of nicking at the enzyme site of said second primer.

In certain embodiments, the target sequence comprises from 1 to 5 nucleotides more than the sum of the nucleotides of said first template recognition region and said second template recognition region. In certain embodiments, the polymerase, nicking enzymes, and templates are in a container. In certain embodiments, the polymerase, nicking enzymes, and templates are in two containers. In other embodiments, the polymerase and nicking enzymes are in a first container, and said templates are in a second container. In some aspects, the polymerase, nicking enzymes, and templates are lyophilized. In some aspects, the kits further comprise instructions for following the method of amplification. The kits may further comprise a cuvette. Or, for example, the kits may further comprise a lateral flow device or dipstick. In some aspects, the lateral flow device or dipstick further comprises a capture probe. In some aspects, the kit further comprises a detector component selected from the group consisting of a fluorescent dye, colloidal gold particles, latex particles, a molecular beacon, and polystyrene beads. In some aspects of the kit, at least one of said templates comprises a spacer, blocking group, or a modified nucleotide.

Also provided is a kit for amplifying a nucleic acid target sequence, comprising a DNA polymerase; a first template for nucleic acid amplification, comprising a recognition region at the 3' end that is complementary to the 3' end of a target sequence sense strand; a nicking enzyme binding site and a nicking site upstream of said recognition region; and a stabilizing region upstream of said nicking site; a second template for nucleic acid amplification, comprising a recognition region at the 3' end that is complementary to the 3' end of the complement of the target sequence sense strand; a nicking enzyme binding site and a nicking site upstream of said recognition region; and a stabilizing region upstream of said nicking site, wherein said target sequence comprises from 1 to 5 nucleotides more than the sum of the nucleotides of said first template recognition region and said second template recognition region; and one or two thermostable nicking enzymes, wherein either one enzyme is capable of nicking at the nicking site of said first and said second templates, or a first enzyme is capable of nicking at the nicking site of said first primer and a second enzyme is capable of nicking at the enzyme site of said second primer. In certain aspects of the kit, the portion of the nucleic acid sequence of the first template that is complementary to the 3' end of the target sequence sense strand is 8-15 nucleotides in length, and the portion of the nucleic acid sequence of the second template that is complementary to the 3' end of the complement of the target sequence sense strand is 8-15 nucleotides in length.

In certain embodiments, the polymerase, nicking enzymes, and templates are in two containers. In other embodiments, the polymerase and nicking enzymes are in a first container, and said templates are in a second container. In some aspects, the polymerase, nicking enzymes, and templates are lyophilized. In some aspects, the kits further comprise instructions for following the method of amplification. The kits may further comprise a cuvette. Or, for example, the kits may further comprise a lateral flow device or dipstick. In some aspects, the lateral flow device or dipstick further comprises a capture probe. In some aspects, the kit further comprises a detector component selected from the group consisting of a fluorescent dye, colloidal gold particles, latex particles, a molecular beacon, and polystyrene beads. In some aspects of the kit, at least one of said templates comprises a spacer, blocking group, or a modified nucleotide.

EXAMPLES

Example 1

Sample NEAR™ Amplification Assay

This example provides an example of a typical DNA wet assay of the present method. Those of ordinary skill in the art understand that numerous modifications may be made to the volumes and format of the reaction, the length of time that the assay is conducted, and the amounts of each reactant.

Two 96-well microtiter plates are used to set up "wet" assays, a Template/Target plate and a Master Mix plate. To begin, 5 microliters of templates are aliquoted into appropriate wells on the Template Target plate. For the "−target" wells (control wells without target), 5 microliters of dH$_2$O are added. A reagent master mix is created by combining buffer, salt, dNTPs, enzymes, and dH$_2$O together in a single tube, using appropriate volumes of each based on the number of samples being tested (see Table within this Example). 40 microliters of reagent master mix is aliquoted into both "−target" and "+target" (control wells with target) wells of the Master Mix plate, and the plate is sealed with thermal sealant. All of the previous steps were completed in a pre-amplification room with all of the subsequent steps completed in a post-amplification room. The thermal sealant is removed from the Template/Target plate, from only the wells that target will be added to, leaving the "−wells" sealed to avoid potential contamination. 5 microliters of target is aliquoted into the appropriate "+target" wells. The Template/Target plate is resealed with thermal sealant. Both the Template/Target plate and Master Mix plate are incubated for 2-3 minutes at assay temperature (for example, at 56° C., 57° C., or 58° C., using thermal cyclers. The thermal sealant is removed from both plates. 40 microliters of reagent master mix from the Master Mix plate wells is transferred to the appropriate wells on the Template/Target plate, and the Template/Target plate is resealed with thermal sealant. The samples are incubated for 5-10 minutes at assay temperature. The time for the reaction is calculated from the time that the incubation starts, immediately after the reagent master mix if transferred to the wells on the Template/Target plate, the plate is sealed, and placed in the thermocycler. Reactions are stopped by adding SDS to 0.1% or greater, or by incubating the samples for 2 minutes at 80° C.

To detect the amplified products, for example, 3-5 microliters of 5 micromolar molecular beacon is added to each well and mixed by pipetting up and down several times. A fluorescence read is performed at the appropriate wavelength based on the fluorophore present on the molecular beacon, at assay temperature, following a 1 minute incubation Typical reagent breakdown for single 50 microliter DNA reactions (all volumes in microliters)

| Reagent | −Target | +target | Final Concentration |
| --- | --- | --- | --- |
| 5X IB2 Buffer | 10.0 | 10.0 | 1X |
| 100 mM MgSO$_4$ | 2.5 | 2.5 | 10 + 5 mM |
| 10 mM dNTPs | 1.5 | 1.5 | 0.3 mM |
| 8 U/microliter Bst Pol | 2.4 | 2.4 | 19.2 units |
| 10 U/microliter N. BstNB1 | 1.50 | 1.50 | 15 units |
| Template 1 | 2.5 | 2.5 | 10-1000 nM |
| Template 2 | 2.5 | 2.5 | 10-1000 nM |
| Target | 0 | 5.0 | |
| H$_2$O | 27.1 | 22.1 | |
| Total | 50.0 | 50.0 | |

5xIB2 buffer consists of:
250 mM Tris-HCl (pH8.0)
75 mM (NH$_4$)$_2$SO$_4$
75 mM Na$_2$SO$_4$
50 mM MgSO$_4$
5 mM DTT
0.5% Triton X-100

A typical reaction does not have a standard target concentration, but target copy per reaction may range from 10-50 at the lower end, for example, to 1E+6 copies in the upper end, for example, or more. In terms of molar concentrations, a 50 microliter assay with 10 copies of target is 3.32e−13 micromolar, where a 50 microliter assay with 50 copies of target is 1.66e−12 micromolar and a 50 microliter assay with 1e6 copies of target is 3.32e−8 micromolar.

The target sample may consist of, for example, purified DNA or RNA, that has been resuspended in dH$_2$O or TE, or sample that has not been purified. For example, endocervical swab clinical samples were collected, and sample was eluted and lysed from the swabs using Pierce's Lyse-N-Go PCR reagent (Cat #78882). Lyse-N-Go is a proprietary formulation that is non-ionic detergent based. Aliquots of each eluted/lysed sample were then added directly to assays, and the results indicate no loss of assay activity. Assays have also been conducted using clinical samples that were collected in viral transport media (VTM), either M4 or M5. The samples collected in VTM were mixed with Pierce's Lyse-N-Go PCR reagent to lyse the target cells, and subsequently aliquots of these samples were added to assays without loss of activity. Finally, the assay has been conducted in the presence of various potential inhibitors, such as sand, soil, clay, urine and serum, and each of these inhibitors was well tolerated.

Example 2

Detection of DNA NEAR™ Assay Products by Gel Electrophoresis

Figure 1A:
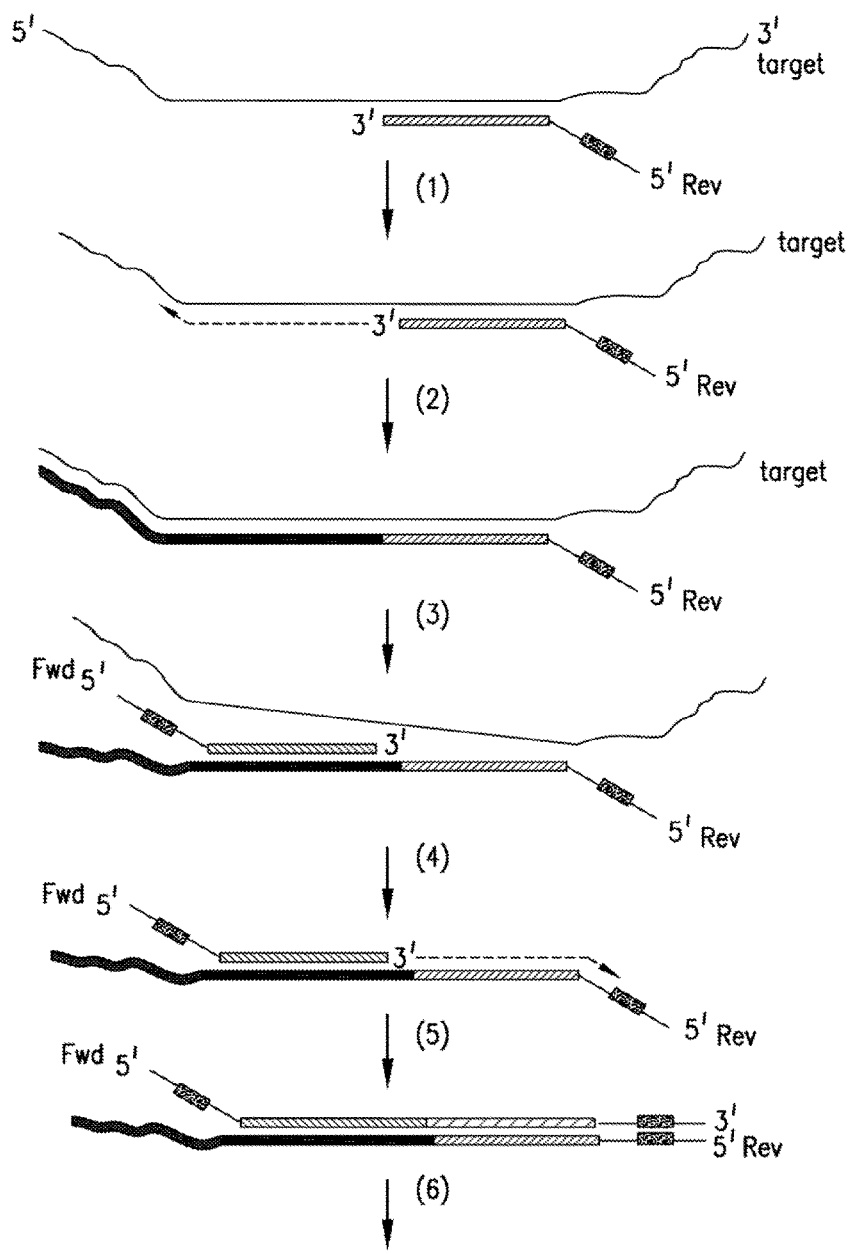
FIGS. 1A-D are graphic drawings depicting mechanisms of the reactions of the present invention.
Figure 1B:
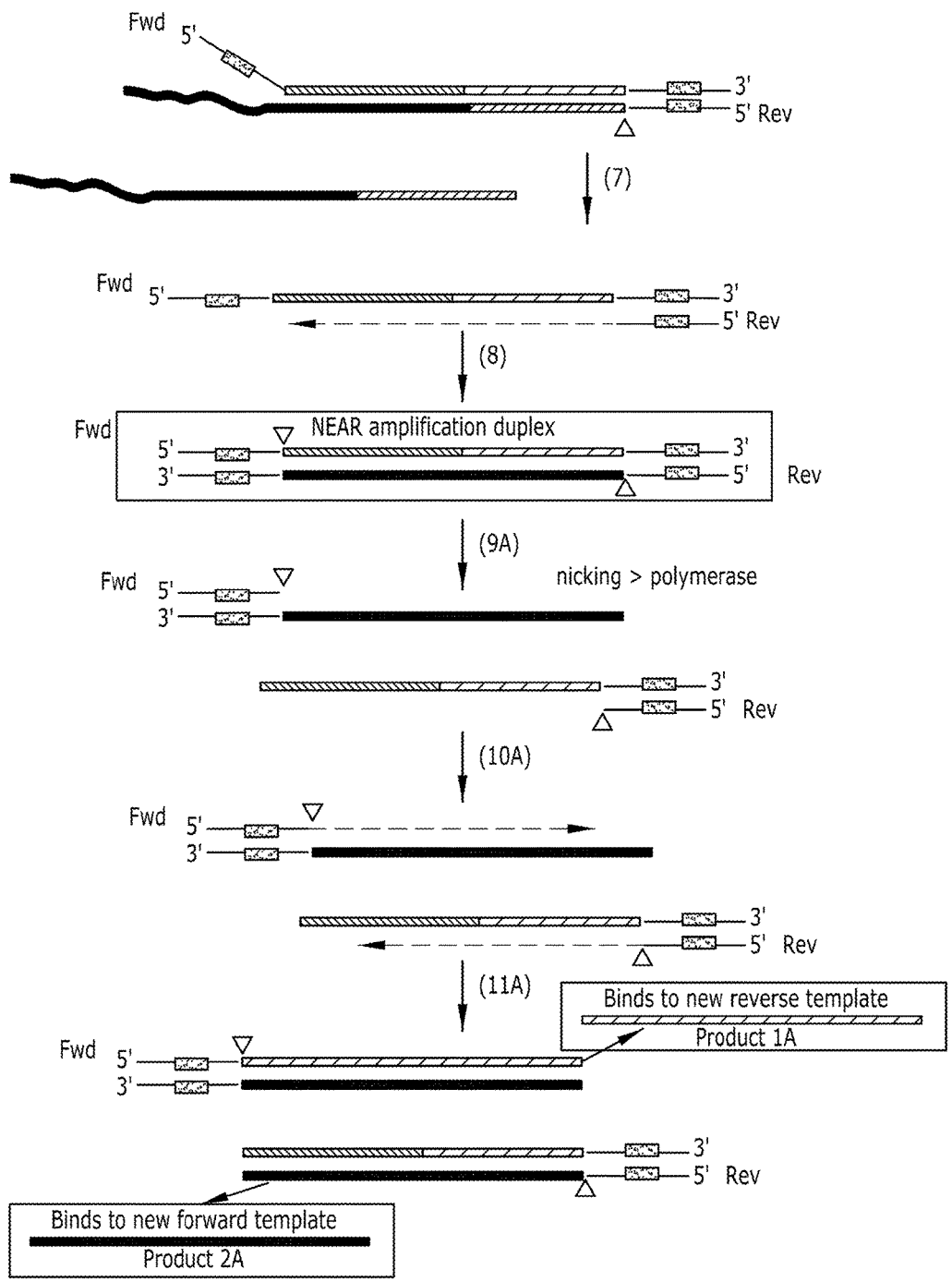
Figure 1C:
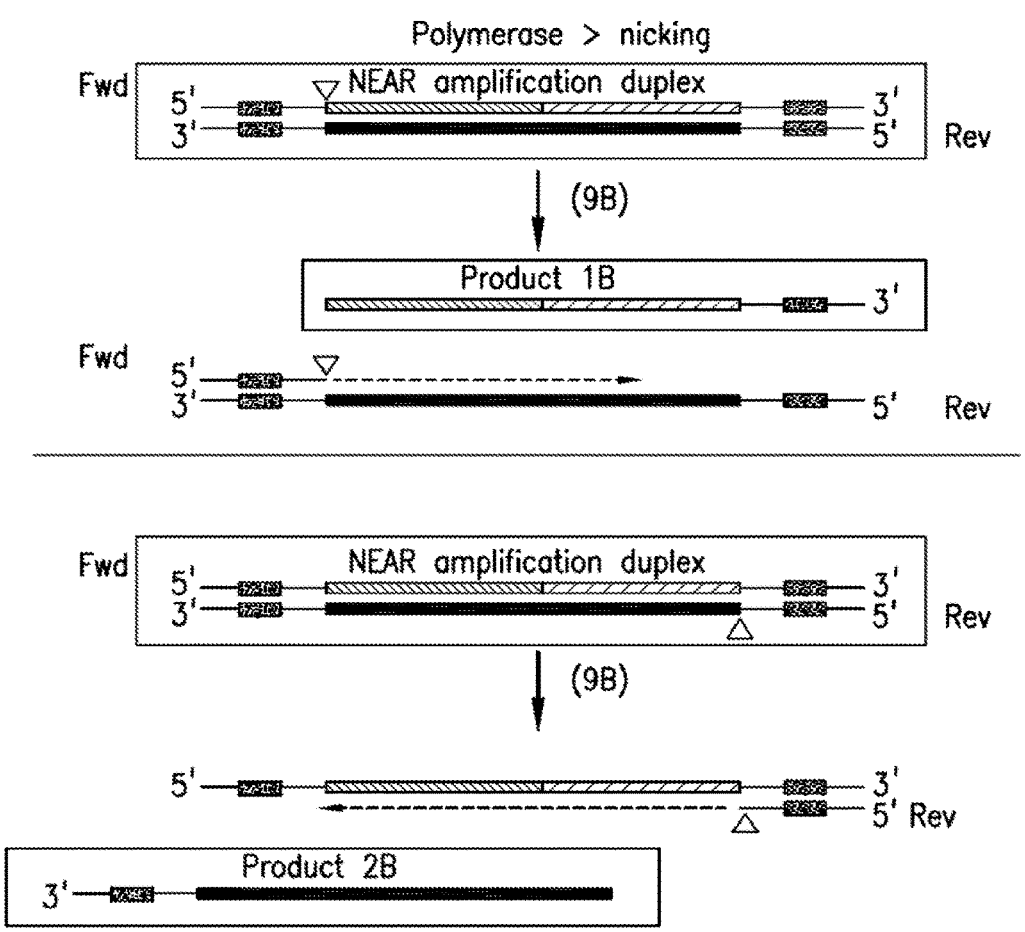
Figure 1D:
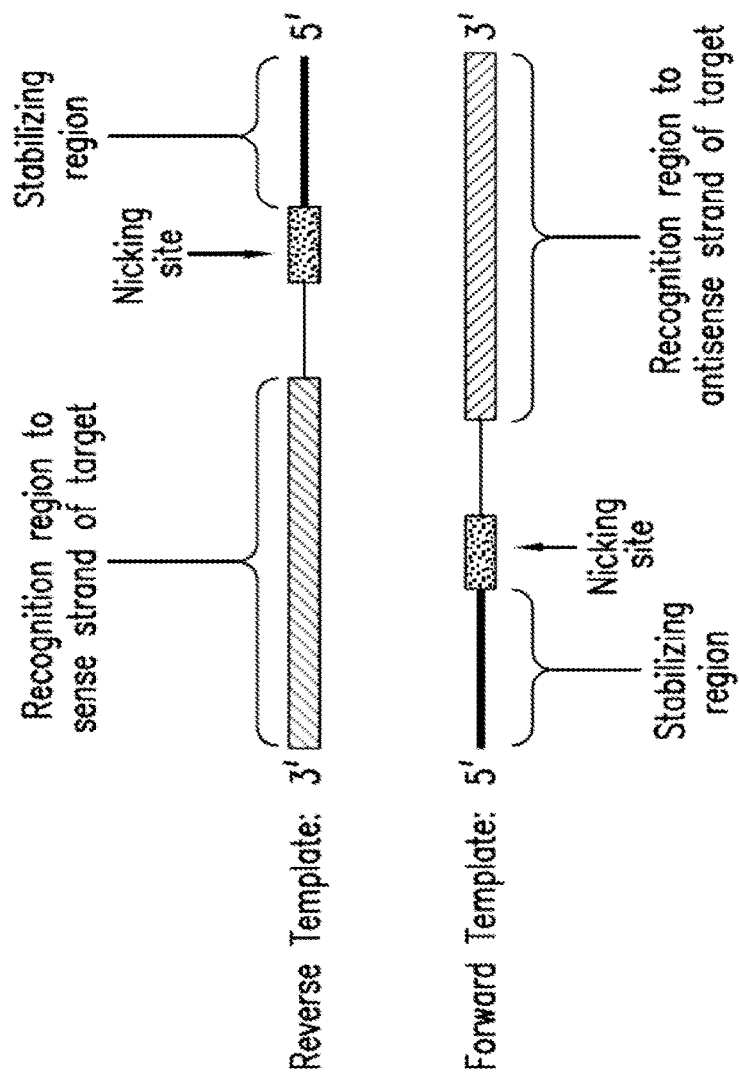
Figure 2:
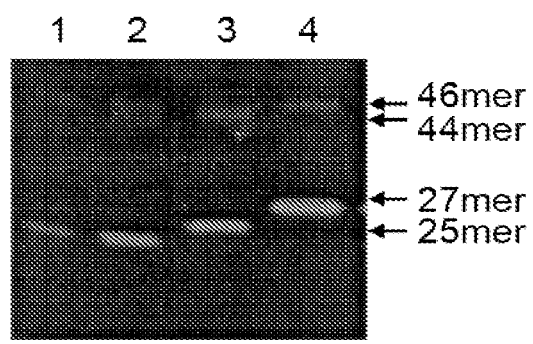
FIG. 2. 20% polyacrylamide gel of reaction products from a DNA NEAR™ assay.

The amplification reaction products can be visualized by gel electrophoresis. In the absence of target, the templates (with complementary or substantially complementary 3' bases) overlap by one or more bases, polymerase extends in each direction to generate the NEAR™ amplification duplex (FIG. 1B); and the amplification proceeds in a similar mechanism to the NEAR™ amplification to amplify a product that is two bases shorter than the target amplified product. In the case of a 25mer assay where the templates end in A and T, the resulting background product is 23 bases. The 27mer assay also forms a 23mer background and 27mer product. Longer reaction products are also amplified. The sequence of these products is hypothesized to be due to the polymerase extension before the nicking enzyme can nick both sides of the NEAR™ amplification duplex, according to Steps 9B in FIG. 1C. FIG. 2 shows the NEAR™ reaction products are easily distinguished from background products by gel electrophoresis.

Example 3

Detection of RNA Assay Products by Gel Electrophoresis

The reaction of the present method can also amplify RNA targets. In this case, the target is Ebola Armored RNA, which is a ~600 base strand of RNA encapsulated by MS2 phage coat proteins to simulate a viral particle. The reaction is designed to amplify a 25-base region of the Ebola genome contained within the encapsulated RNA sequence. Reaction products run on a 20% polyacrylamide gel (FIG. 3) show the amplified 25mer product along with 23mer and 20mer background products. This example demonstrates the ability of the reaction to amplify RNA released from virus-like particles.

Example 4

Detection of DNA and RNA Assay Products by Mass Spectrometry

The reaction amplification products of the present methods can also be detected by mass spectrometry using an ESI/TOF system with a front end LC. The reaction products observed are multiple charged ion species. Usually, the −3 or −4 charge state is the major peak in the spectrum (in the range of 1000-3000 AMU), depending on the length of the oligonucleotide product. The sodium adduct is usually present in the spectrum as a peak adjacent to the major peak at roughly 20-25% the intensity. The unique peaks for the positive reactions in the presence of target are visible in both FIGS. 4 and 5 for the DNA and RNA reactions respectively. The background products formed in these reactions are not shown in the mass range of these spectra.

Example 5

Real-Time Detection of the Assay Amplification

Figure 6:
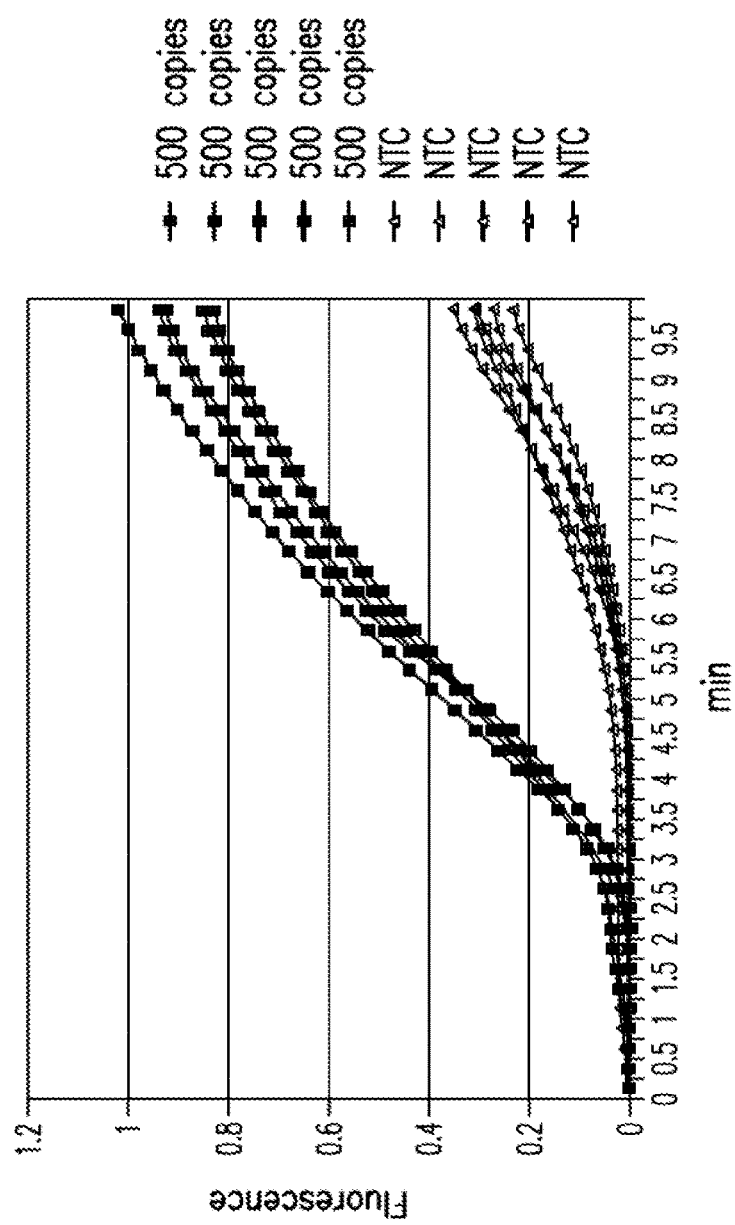

The amplification reaction of the present method can also be monitored, as shown in FIG. 6, in real-time with SYBR II fluorescence. The fluorescence increases as SYBR II intercalates into the amplified double-stranded products. The background products also generate fluorescence at a slower rate than the true product. Optimization of amplification sequence, reaction temperature and reaction buffer conditions are necessary in order to visualize distinct separation between the positive reactions and the negative controls.

Example 6

FRET Detection of Real-Time NEAR™ Assay Amplification

Figure 7:
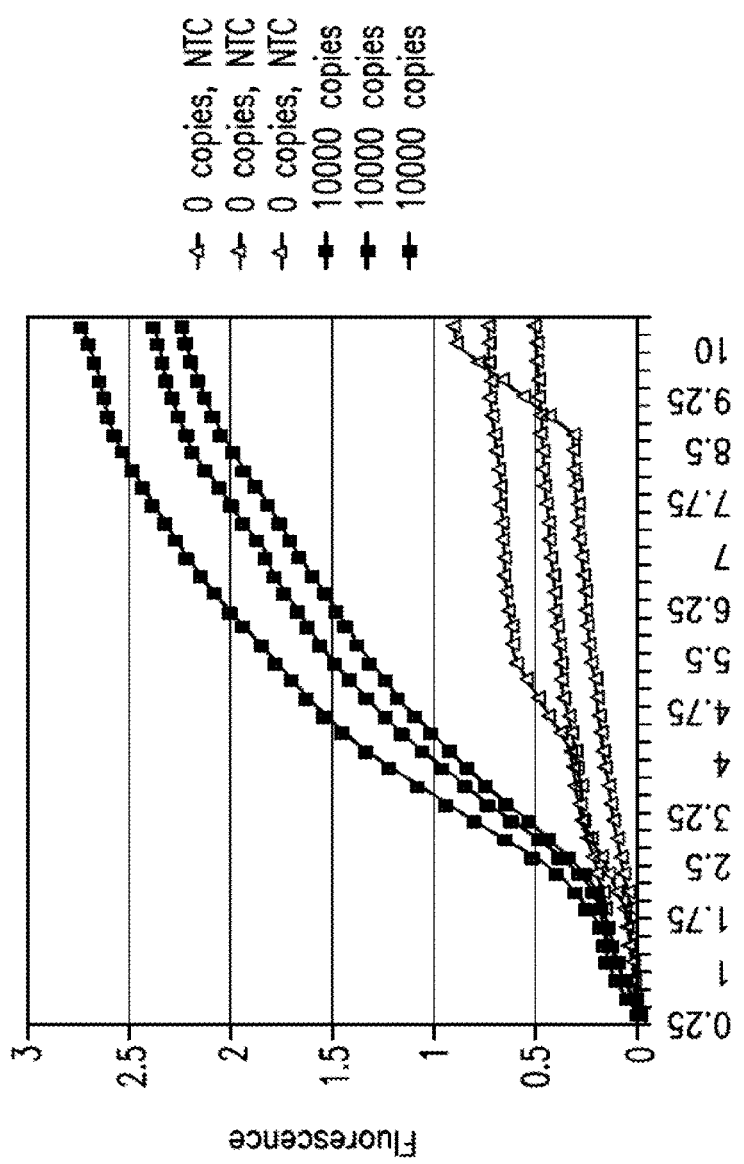

NEAR™ amplification can also be monitored by Fluorescence Resonance Energy Transfer (FRET), as shown in FIG. 7. Amplification occurs using dual labeled templates, one on each end (5'-FAM, 3'-BHQ). Fluorescence is generated from the FAM-labeled oligonucleotide upon cleavage of the template by the nicking enzyme when it becomes double-stranded. Since fluorescence is produced by the initial nicking reaction, this detection method is extremely responsive. Since the 3' ends of the templates are blocked from extension by the quenching label, the production of background fluorescence is inhibited.

Example 7

Molecular Beacon Detection of Real-Time NEAR™ Amplification

Figure 8:
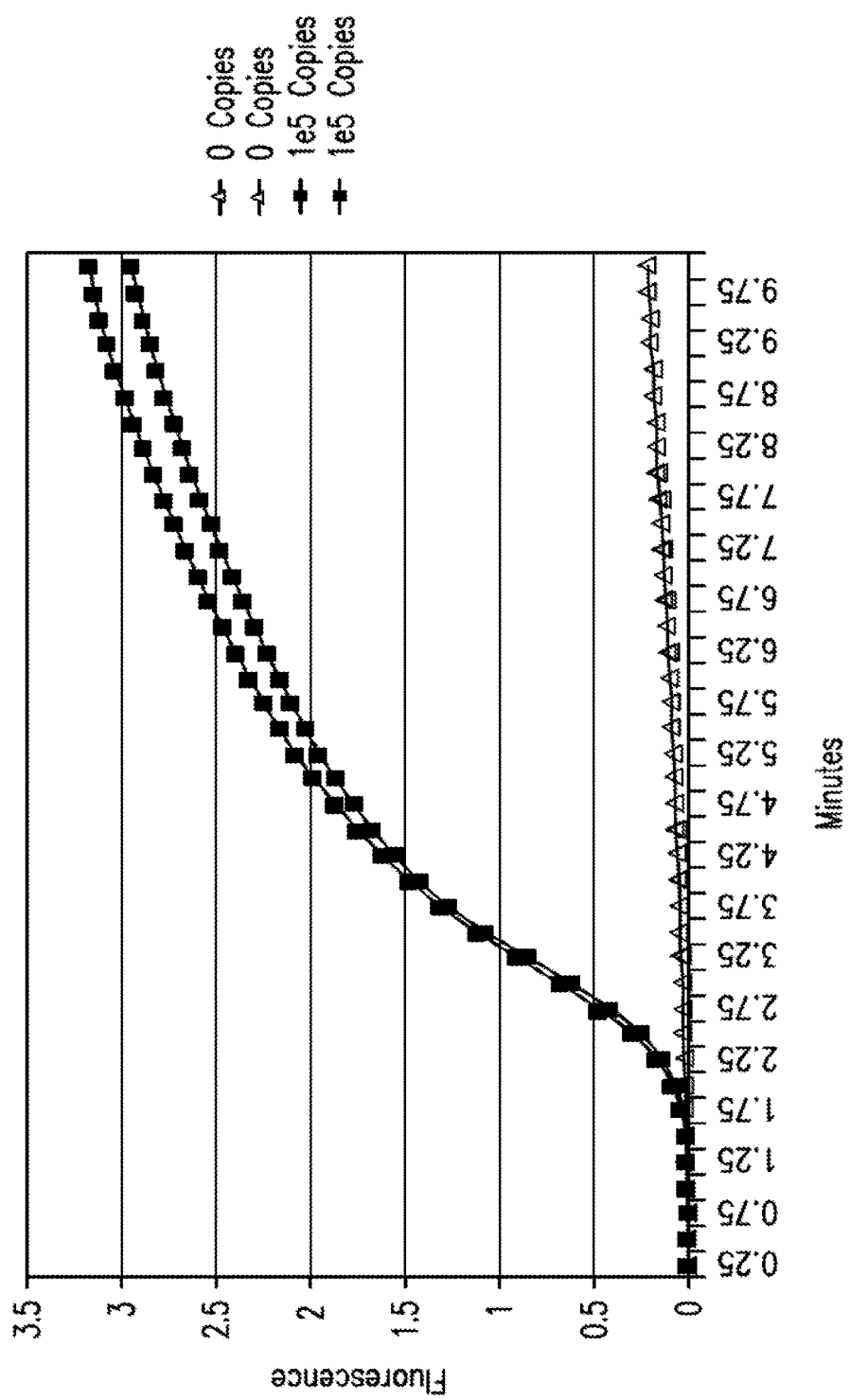

A third method of monitoring real-time amplification is using molecular beacons, as shown in FIG. 8. In this case, the amplified product hybridizes to the loop region of the molecular beacon resulting in an increase in fluorescence from the separation of the fluorophore and quencher on each end of the hairpin stem. Since this interaction occurs post-amplification, it is considered pseudo-real-time and can be slightly slower in response relative to the FRET approach.

Example 8

False Positive Rate Testing

Figure 9:
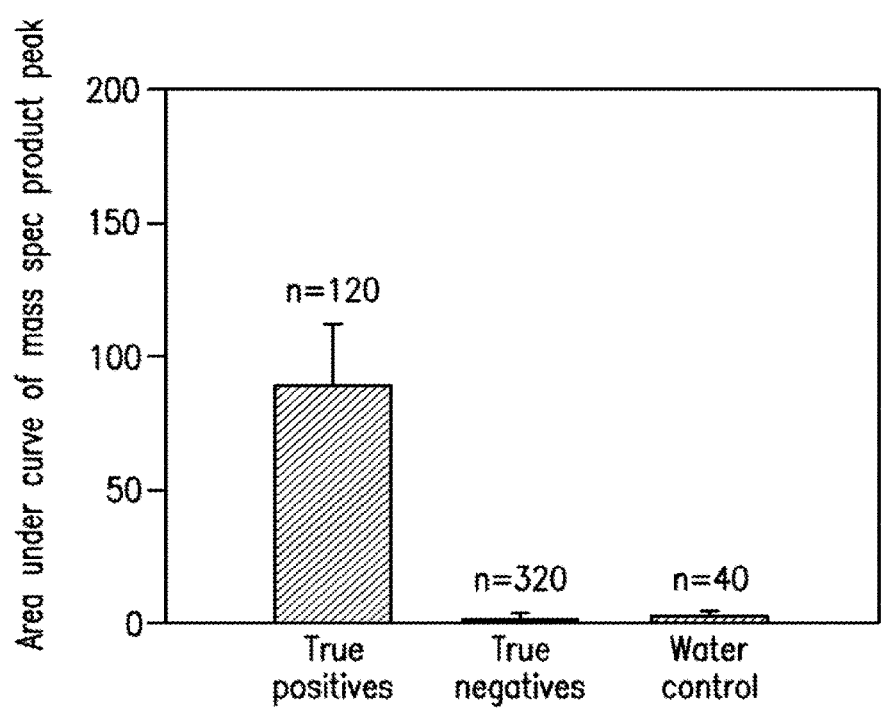

This experiment was designed to probe the probability that the amplification reaction of the present method will yield a true product in the negative reaction, or a false positive. Reactions directed at specific amplification of a 25mer region specific to the *Bacillus subtilis* genome were run in the presence (n=120) and absence (n=320) of *Bacillus subtilis* genomic DNA. End point reactions were run on the mass spectrometer and the area under the curve (AUC) for the product mass peak in the mass spectrum was analyzed. As shown in FIG. 9, the results show that none of the 320 negative reactions resulted in a false positive with AUC values equal to the water control. The true positive AUC values were at least 3 standard deviations apart from the true negatives. Overall, these results demonstrate the reproducible nature of the assays of the present methods.

The *Bacillus subtilis* assay was developed to target a 25 nucleotide region of the mobA-nprE gene region, with the sequence 5'-TTAACGTCTCTAATTTCAGCTTTTG-3' (SEQ ID NO: 1). The templates used to amplify this region were, T1 5'-ATGCATGCATGAGTCACATT-TAACGTCTCTA-3' (SEQ ID NO: 2), and T2 5'-ATGCAT-GCATGAGTCACATCAAAAGCTGAAA-3' (SEQ ID NO: 3). The assay was carried out essentially as described in Example 1, and with the modifications here, for 4 minutes at 56° C. with 10,000 copies of *Bacillus subtilis* genomic DNA plus 100,000 copies of *Bacillus thuringiensis* genomic DNA (True positives), 10,000 copies of *Escherichia coli* genomic DNA plus 100,000 *Bacillus thuringiensis* genomic DNA (True negatives) or no target (water control). Aliquots of each sample were then analyzed by electrospray ionization mass spectrometry to determine the amount of specific product made in each reaction using area under the curve (AUC) calculations.

Example 9

Beacon Detection: Assay Reproducibility with Beacon Detection

Figure 10:
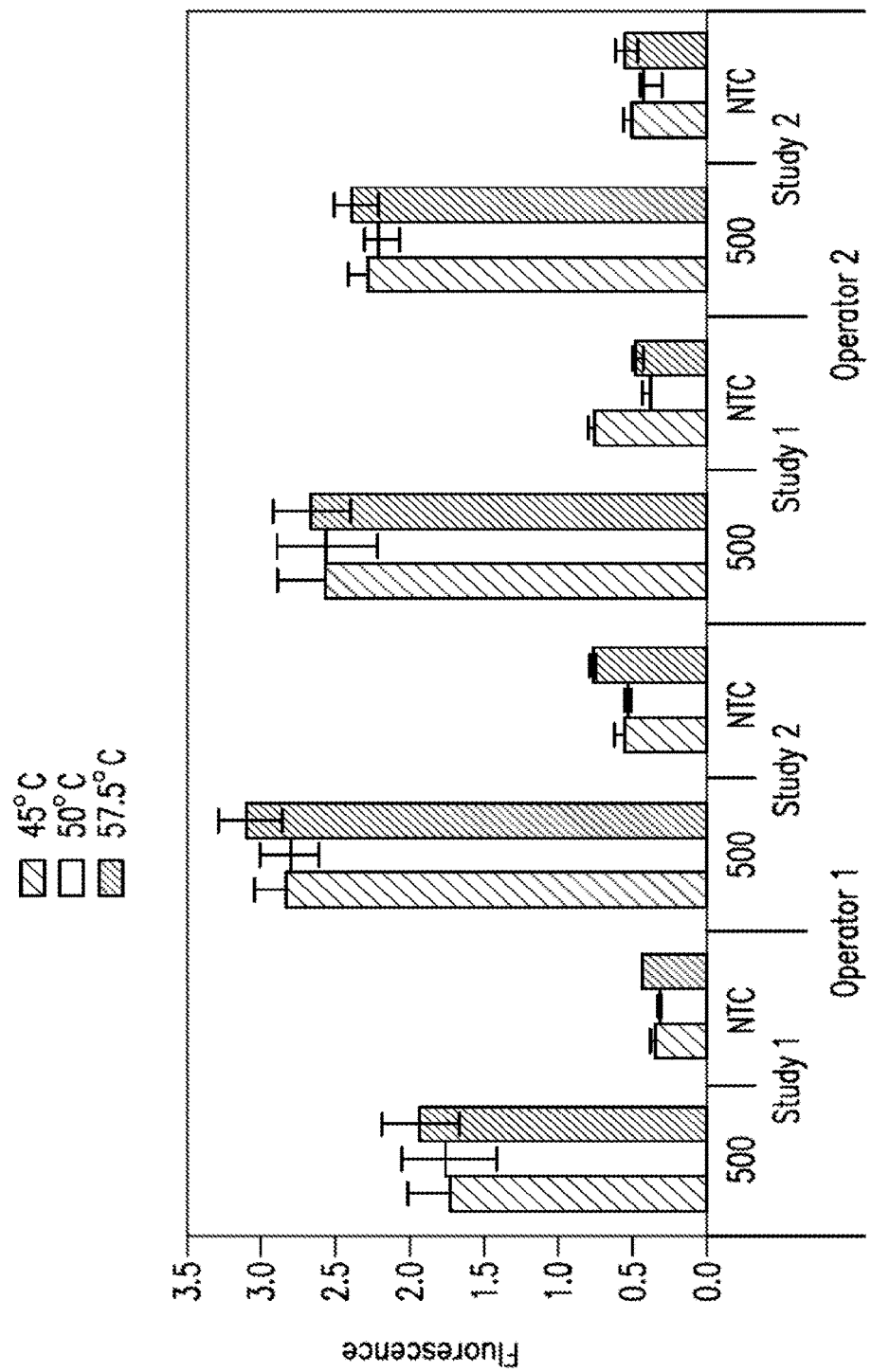

The molecular beacon detection of reaction products of the present method can also be used as an endpoint reading. As shown in FIG. 10, the ratio of reaction products can be manipulated by varying the input ratio of the forward and reverse templates. Skewing the templates to favor one of the reaction products allows the single-stranded product to be available for hybridization to a molecular beacon. The open beacon generates a fluorescent signal. This detection method is extremely reproducible. In this study, two operators performed replicates of the same assay on two different days. The results of this study demonstrate the reproducibility of the assay from one day to the next as well as reproducibility between operators.

Example 10

Assay Sensitivity with Beacon Detection

Figure 11:
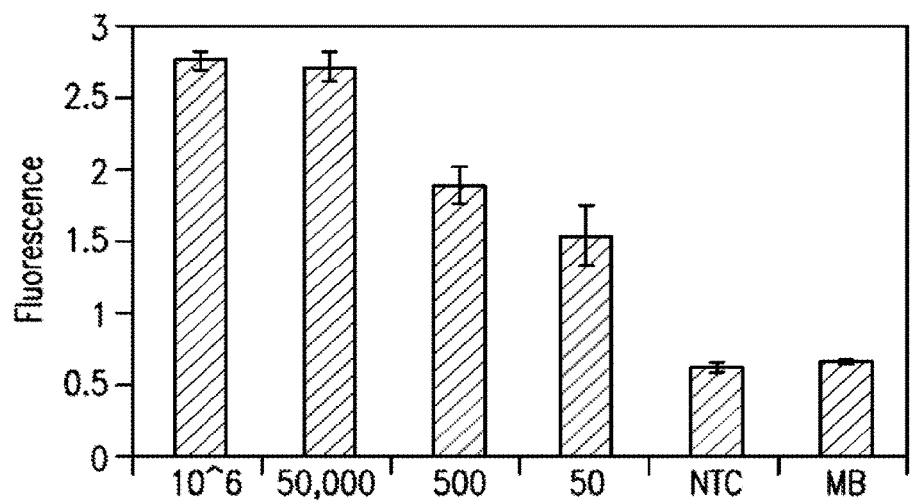

The sensitivity of the assay with beacon read-out was tested using a dilution of *Francisella tularensis* genomic DNA. As shown in FIG. 11, as few as 50 copies were detected above the no target control.

Example 11

Concentration of Amplified Products for DNA Amplification

Figure 12:
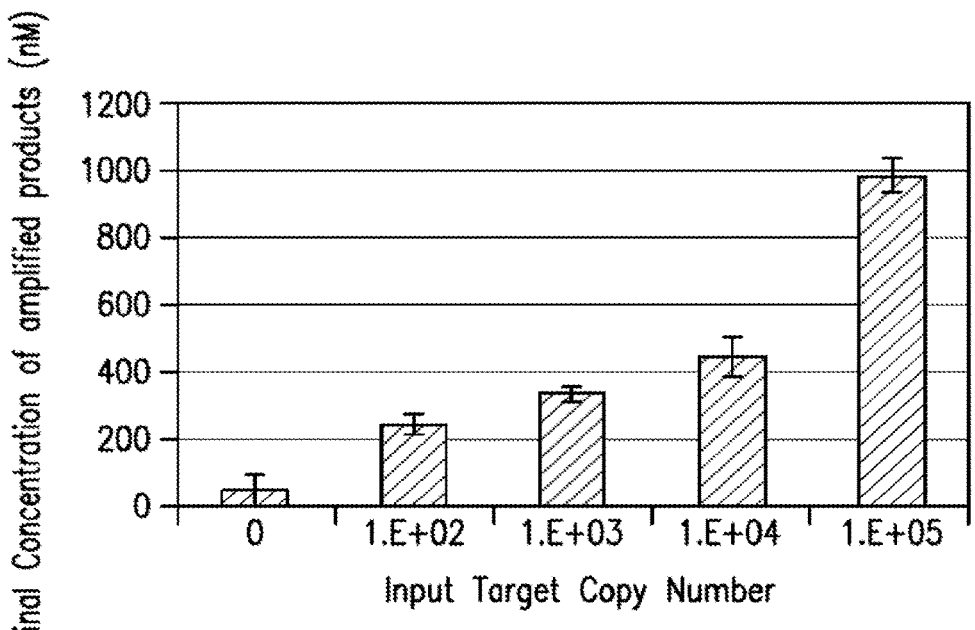

The sensitivity of the assay has also been studied using mass spectrometry detection of the reaction products. FIG. 12 shows signal above the no target control down to 100 copies. The data from this study was used to correlate the input copy number to the final amount of amplified product. In this study, the AUC values of the mass spec product peaks were fit to a standard curve to give the estimated final concentration of amplified product for the assay. The amount of amplified product ranges from approximately 250 nM to almost 1 µM for 1E+2 and 1E+5 copies respectively. This product amount results in a 1E+8 to 7E+10-fold amplification. These reactions were performed without the hot-start conditions, in fact hot-start conditions have been shown to dramatically increase the amount of product amplified, so a further increase in amplification is achieved. The zero copy amplification reaction has a positive final concentration due to the y-intercept value in the standard curve equation.

Example 12

Concentration of Amplified Products for RNA Assay

Figure 13:
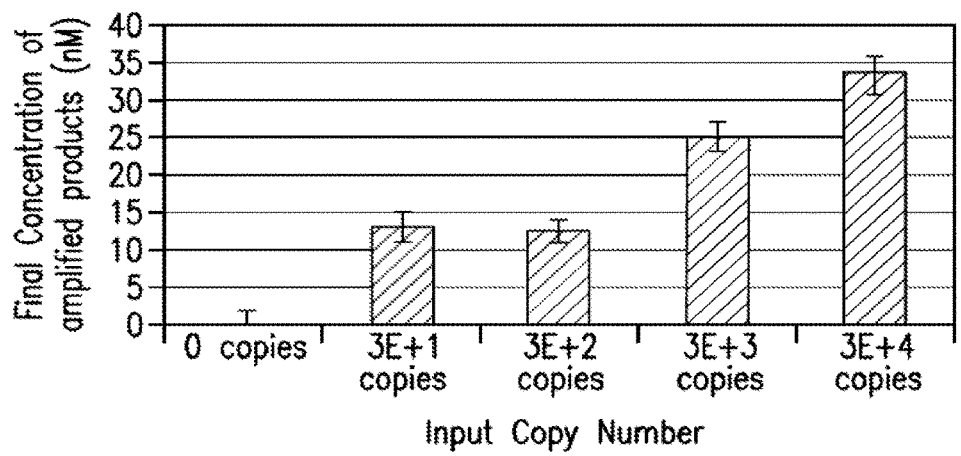

A similar study was performed on the amplification of RNA using the present method. A dilution of RNA targets were amplified by the assay of the present method. Products were run on the mass spec and the AUC values of the product peaks were analyzed against a standard curve to determine the concentration of the final product, as shown in FIG. 13. A 12 minute amplification starting with 30 and 30,000 copies of initial target results in a 3E+9 to 1E+7-fold amplification respectively. The lower extent of amplification compared to the DNA amplification could be due to the less efficient reverse transcriptase ability of the polymerase compared to its replication abilities. Also, the RNA:DNA hybrid formed upon the extension of the reverse template is a stronger interaction compared to a normal DNA:DNA hybrid and will have less breathing to allow for the forward or another reverse template to displace one strand. However, amplification products from the RNA reaction were detected down to <100 copies.

Example 13

NEAR™ Reaction Specificity for DNA

Figure 14:
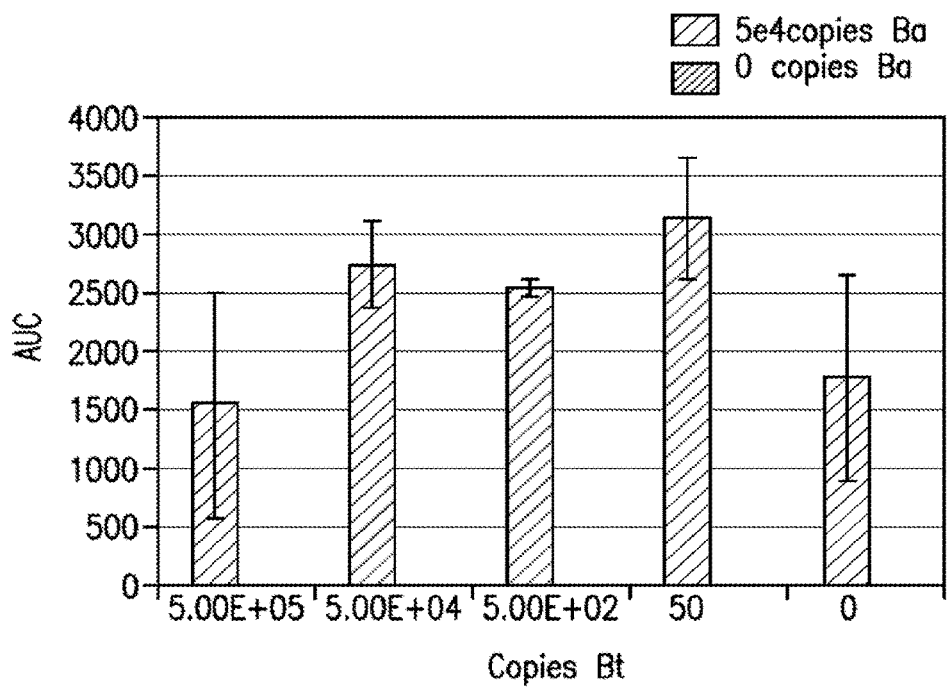
Figure 15:
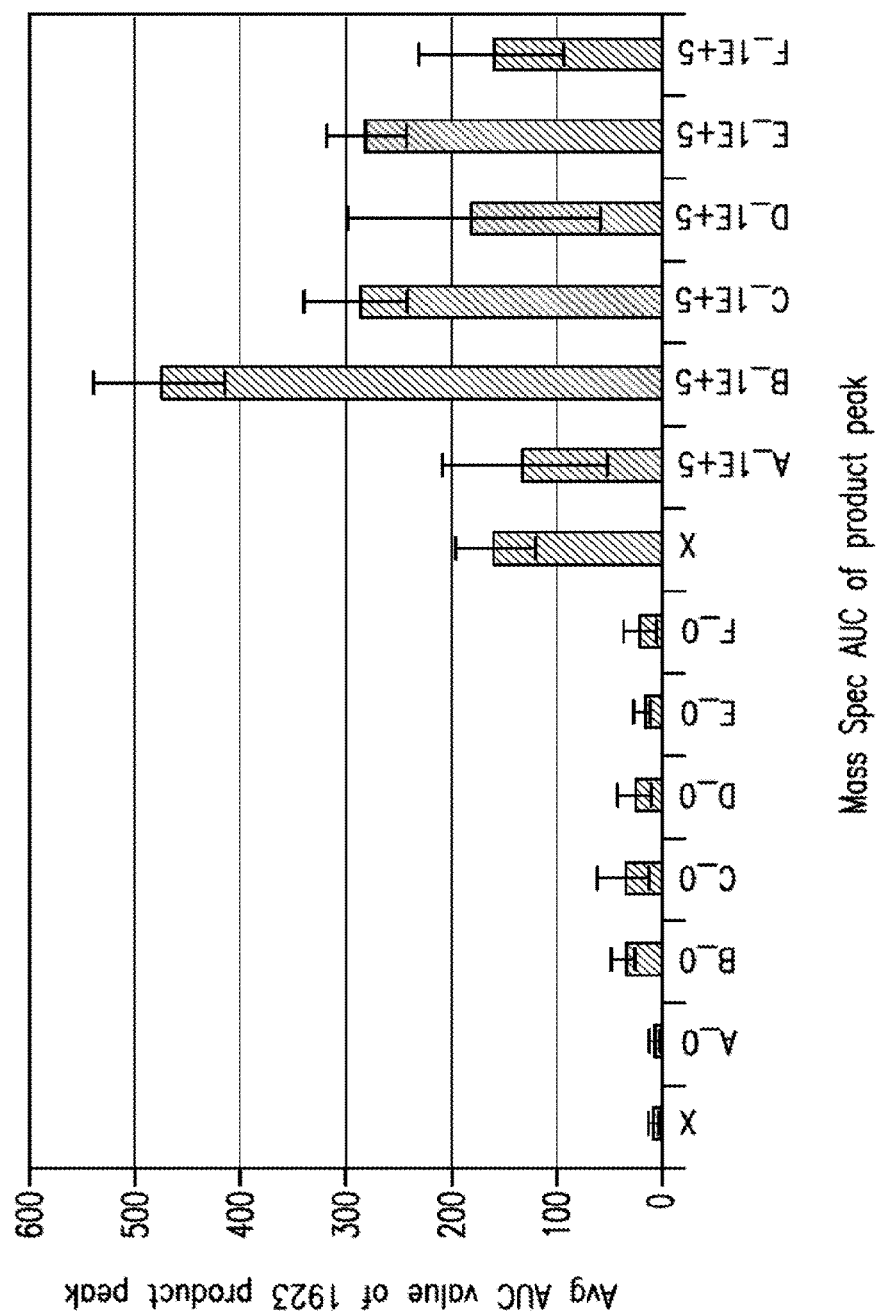
Figure 16:
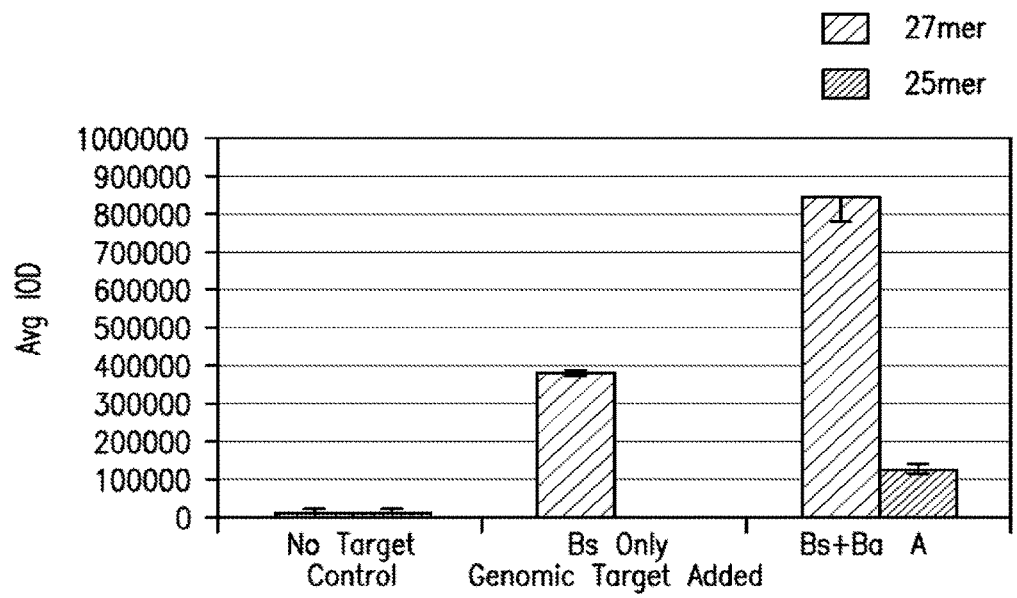

Since the reaction products are usually between 20 and 30 bases in length, the question arises as to whether or not these short amplification assays can be specific enough to target a single sequence region with other near neighbor genomes present. The reaction was tested for its specificity by running the amplification reaction in the presence and absence of varying amounts of the near neighbor genomic DNA (FIG. 14). In this case, the assay detects a specific sequence in the pXO2 plasmid of Bacillus anthracis and the near neighbor genome is Bacillus thuringiensis (kurstaki). The reactions were analyzed by the AUC values for the product peaks. The figure below demonstrates that in the absence of the correct target (*Bacillus anthracis*), there is no true product amplified (the levels are so low that they are not visible on the scale of the graph). The amount of amplification of the positive reactions is consistent, with larger error bars for the 0 and 5E+5 copies of *Bacillus thuringiensis* (5E+4 copies of *Bacillus anthracis*) due to a single lower value for one of the triplicate runs. Overall the experiment demonstrates that the reaction is very specific to the target sequence when the assay is designed within a unique region of the genome.

Example 14

Interferent Testing

A panel of interferents was tested to monitor the effect of each on amplification. FIG. 15 demonstrates the robust nature of the assay of the present method in the presence of interferents. Some interferents that are known to inhibit PCR, such as humic acid, did not appear to inhibit the assay, though the amount of each interferent is unknown. From statistical analysis only interferent B, C, and E were statistically different from the control assay x. In the B, C, and E cases, the difference resulted in increased product amplification.

Example 15

Multiplexing of Two Sequences with DNA Assays

A DNA duplex was designed for capillary electrophoresis (CE) detection. Amplification products were 25 bases (*Bacillus anthracis* assay, Ba) and 27 bases (*Bacillus subtilis* assay, Bs) in length with background production of a 23mer. The reaction was run for 10 minutes in the presence or absence of 5E+5 copies of the respective genomic DNA target. The samples were run on a 20% polyacrylamide gel to visualize the reaction products. FIG. 16 indicates the presence of positive product amplification when *Bacillus subtilis* only is present as well as when both *Bacillus subtilis* and *Bacillus anthracis* are present.

Example 16

DNA Assay Duplex Specificity

The DNA duplex reaction with *Bacillus subtilis* (Bs) and *Bacillus anthracis* (Ba) was shown to be specific to the respective genomes. The assays were run in the presence of the near neighbor, *Bacillus thuringiensis*, as shown in FIG. 17. In the negative reaction where both template sets are present as well as the *Bacillus thuringiensis* genomic DNA, there is no product band in the 25 or 27mer region. Product bands appear only when the specific genomic target is present, which demonstrates the specificity of the duplex reaction.

Example 17

Multiplexing with RNA Assays

An MS2 assay that amplifies a 27mer product and an Ebola assay that amplifies a 25mer product was developed and multiplexed so that all templates are present in each assay and amplification of products is dependent on the target present. This combination of templates forms background products that are 23 bases and 20 bases in length. The gel shown in FIG. 18 demonstrates the ability for the reaction of the present method to amplify multiple RNA targets in a single reaction.

Example 18

Amplification from Lysed Spores

Amplification was performed on semi-processed samples to determine whether it is possible to amplify DNA released from spores through lysis. The negative control reaction contained DNase-treated spores, unlysed, so no DNA should be present to amplify. The positive control reaction contained purified genomic DNA at concentrations around the amount of DNA estimated to be released through lysis. Results in FIG. 19 show that amplification with unlysed DNase-treated spores results in no product amplification as expected, whereas the three samples lysed before amplification resulted in product amounts in the range of the theoretical amounts.

Example 19

Capture and Extension

The reaction products of the present method can also be detected on a solid surface. A capture probe attached at the 5' end to the surface through a biotin/streptavidin attachment can bind to the reaction products from which polymerase extends to form a stable duplex that SYBR and any intercalating dye can detect. The capture probe is designed to favor extension through binding to the true product over background products because the 3' base of the capture probe is complementary to the middle spacer base in the product which is not present in either of the templates or the background products. FIG. 20 demonstrates the increased fluorescence of the products in the presence of the capture probe and polymerase over the average binding (same reaction in the absence of polymerase, to preclude extension of the capture probe) and the no target control where only background products are amplified, but cannot form a stable duplex with the capture probe for polymerase to extend.

Example 20

Surface NEAR™ FRET DNA Assay

The reaction of the present method can also be performed with the templates immobilized on the surface. The templates for FRET detection of surface amplification usually have three modifications: one 5' biotin with a TEG spacer, one FAM fluorophore internal to the biotin, and a quencher on the 3' end which serves to block background amplification as well as to quench the FAM fluorophore. The template is immobilized on the surface through biotin/streptavidin attachment. FIG. 21 demonstrates that with both templates immobilized along with additional mixing, the reaction proceeds at a much slower rate than the solution amplification rate (amplification in 16 minutes for 1E+6 copies of genomic DNA). When a single template is immobilized on the surface and the other template is free in solution, the amplification reaction is increased to 10 minute detection for 1E+6 copies of genomic DNA. Fluorescence from background products is observed ~3.5 minutes after the product signal, similar to what is observed for solution phase kinetics, but slowed considerably.

Example 21

Healthcare Example

*Chlamydia trachomatis* (Ct) Assay

An assay of the present method was performed to detect the presence of a *Chlamydia trachomatis* (Ct) target sequence. A 2-fold dilution series of synthetic DNA containing the target sequence for the Ct P2_2 assay was used to determine the limit of detection of the assay. The reaction was carried out essentially as described in Example 1, with some modifications as described in this example. The dilution series started with 10,000 copies of target DNA, and proceeded to less than 1 copy per reaction. A 'no target' control sample was also included in this experiment. Reactions were performed on a 96-well microtiter plate in 50 microliter volumes in the following buffer: 50 mM Tris-HCl, pH 8.0, 30 mM NaCl, 15 mM $(NH_4)_2(SO_2)$, 15 mM $Mg_2SO_4$, 1 mM DTT, 0.1% Triton X-100 with 0.3 mM dNTPs, 19.2 units of Bst DNA polymerase and 15 units of Nt.BstNBI nicking enzyme. Templates were added at a ratio of 200 nM :100 nM (Template 1: Template 2). Reactions were performed as follows: On plate 1, 5 microliters of template mix was added to each well in a pre-amplification room, and sealed. On plate 2, 40 microliters of master mix was added to each well in a pre-amplification room, and sealed. The master mix consisted of $dH_2O$ plus all assay components listed above, except templates. The two plates were then transferred to a post-amplification room where 5 microliters of target was added to each well of plate 1 (excluding the 'no target' control wells). The two plates were then transferred to thermal cyclers pre-heated to 56° C. for 2-3 minute pre-incubations at 56° C. The contents of plate 2 were then transferred to plate 1 which was then incubated for 5 minutes at 56° C. (amplification step). Following this incubation, the reactions were stopped by inactivating the enzymes at 80° C. for 2 minutes. Subsequently, a molecular beacon specific for the amplified Ct P2_2 product was added to a final concentration of 300 nM and fluorescence was detected at 56° C. All samples were performed in triplicate, with error bars showing standard deviations.

The Ct P2_2 assay was performed using two templates, template 1 (5'-ATGCATGCATGAGTCACATAGGCT-TATGGAG-3' (SEQ ID NO: 4)) and template 2 (5'-ATG-CATGCATGAGTCACATTTATACCGCTTA-3' (SEQ ID NO: 5)) at a 200 nM:100 nM final template concentration. The molecular beacon used for fluorescence detection, MB 5.18, contained a 5'-FAM fluorophore and 3'-BHQ1 quencher, with the following sequence: 5'-ctggcTACCGCT-TAACTCCATAAgccag-3' (SEQ ID NO: 6).

The results are shown in FIG. 22, and show that the assay can efficiently detect less than 10 copies of target in a sample. FIG. 22B shows that even about 1-2 copies can be detected, but because of the dilution experiment, some wells may, statistically, not have any target DNA (compare FIG. 22*b*, bars 1.2 a, b, and c). The target sequence for the Ct P2_2 assay is 5'AGGCTTATGGAGTTAAGCGGTATAA-3' (SEQ ID NO: 7). Clinical samples, such as those collected on endocervical or vaginal swabs, or those collected on swabs and then transferred to viral transport media such as M4 or M5 can be prepared for use in anassay as follows. Each swab is placed into a 1.5 milliliter or 2.0 milliliter eppendorf tube containing 300 microliters to 1 milliliter of Pierce's Lyse-N-Go PCR reagent (Cat # 78882). The mixture is allowed to incubate at room temperature for 5-10 minutes, with occasional mixing. An aliquot of the eluted and lysed sample is then added directly to an assay. For samples present in viral transport media, an aliquot of the sample can be transferred to an eppendorf tube containing an equal or greater volume of Pierce's Lyse-N-Go PCR reagent (at a sample:Lyse-N-Go ratio of 1:1, 1:2, 1:10, 1:20, etc. . . .) and allowed to incubate at room temperature for 5-10 minutes, with occasional mixing. An aliquot of the eluted and lysed sample is then added directly to an assay.

Example 22

Food Safety Applications

*Listeria monocytogenes* Assay

To demonstrate the effectiveness of the assay of the present method for the specific detection of a food pathogen, assays were conducted on *Listeria monocytogenes*, one of the most significant threats to food safety from ready-to-eat food products. The assays were performed essentially as described in Example 1, with modifications described in this Example. *L. monocytogenes* strain EGD-e genomic DNA was assayed with increasing amounts of genomic DNA from the closely related non-pathogenic species *L. innocua* strain Clip11262. As shown in FIG. 23, Negative control reactions with no DNA present showed only background levels of fluorescence, and the increasing amounts of *L. innocua* DNA up to 1 million genome equivalents per 50 microliter reaction showed no significant increase in the background fluorescence. However, the addition of 1,000 genome equivalents of *L. monocytogenes* was easily detected with a substantial increase in fluorescence, and was unaffected by the presence of the *L. innocua*, even when the non-pathogenic *L. innocua* was present in 1000-fold excess, which was 1 million genome equivalents per 50 microliter reaction. Each reaction consisted of: 46 mM Tris buffer pH 8.5; 50 mM NaCl; 10 mM KCl; 10 mM $(NH_4)_2SO_4$; 5 mM $MgCl_2$;

10 mM MgSO$_4$; 0.5 mM dithiothreitol; 0.1% Triton X-100; 0.01 mM EDTA; 0.3 mM each dATP, dCTP, dGTP, and dTTP; 19.2 units Bst DNA polymerase from New England Biolabs, Inc.; 15 units Nt.BstNBI nicking endonuclease from New England Biolabs, Inc.; 200 nM of the first oligonucleotide; and 2 micromolar of the second oligonucleotide. The oligonucleotides and *Listeria* genomic DNA were incubated separately from the enzyme buffer mixture at 56° C., and then 5 microliters of this mixture was added to 45 microliters of enzyme buffer mixture. The reaction was incubated at 56° C. for 10 minutes, and then 80° C. for two minutes. After this, 3.2 microliters of a 5 µM solution of a Molecular Beacon was added to each reaction. The sequence of the Molecular Beacon was specific for the amplified *L. monocytogenes* sequence with a fluorophore and quencher on the 5' and 3' ends, respectively. Following the addition of the Molecular Beacons, the reactions were incubated at 56° C. for one minute, and then fluorescence measurements were made. Each assay condition was tested in duplicate, and the average fluorescence values are shown. The target sequence for the *Listeria monocytogenes* assay is 5'-AAAGCAAGAGAAAGTTATCGTGTAT-3' (SEQ ID NO: 8). The template sequences are as follow:

```
                                         (SEQ ID NO: 9)
T1 5'- ATGCATGCATGAGTCACATAAAGCAAGAGAA -3'
and
                                        (SEQ ID NO: 10)
T2 5'- ATGCATGCATGAGTCACATATACACGATAAC -3'.
```

Example 23

Viral RNA Example

A 10-fold dilution series of purified viral RNA from a viral positive clinical sample was used to determine the limit of detection of the assay. The viral RNA was purified using a commercially available viral RNA purification kit. A 'no target' negative control sample was included. Reactions were performed on 96-well microtiter plates in 50 microliter volumes in the following buffer: 50 mM Tris-HCl, pH 8.0, 30 mM NaCl, 15 mM (NH$_4$)$_2$(SO$_2$), 10 mM Mg$_2$SO$_4$, 1 mM DTT, 0.1% Triton X-100 with 0.1 mM dNTPs, 19.2 units of Bst DNA polymerase, 7.5 units of Nt.BstNBI nicking enzyme and 4 units of OmniScript reverse transcriptase. Templates were added at a ratio of 400 nM:20 nM (Template 1:Template 2). Reactions were performed as follows: On plate 1, 5 microliters of template mix was added to each well in a pre-amplification room, and sealed. On plate 2, 40 microliters of master mix was added to each well in a pre-amplification room, and sealed. The master mix consisted of water plus all assay components listed above, except templates. The two plates were then transferred to a post-amplification room where 5 microliters of target was added to each well of plate 1 (excluding the 'no target' control wells). The two plates were then transferred to thermal cyclers pre-heated to 56° C. for 2-3 minute pre-incubations at 56° C. The contents of plate 2 were then transferred to plate 1 which was then incubated for 5 minutes at 56° C. (amplification step). Following this incubation, the reactions were stopped by inactivating the enzymes at 80° C. for 2 minutes. Subsequently, molecular beacon specific for the amplified product was added to a final concentration of 300 nM and fluorescence was detected at 56° C. All samples were performed in triplicate, with error bars showing standard deviations. Results are shown in FIG. 24.

The viral RNA assay was performed using two templates (template 1: 31 nucleotides long, and template 2: 31 nucleotides long) at a 400 nM:20 nM final template concentration. The molecular beacon used for fluorescence detection (MB), contained a 5'-FAM fluorophore and 3'-BHQ1 quencher, with a 29 nucleotide long sequence. The length of the target sequence was 26 nucleotides.

Example 24

Agriculture Application: Detection of Genetically Modified Traits in Crops Assay Sample Preparation for Genetically Modified (GMO) and Conventional (Non-GMO) Maize The assay of the present methods may be used to detect genetically modified organisms (GMO) in agricultural applications. The assay was used to detect the presence of the bar gene, inserted into the maize genome, in a background of unmodified maize DNA. The bar gene confers resistance to the broad-spectrum herbicide glufosinate. The assays were conducted essentially as described in Example 1, with modifications as described herein. Genetically modified and conventional (unmodified) maize seeds were ground to an appropriate level of coarseness, and nucleic acids were extracted using a standard buffer. The extracted material was purified using a size-exclusion column according to the manufacturer's instructions. Purified nucleic acids were combined to yield a final concentration of 5% bar-modified maize in a conventional background (e.g., 5 microliters of bar maize DNA extract combined with 95 microliters conventional maize DNA extract), or used unmixed in the case of 100% conventional maize. The oligonucleotide sequences used to detect the bar gene are listed below.

```
                                        (SEQ ID NO: 11)
   Template 1:   ATGCATGCATGAGTCACATCATCGTCAACCA (SEQ ID NO: 12)
   Template 2:   ATGCATGCATGAGTCACATTGTCTCGATGTA
```

The templates were designed to produce the following products:

```
                                        (SEQ ID NO: 13)
    Product 1:     CATCGTCAACCACTACATCGAGACA (SEQ ID NO: 14)
    Product 2:     TGTCTCGATGTAGTGGTTGACGATG
```

The assay reagents used were: 9.6 units of Bst. Polymerase (NEB), 15 units of N.BstNBI nicking enzyme (NEB), 5 microliters Thermopol I Buffer (NEB), 2.5 microliters NEB Buffer 3, 12 mM MgSO$_4$, 0.3 mM dNTPs, 2.5% DMSO (dimethyl sulfoxide), 5 microliters sample, templates and water. The oligonucleotides were present at initial concentrations of 10 nM (Template 1) and 100 nM (Template 2). Water was used to adjust the final volume to 50 microliters, and a 10 minute assay was performed at 56° C., followed by a 2 minute incubation at 94° C. to inactivate the enzymes, followed by detection at 56° C. with a specific molecular beacon at a final concentration of 300 nM.

The sequence of this molecular beacon is:

```
                                           (SEQ ID NO: 15)
5' FAM-CCTCGCCGTCAACCACTACATCGAGCGAGG-BHQ1-3'.
```

The results are shown in FIG. 25.

Example 25

Detection of MicroRNA (miRNA)

Assay Sample Preparation for microRNAs from MDA-MB-231 Human Breast Cancer Cells:

MDA-MB-231 Human breast cancer cells (ATCC number HTB-26) are known to express elevated levels of microRNA-21 (Iorio, M. V. et al., 2005. MicroRNA gene expression deregulation in human breast cancer. *Cancer Res.* 65:7065-7070). An assay for miR-21 was developed that detects the mature microRNA-21 sequence:

```
                                           (SEQ ID NO: 16)
         5' UAGCUUAUCAGACUGAUGUUGA 3'
```

The template sequences used were (nicking enzyme sequences are underlined):

```
                                           (SEQ ID NO: 17)
   Template 1:    ATGCATGCATGAGTCACATTAGCTTATCA (SEQ ID NO: 18)
   Template 2:    ATGCATGCATGAGTCACATTCAACATCAG
```

The templates were designed to produce the following products:

```
                                           (SEQ ID NO: 19)
         Product 1:    TAGCTTATCAGACTGATGTTGA (SEQ ID NO: 20)
         Product 2:    TCAACATCAGTCTGATAAGCTA
```

The assay was conducted essentially as described in Example 1, with modifications described herein. To obtain RNA, MDA-MB-231 cells were propagated and sub-cultured, using standard methods familiar to those skilled in the art, in Dulbecco's Modified Eagle's Medium (Invitrogen) supplemented with 10% fetal bovine serum, glucose and antibiotics. Prior to reaching confluency, cells were removed from the plate by treatment with trypsin, and subsequently washed in phosphate buffered saline prior to freezing at −80° C. Cells were later defrosted and a portion used for RNA isolation with TRI Reagent (Molecular Research Center, Inc.) according to the manufacturer's instructions. Purified RNA was quantified using UV absorbance at 260 nm.

According to the Molecular Research Center TRI Reagent manual, 1 ng of purified RNA corresponds to approximately 100 cells of starting material. Various amounts of purified RNA were used in an assay comprised of the following reagents: 50 mM Tris-HCl, pH 8.0, 30 mM $(NH_4)_2SO_4$, 30 mM $Na_2SO_4$, 1 mM DTT, 0.1% Triton X-100, 10 mM $MgSO_4$, 0.1 mM dNTPs, 19.2 units of Bst. Polymerase (New England Biolabs), 7.5 units of N.BstNBI nicking enzyme (New England Biolabs), 7.4 units Omniscript Reverse Transcriptase (Qiagen), two oligonucleotides at 100 nM each, sample and water. Water was used to adjust the final volume to 50 microliters, and a 20 minute assay was performed at 56° C., followed by a 2 minute incubation at 94° C. to inactivate enzymes. The product was measured using electrospray ionization mass spectrometry, and product amounts were quantified by calculating the area under the curve. The results of the assay are shown in FIG. 26.

Example 26

Detection of a Genomic DNA Target

An assay of the present method was performed essentially as described in Example 1, using oligo templates designed to bind to a genomic target. Dilution experiments were conducted to determine the lower limit of detection. As shown in FIG. 27, there was consistent detection at 50 genome copies. When the diluted sample contained 10 genomic copies, there was detection, however, statistically, the detection was not as consistent.

Example 26 (FIG. 27) depicts a *Neisseria gonorrhoeae* assay. The assay targets the pilQ gene, specifically the sequence 5'-ACTCTACCAACACGGAACTCAAAAA-3'. (SEQ ID NO: 21) The template sequences used to amplify this target were: T1 5'-ATGCATGCATGAGTCA-CATTTTTTGAGTTCC-3' (SEQ ID NO: 22), and T2 5'-ATGCATGCATGAGTCACATACTCTACCAACA-3'(SEQ ID NO: 23). The assay was carried out essentially as described in Example 1, with the modifications herein. Briefly, the assay was performed for 5 minutes at 56° C. followed by a heat inactivation step at 80° C. for 2 minutes to stop the reaction. End point detection of amplified specific product was performed using 300 nanomolar of a molecular beacon containing a 5'-fluorophore and 3'-quencher that was specific to the amplified specific following a 1 minute incubation at 56° C. The molecular beacon sequence was: 5'-

```
                                           (SEQ ID NO: 24)
         CGCATGGAGTTCCGTGTTGGTAGACATGCG -3'.
```

Example 27

Calculation of Specific Product Generated in a *B. subtilis* Assay

Anassay of the present method was performed essentially as described in Example 1, using oligo templates designed to bind to a *Bacillis subtilis* target sequence, the target was the ppsA gene:

```
   Target sequence (25mer)
                                           (SEQ ID NO: 25)
         5'- CCAAGCTCAAAAAAGGAATCGTGAA -3'

(SEQ ID NO: 26)
      T1 5'- ATGCATGCATGAGTCACATCCAAGCTCAAAA -3'

(SEQ ID NO: 27)
      T2 5'- ATGCATGCATGAGTCACATTTCACGATTCCT -3'
```

As shown in FIG. 28, the linear regression showed an excellent correlation between the amount of the reference oligo added to a sample and area under the curve (AUC). This equation was used to determine the amount of specific product generated when 50 or 500 copies of genomic DNA target were added to a reaction. The reaction was performed for 5 minutes. The fold amplification was calculated and is presented in the Table below.

TABLE 5

Specific product 1944 yields (x = y − b/m)

| Sample | AUC signal | Product (nM) | Product (50 microliter reaction, in pmoles) | Fold amplification |
|---|---|---|---|---|
| 50-1 | 1394 | 2851 | 0.1426 | 1.72E+09 |
| 50-2 | 1495 | 3049 | 0.1525 | 1.84E+09 |
| 50-3 | 1175 | 2421 | 0.1211 | 1.46E+09 |
| 50-4 | 1072 | 2219 | 0.1110 | 1.34E+09 |
| 500-1 | 1799 | 3645 | 0.1823 | 2.20E+08 |
| 500-2 | 1837 | 3720 | 0.1860 | 2.24E+08 |
| 500-3 | 1472 | 3004 | 0.1502 | 1.81E+08 |
| 500-4 | 1438 | 2937 | 0.1469 | 1.77E+08 |

Calculations were based on the following: B. subtilis genome=4214814 nucleotides, molecular weight (g/mole) of 2781777240. Avogadro's number (molecules/mole) =6.02E+23. For 50 genome copies in moles, this results in 8.30E−23, for 500 genome copies in moles, this results in 8.30E−22.

Example 28

Effect of Different Spacer Lengths

A series of Chlamydia trachomatis (Ct) assays was performed essentially as describe in Examples 1 and 21, using various templates as shown in FIGS. 29 and 30. FIG. 29 shows the results of the reaction, FIG. 30 provides more detail as to the template design. The reaction was conducted for 10 minutes using either 0 or 100 copies of target. A series of oligonucleotide templates was prepared, with spacer region lengths (number of nucleotides on the target sequence between the binding sites of the oligo templates, if the templates were bound) ranging from 1 to 11. Optimal spacer lengths for this experiment were 1, 2, 3, or 4.

A similar set of experiments was conducted for a viral RNA target, following essentially the same methods as those described in Example 23m using spacer lengths of 2, 5, 6, 7, and 8. As determined by mass spectrometry, optimal specific product detection was found using spacer lengths of 2 and 5, and no specific product was detected in this assay where the spacer length was 6 or greater and the reaction was run for 20 minutes.

Similar experiments were also conducted with other targets. For some targets, such as miR-21, when no spacer nucleotides were included in the template design, product was detected whether or not a target sequence was present in the reaction. Product was detected whether or not target DNA was present in the assay, indicating that the template set was producing the specific product without a need for the target being present. In other experiments, a spacer region of 0 nucleotides did result in specific product. Therefore, in designing templates for the assays discussed herein, more than one set of templates should be prepared, to determine the length of the spacer region that is optimal to produce specific product from a particular target.

Example 29

Effect of the Stabilizing Regions

A set of Chlamydia trachomatis (Ct) assays was performed essentially as described in Examples 1 and 21. Templates were prepared that either included, or did not include, the stabilizing region (5'ATGCATGCAT (SEQ ID NO: 28)). The reaction was performed for 10 minutes, with either 0 or 100 copies of target DNA. Analysis was performed using real-time SybrGreen fluorescence detection. As shown in FIG. 31, the samples containing templates without stabilizing regions showed no amplification. In another set of assays, using viral RNA, either 0 or 1000 copies of target was included in the assay. The samples containing templates without stabilizing regions showed no amplification, while those with stabilizing regions showed rapid amplification.

Example 30

Effect of $Mg^{+2}$ Concentration

A set of Chlamydia trachomatis (Ct) assays was performed essentially as described in Examples 1 and 21. The assays were conducted using varying concentrations of $Mg^{+2}$. As shown in FIG. 32, for this set of assays, a complete loss of activity was found when 6 mM $Mg^{+2}$ was present, and a significant drop in activity was found when 9 mM $Mg^{+2}$ was present. At concentrations from 12 mM to 21 mM $Mg^{+2}$, the assay performed optimally.

Example 31

Examples of Other Template/Target Combinations

The present methods are not limited to the specific templates and targets provided in the present embodiments and examples. Other targets and templates may be used to perform the isothermal amplification methods discussed herein. Examples of other targets and templates include, but are not limited to, those presented in FIG. 34. Those of ordinary skill in the art recognize that other templates may be designed for the targets presented in the Figure, related target sequences to those presented in the Figure may be used in the reaction, and target sequences not included in the Figure are within the scope of the present methods.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies that are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method for amplifying a target nucleotide sequence comprising:
   (a) obtaining, from an animal, plant, or food, a sample comprising a target nucleic acid, the target nucleic acid comprising the target nucleotide sequence,
   (b) without first subjecting the target nucleic acid to a thermal denaturation step associated with amplification of the target nucleotide sequence, combining, in a single step, the obtained sample directly with an amplification reagent mixture to form a reaction mixture or diluting the obtained sample and combining, in a single step, the diluted sample with an amplification reagent mixture to form a reaction mixture, in either case, the amplification reagent mixture being free of bumper primers and comprising:
   (i) a polymerase,
   (ii) a forward template nucleic acid comprising a 5' portion that is non-complementary to the target nucleic acid sequence and contains a nicking site and a 3' template recognition region that hybridizes to the target nucleic acid sequence,
   (iii) a reverse template nucleic acid comprising a 5' portion that is non-complementary to the target nucleic acid sequence and contains a nicking site and a 3' recognition region that hybridizes to the target nucleic acid sequence, and
   (iv) one or more nicking enzymes;
   (c) subjecting the reaction mixture formed by the step of combining to essentially isothermal conditions to amplify the target nucleotide sequence without the assistance of bumper primers, wherein amplification is performed, in the presence of the one or more nicking enzymes, by multiple cycles of the polymerase extending the reverse template nucleic acid along the target nucleotide sequence and extending the forward template nucleic acid along the complement of the target nucleotide sequence, thereby producing a double-stranded nucleic acid amplification product comprising first and second double-stranded nicking sites spaced apart by the target nucleotide sequence;
   and
   (d) detecting the amplified target nucleotide sequence in real time within 10 minutes of subjecting the reaction mixture formed by the step of combining to essentially isothermal conditions, wherein:
   (i) the target nucleotide sequence is between 20 and 40 nucleotides in length; and
   (ii) the target nucleotide sequence is amplified 1E+6-fold or more in about ten minutes.

2. The method of claim 1, wherein the forward template recognition region is 8-15 nucleotides long and the reverse template recognition region is 8-15 nucleotides long.

3. The method of claim 1, wherein the target nucleotide sequence comprises from 1 to 5 nucleotides more than the sum of the nucleotides of the forward template recognition region and the reverse template recognition region.

4. The method of claim 3, wherein the target nucleotide sequence comprises one nucleotide more than the sum of the nucleotides of the forward template recognition region and the reverse template recognition region.

5. The method of claim 3, wherein the target nucleotide sequence comprises two nucleotides more than the sum of the nucleotides of the forward template recognition region and the reverse template recognition region.

6. The method of claim 3, wherein the target nucleotide sequence comprises three nucleotides more than the sum of the nucleotides of the forward template recognition region and the reverse template recognition region.

7. The method of claim 1, wherein the target nucleic acid is double-stranded DNA.

8. The method of claim 1, wherein the target nucleic acid is single-stranded DNA.

9. The method of claim 1, wherein the target nucleic acid is RNA.

10. The method of claim 1, wherein the target nucleic acid is selected from the group consisting of genomic DNA, plasmid DNA, viral DNA, mitochondrial DNA, cDNA, synthetic double-stranded DNA and synthetic single-stranded DNA.

11. The method of claim 1, wherein the target nucleic acid is selected from the group consisting of messenger RNA, viral RNA, ribosomal RNA, transfer RNA, micro RNA, micro RNA precursor, and synthetic RNA.

12. The method of claim 1, wherein the polymerase is a thermophilic polymerase.

13. The method of claim 12, wherein the polymerase is selected from the group consisting of Bst (large fragment) and 9°N.

14. The method of claim 13, wherein the polymerase is Bst (large fragment).

15. The method of claim 1, wherein the one or more nicking enzyme are selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, Nt.BspD6I, and Nt.Bpu10I.

16. The method of claim 1, wherein the forward template nucleic acid is provided at the same concentration as the reverse template nucleic acid.

17. The method of claim 1, wherein the ratio of the forward template nucleic acid to the reverse template nucleic acid is between 1:100 and 100:1.

18. The method of claim 1, wherein two or more polymerases are combined.

19. The method of claim 18, wherein at least one of the polymerases comprises reverse transcriptase activity.

20. The method of claim 1, wherein the temperature of the substantially isothermal conditions is between 54° C. and 60° C.

21. The method of claim 20, wherein the temperature of the substantially isothermal conditions is between 56° C. and 58° C.

22. The method of claim 1, wherein the amplification is conducted for 1 to 10 minutes.

23. The method of claim 1, wherein the amplification is conducted for 1 to 20 minutes.

24. The method of claim 1, wherein said amplification product is detected by a detection method selected from the group consisting of fluorescence, intercalating dye detection, fluorescence resonance energy transfer (FRET), molecular beacon detection, and incorporation of labeled nucleotides.

25. The method of claim 1, wherein at least two different target nucleotide sequences are amplified.

26. The method of claim 1, wherein at least one of the forward template nucleic acid and reverse template nucleic acid comprises a spacer, blocking group, a modified nucleotide or combination thereof.

27. The method of claim 1, wherein the target nucleotide sequence is amplified 1E+6-fold or more in about five minutes.

28. The method of claim 1, wherein the target nucleotide sequence is amplified 1E+6-fold or more in about 2.5 minutes.

29. The method of claim 1, wherein the target nucleotide sequence is amplified 1E+7-fold or more in about five minutes.

30. The method of claim 1, wherein the target nucleotide sequence is amplified 1E+8-fold or more in about five minutes.

31. The method of claim 1, wherein the target nucleotide sequence is amplified 1E+9-fold or more in about five minutes.

32. A method for amplifying a target nucleotide sequence comprising:
(a) obtaining, from an animal, plant, or food, a sample comprising a target nucleic acid, the target nucleic acid comprising the target nucleotide sequence,
(b) without first subjecting the target nucleic acid to a thermal denaturation step associated with amplification of the target nucleotide sequence, combining, in a single step, the obtained sample directly with an amplification reagent mixture to form a reaction mixture or diluting the obtained sample and combining, in a single step, the diluted sample with an amplification reagent mixture to form a reaction mixture, in either case, the amplification reagent mixture being free of bumper primers and comprising:
(i) a polymerase,
(ii) a forward template nucleic acid comprising a 5' portion that is non-complementary to the target nucleic acid sequence and contains a nicking site and a 3' template recognition region that hybridizes to the target nucleic acid sequence, and
(iii) a reverse template nucleic acid comprising a 5' portion that is non-complementary to the target nucleic acid sequence and contains a nicking site and a 3' template recognition region that hybridizes to the target nucleic acid sequence, and
(iv) one or more nicking enzymes;
(c) subjecting the reaction mixture formed by the step of combining to essentially isothermal conditions to amplify the target nucleotide sequence without the assistance of bumper primers, thereby generating, in the presence of the nicking enzymes, a double-stranded nucleic acid product comprising first and second double-stranded nicking sites spaced apart by the target nucleotide sequence; and
(d) detecting amplified target nucleotide sequence in real time within 10 minutes of subjecting the reaction mixture formed by the step of combining to essentially isothermal conditions, wherein:
the target nucleotide sequence is amplified 1E+6-fold or more in about ten minutes.

33. The method of claim 1 or 32, wherein the sample is obtained from an animal and is blood, mucus, sputum, saliva, tears, feces or urine of the animal.

34. The method of claim 33, wherein the sample is obtained from an animal and is mucus, sputum, or saliva of the animal.

35. The method of claim 1 or 32, wherein the sample is obtained from an animal and the animal is a human.

36. The method of claim 1 or 32, wherein the sample is obtained from an animal and the target nucleic acid is a target nucleic acid of an animal pathogen.

37. The method of claim 36, wherein the animal pathogen is a single-stranded DNA virus, double-stranded DNA virus, or single-stranded RNA virus.

38. The method of claim 36, wherein the animal pathogen is a bacterium.

* * * * *